US007119190B2

(12) United States Patent
Liaw et al.

(10) Patent No.: US 7,119,190 B2

(45) Date of Patent: Oct. 10, 2006

(54) ENDOGENOUS AND NON-ENDOGENOUS VERSIONS OF HUMAN G PROTEIN-COUPLED RECEPTORS

(75) Inventors: Chen W. Liaw, San Diego, CA (US); Derek T. Chalmers, Cardiff, CA (US); Dominic P. Behan, San Diego, CA (US); Dominique Maciejewski-Lenior, San Diego, CA (US); James N. Leonard, San Diego, CA (US); I-Lin Lin, San Diego, CA (US); Daniel Ortuño, Vista, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 647 days.

(21) Appl. No.: 10/083,168

(22) Filed: Feb. 26, 2002

(65) Prior Publication Data

US 2003/0023069 A1 Jan. 30, 2003

Related U.S. Application Data

(63) Continuation-in-part of application No. 09/170,496, filed on Oct. 13, 1998, now Pat. No. 6,555,339, and a continuation-in-part of application No. 09/060,188, filed on Apr. 14, 1998, which is a continuation-in-part of application No. 08/839,449, filed on Apr. 14, 1997, now abandoned.

(60) Provisional application No. 60/271,913, filed on Feb. 26, 2001.

(51) Int. Cl.
*C07H 21/04* (2006.01)
*C12N 15/63* (2006.01)
*C12N 15/09* (2006.01)

(52) U.S. Cl. ................ 536/23.5; 435/69.1; 435/172.3; 435/235.1; 435/325; 435/320.1; 536/350

(58) Field of Classification Search ............... 435/69.1, 435/252.3, 325, 7.1; 530/300, 350; 536/23.1, 536/24.31

See application file for complete search history.

(56) References Cited

U.S. PATENT DOCUMENTS

| | | | | |
|---|---|---|---|---|
| 5,514,578 | A | 5/1996 | Hogness et al. | 435/240.2 |
| 5,532,157 | A | 7/1996 | Fink | 435/240.2 |
| 5,573,944 | A | 11/1996 | Kirschner et al. | 435/252.3 |
| 5,639,616 | A | 6/1997 | Liao et al. | 435/7.1 |
| 5,750,353 | A | 5/1998 | Kopin et al. | 435/7.21 |
| 5,861,309 | A | 1/1999 | Bard et al. | 135/325 |
| 5,891,720 | A | 4/1999 | Moore et al. | 435/325 |
| 5,955,308 | A | 9/1999 | Bergsma et al. | 435/69.1 |
| 6,159,705 | A | 12/2000 | Truehart et al. | |
| 6,235,481 | B1 * | 5/2001 | Horikawa et al. | 435/6 |

FOREIGN PATENT DOCUMENTS

| | | |
|---|---|---|
| CA | 2135253 | 8/1996 |
| EP | 0 612 845 A2 | 8/1994 |
| EP | 0 878 542 A2 | 11/1998 |
| EP | 0 892 051 A2 | 1/1999 |
| EP | 1 090 989 A1 | 4/2001 |
| EP | 1 094 076 A1 | 4/2001 |
| JP | 11-98988 | 9/1999 |
| WO | WO 96/05302 | 2/1996 |
| WO | WO 97/11159 | 9/1996 |
| WO | WO 97/21731 | 6/1997 |
| WO | WO 97/21731 A | 6/1997 |
| WO | WO 98/00552 | 1/1998 |
| WO | WO 98/29439 | 7/1998 |
| WO | WO 98/34948 | 8/1998 |
| WO | WO 98/38217 A | 9/1998 |
| WO | WO 98/46620 | 10/1998 |
| WO | WO 98/46995 | 10/1998 |
| WO | WO 98/56820 | 12/1998 |
| WO | WO 99/06552 | 2/1999 |
| WO | WO/99 24569 | 5/1999 |
| WO | WO 99/32519 | 7/1999 |
| WO | WO 99/48921 | 9/1999 |
| WO | WO 99/52927 | 10/1999 |
| WO | WO 00/14229 | 3/2000 |
| WO | WO 00/22131 | 4/2000 |
| WO | WO 00/49046 | 8/2000 |
| WO | WO 01/07606 A1 | 2/2001 |
| WO | WO 01/09184 A1 | 2/2001 |
| WO | WO 01/12673 A1 | 2/2001 |
| WO | WO 01/14577 A1 | 3/2001 |
| WO | WO 01/16159 A1 | 3/2001 |
| WO | WO 01/31014 A2 | 5/2001 |
| WO | WO 01/36471 A2 | 5/2001 |

OTHER PUBLICATIONS

Bao, et al., Database SwissProt. Acc. No. P25089, May 1, 1992, Alignment for SEQ ID No. 2.

Bao, et al, Database PIR 73, Acc. No. C42009, Sep. 30, 1993, Alignment for SEQ ID No. 3.

Durstin, et al., EMBL Database, Acc No. AC005946, Nov. 8, 1994, Alignment for SEQ ID No. 1.

(Continued)

*Primary Examiner*—Janet L. Andres
*Assistant Examiner*—Nirmal S. Basi
(74) *Attorney, Agent, or Firm*—Michael A. Patane; Cozen O'Connor

(57) ABSTRACT

The invention disclosed in this patent document relates to transmembrane receptors, more particularly to a human G protein-coupled receptor and to mutated (non-endogenous) versions of the human GPCRs for evidence of constitutive activity.

8 Claims, 21 Drawing Sheets

OTHER PUBLICATIONS

Lamerdin, et al., EMBL Database, Acc. No. AC005946, Nov. 7, 1998, Alignment for SEQ ID No. 1.
Lamerdin, et al., EMBL Database, Acc No. AC06272, Jan. 4, 1999, Alignment for SEQ ID No. 1.
Alla, S.A. et al., "Extracellular domains of the bradykinin B2 receptor involved in ligand binding and agonist sensing defined by anti-peptide antibodies," *J. Biol. Chem.*, 1996, 271, 1748-1755.
Advenier, C. et al., "Effects on the isolated human bronchus of SR 48968, a potent and selective nonpeptide antagonist of the neurokinin A ($NK_2$) receptors," *Am. Rev. Respir. Dis.*, 1992, 146(5, Pt. 1), 1177-1181.
Alexander, W.S. et al., "Point mutations within the dimer interfact homology domain of c-Mpl induce constitutive receptor activity and tumorigenicity," *EMBO J.*, 1995, 14(22), 5569-5578.
Arvanitikis, L. et al., "Human herpesvirus KSHV encodes a constitutively active G-protein-coupled receptor linked to cell proliferation," *Nature*, 1997, 385, 347-349.
Barker, E.L. et al., "Constitutively active 5-hydroxytryptamine$_{2C}$ receptors reveal novel inverse agonist activity of receptor ligands," *J. Biol. Chem.*, 1994, 269(16), 11687-11690.
Baxter, G., "5-$HT_2$ receptors: a family re-united?" *Trends Pharmacol. Sci.*, 1995, 16, 105-110.
Besmer, P. et al., "A new acute transforming feline retrovirus and relationship of its oncogene v-*kit* with the protein kinase gene family," *Nature*, 1986, 320, 415.
Blin, et al., "Mapping of single amino acid residues required for selective activation of $G_{q/11}$ by the m3 muscarinic acetylcholine receptor," *J. Biol. Chem.*, 1995, 270, 17741-17748.
Bond, R.A. et al., "Inverse agonists and G-protein-coupled receptors," in *Receptor-Based Drug Design*, Leff, P. (ed.), New York, M. Dekker, 1998, 363-377.
Boone, C. et al., "Mutations that alter the third cytoplasmic loop of the a-factor receptor lead to a constitutive and hypersensitive phenotype," *Proc. Natl. Acad. Sci. USA*, 1993, 90(21), 9921-9925.
Burstein, E.S. et al., "Constitutive activation of chimeric m2/m5 muscarinic receptors and delineation of G-protein coupling selectivity domains," *Biochem. Pharmacol.*, 1996, 51(4), 539-544.
Burstein, E.S. et al., "Amino acid side chains that define muscarinic receptor/G-protein coupling. Studies of the third intracellular loop," *J. Biol. Chem.*, 1996, 271(6), 2882-2885.
Burstein, E.S. et al., "Constitutive activation of muscarinic receptors by the G-protein $G_{q}$," *FEBS Lett.*, 1995, 363(3), 261-263.
Bylund, D., "International union of pharmacology nomenclature of adrenoceptors," *Pharmacol. Rev.*, 1994, 46, 121-136.
Casey, C. et al., "Constitutively active mutant 5-$HT_{2A}$ serotinin receptors: inverse agonist activity of classical $5HT_{2A}$ antagonists," *Soc. Neurosci.*, 1996, Abstract #699.10.
Cheatham, B. et al., "Substitution of the *erbB-2* oncoprotein transmembrane domain activates the insulin receptor and modulates the action of insulin-receptor substrate 1," *Proc. Natl. Acad. Sci. USA*, 1993, 90, 7336-7340.
Chen, J. et al., "Tethered Ligand Library for Discovery of Peptide Agonists," *J. Biol. Chem.*, 1995, 270, 23398-23401.
Chen, T.S. et al., "Microbiol hydroxylation and glucuronidation of the angiotensin II (AII) receptor antagonist MK 954," *J. Antibiot. (Tokyo)*, 1993, 46(1), 131-134.
Chen, W. et al., "A colorimetric assay for measuring activation of $G_s$- and $G_q$-coupled signaling pathways," *Anal. Biochem.*, 1995, 226(2), 349-354.
Chidiac, P. et al., "Inverse agonist activity of β-adrenergic antagonists," *J. Pharm. Exp. Ther.*, 1994, 45, 490-499.
Clozel, M. et al., "In vivo pharmacology of Ro 46-2005, the first synthetic nonpeptide endothelin receptor antagonist: implications for endothelin physiology," *J. Cardiovas. Pharmacol.*, 1993, 22(Suppl. 8), S377-S-379.
Collesi, C. et al., "A splicing variant of the *RON* transcript induces constitutive tyrosine kinase activity and an invasive phenotype," *Mol. Cell. Biol.*, 1996, 16(2), 5518-5526.
Cooper, C.S. et al., "Molecular cloning of a new transforming gene from a chemically transformed human cell line," *Nature*, 1984, 311, 29-33.
De Dios, I. et al., "Effect of L-364,718 (CCK Receptor Antagonist) on Exocrine Pancreatic Secretion of Hydrocortison-Treated Rats," *Pancreas*, 1994, 9(2), 212-218.
Desbios-Mouthon, C. et al., "Deletion of $Asn^{281}$ in the α-subunit of the human insulin receptor causes constitutive activation of the receptor and insulin desensitization," *J. Clin. Endocrinol. Metab.*, 1996, 81(2), 719-727.
Di Renzo, M.F. et al., "Expression of the Met/HGF receptor in normal and neoplastic human tissues," *Oncogene*, 1991, 6(11), 1997-2003.
Di Renzo, M.F. et al., "Overexpression of the c-*MET*/HGF receptor gene in human thyroid carcinomas," *Oncogene*, 1992, 7, 2549-2553.
Duprez, L. et al., "Germline mutations of the thyrotropin receptor gene cause non-autoimmune autosomal dominant hyperethyroidism," *Nature Genetics*, 1994, 7, 396-401.
Eggericksx, D. et al., "Molecular Cloning of an Orphan G-Protein-Coupled Receptor that Constitutively Activates Adenylate Cyclase," *Biochem. J.*, 1995, 309, 837-843.
Evans, B.E. et al., "Orally Active, Nonpeptide Oxytocin Antagonists," *J. Med. Chem.*, 1992, 35, 3919-3927.
Fu, M. et al., "Functional autoimmune epitope on $\alpha_1$-adrenergic receptors in patients with malignant hypertension," *Lancet*, 1994, 344, 1660-1663.
Furitsu, T. et al., "Identification of Mutations in the Coding Sequence of the Proto-oncogene c-*kit* in a Human Mast Cell Leukemia Cell Line Causing Ligand-independent Activation of c-*kit* Product," *J. Clin. Invest.*, 1993, 92, 1736-1744.
Gellai, M. et al., "Nonpeptide Endothelin Receptor Antagonists V: Prevention and Reversal of Acute Renal Failure in the Rat by SB 209670," *J. Pharm. Exp. Therap.*, 1995, 275(1), 200-206.
Gitter, B. et al., "Pharmacological Characterization of LY303870: A Novel Potent and Selective Nonpeptide Substance P (Neurokinin-1) Receptor Antagonist," *J. Pharm. Exp. Therp.*, 1995, 275(2), 737-744.
Gouilleux-Gruart, V. et al., "STAT-Related Transcription Factors are Constitutively Activated in Peripheral Blood Cells from Acute Leukemia Patients," *Blood*, 1996, 87(5), 1692-1697.
Hansson, J.H. et al., "Hypertension caused by a truncated epithelial sodium channel γ subunit: genetic heterogeneity of Liddle syndrome," *Nat. Genet.*, 1995, 11(1), 76-82.
Hasegawa, H. et al., "Two Isoforms of the Prostaglandin E Receptor EP3 Subtype Different in Agonist-independent Constitutive Activity," *J. Biol. Chem.*, 1996, 271(4), 1857-1860.
Hendler, F. et al., "Human Squamous Cell Lung Cancers Express Increased Epidermal Growth Factor Receptors," *J. Clin. Invest.*, 1984, 74, 647-651.
Herrick-Davis, K. et al., "Constitutively Active 5HT2C Serotonin Receptor Created by Site-Directed Mutagenesis," *Soc. Neurosci.*, Abstract No. 699.18.
Hieble, J., "International union of pharmacology. X. Recommendation for nomenclature of 1-adrenoceptors," *Pharm. Rev.*, 1995, 47, 267-270.
Hill, S., "Distribution, Properties, and Functional Characteristics of Three Classes of Histamine Receptor," *Am. Soc. Pharm. Exp. Therap.*, 1990, 42(1), 45-83.
Högger, P. et al., "Activating and Inactivating Mutations in—and C-terminal i3 Loop Junctions of Muscarinic Acetylcholine Hm1 Receptors," *J. Biol. Chem.*, 1995, 270(13), 7405-7410.
Ikeda, H. et al., "Expression and Functional Role of the Proto-oncogene c-*kit* in Acute Myeloblastic Leukemia Cells," *Blood*, 1991, 78(11), 2962-2968.
Imura, R. et al., "Inhibition by HS-142-1, a novel nonpeptide atrial natriuretic peptide antagonist of microbial origin, of atrial natriuretic peptide-induced relaxation of isolated rabbit aorta through the blockade of guanylyl cyclase-linked receptors," *Mol. Pharm.*, 1992, 42, 982-990.
Jakubik, J. et al., "Constitutive activity of the $M_1$-$M_4$ subtypes of muscarinic receptors in transfected CHO cells and of muscarinic receptors in the heart cells revealed by negative antagonists," *FEBS Letts.*, 1995, 377, 275-279.

Kjelsberg, M.A. et al., "Constitutive activation of the $\alpha_{1B}$-adrenergic receptor by all amino acid substitutions at a single site," *J. Biol. Chem*., 1992, 267(3), 1430-1433.
Knapp, R. et al., "Molecular biology and pharmacology of cloned opioid receptors," *FASEB J*., 1995, 9, 516-525.
Kosugi, S. et al., "Characterization of heterogeneous mutations causing constitutive activation of the luteinizing hormone receptor in familial male precocious puberty," *Human Mol. Genetics*, 1995, 4(2), 183-188.
Kosugi, S. et al., "Identification of Thyroid-Stimulating Antibody-Specific Interaction Sites in the N-Terminal Region of the Thyrotropin Receptor," *Mol. Endocrinology*, 1993, 7, 114-130.
Kraus, M. et al., "Demonstration of ligand-dependent signaling by the *erbB-3* tyrosine kinase and its constitutive activation in human breast tumor cells," *Proc. Natl. Acad. Sci. USA*, 1993, 90, 2900-2904.
Kudlacz, E. et al., "*In Vitro* and *In Vivo* Characterization of MDL 105,212A, a Nonpeptide NK-1/NK-2 Tachykinin Receptor Antagonist," *J. Pharm. Exp. Therap*., 1996, 277(2), 840-851.
Kuriu, A. et al., "Proliferation of Human Myeloid Leukemia Cell Line Associated with the Tyrosine-Phosphorylation and Activation of the Proto-oncogene c-*kit* Product," *Blood*, 78(11), 2834-2840.
Labbé-Jullié, C. et al., "Effect of the nonpeptide neurotensin antagonist, SR 48692, and two enantiomeric analogs, SR 48527 and SR 49711, on neurotension binding and contractile responses in guinea pig ileum and colon," *J. Pharm. Exp. Therap*., 1994, 271(1), 267-276.
Latronico, A. et al., "A novel mutation of the luteinizing hormone receptor gene causing male gonadotropin-independent precocious puberty," *J. Clin. Endocrinol. Metabl*., 1995, 80(8), 2490-2494.
Laue, L. et al., "Genetic heterogeneity of constitutively activating mutations of the human luteinizing hormone receptor in familial male-limited precocious puberty," *Proc. Natl. Acad. Sci USA*, 1995, 92, 1906-1910.
Løvlie, R. et al., "The $Ca^{2+}$-sensing receptor gene (PCAR1) mutation T151M in isolated autosomal dominant hypoparathyroidism," *Hum. Genet*, 1996, 98, 129-133.
Lefkowitz, R. et al., "Constitutive activity of receptors coupled to guanine nucleotide regulatory proteins," *Trends Pharmacol. Sci*., 1993, 14, 300-307.
Libermann, T. et al., "Amplification, enhanced expression and possible rearrangement of EGF receptor gene in primary human brain tumours of glial origin," *Nature*, 1985, 313, 144-147.
Liu, C. et al., "Overexpression of c-*met* proto-oncogene but not epidermal growth factor receptor or c-*erb*B-2 in primary human colorectal carcinomas," *Oncogene*, 1992, 7, 181-185.
Liu, J. et al., "Molecular mechanisms involved in muscarinic acetylcholine receptor-mediated G protein activation studied by insertion mutagenesis," *J. Biol. Chem*., 1996, 271(11), 6172-6178.
Lonardo, F. et al., "The normal *erb*B-2 product is an atypical receptor-like tyrosine kinase with constitutive activity in the absence of ligand," *New Biologist*, 1990, 2(11), 992-1003.
Maenhaut, C. et al., "RDC8 codes for an adenosine A2 receptor with physiological constitutive activity," *Biochem. Biophys. Res. Comm*., 1990, 173(3), 1169-1178.
Mann, J. et al., "Increased $serotonin_2$ and β-adrenergic receptor binding in the frontal cortices of suicide victims," *Arch. Gen. Psychiatry*, 1986, 43, 954-959.
Marone, R.L. et al., "Human CRF receptor chimeras: Mapping of ligand binding determinants," 26th Meeting of the Society of Neuroscience, Washington, D.C. Nov. 16-21, 1996, Abstract No. 609.8.
Magnusson, Y. et al., "Autoimmunity in idiopathic dilated cardiomyopathy," *Circulation*, 1994, 89, 2760-2767.
Matus-Leibovitch, N. et al., "Truncation of the thyrotropin-releasing hormone receptor carboxyl tail causes constitutive activity and leads to impaired responsiveness in *Xenopus* Oocytes and AtT20 Cells," *J. Biol. Chem*., 1995, 270(3), 1041-1047.
Myles, G.M. et al., "Tyrosine 569 in the c-Fms juxtamembrane domain is essential for kinase activity and macrophage colony-stimulating factor-dependent internalization," *Mol. Cell. Biol*., 1994, 14(7), 4843-4854.
Nanevicz, T. et al., "Thrombin receptor activating mutations," *J. Biol. Chem*., 1996, 271(2), 702-706.
Natali, P.G. et al., "Expression of the c-Met/HGF receptor in human melanocytic neoplasms: demonstration of the relationship to malignant melanoma tumour progression," *Br. J. Cancer*, 1993, 68, 746-750.
Neilson, K.M. et al., "Constitutive activation of fibroblast growth factor receptor-2 by a point mutation associated with Crouzon syndrome," *J. Biol. Chem*., 1995, 270(44), 26037-26040.
Oda, S. et al., "Pharmacological profile of HS-142-1, a novel nonpeptide atrial natriuretic peptide (ANP) antagonist of microbial origin. II. Restoration by HS-142-1 of ANP-induced inhibition of aldosterone production in adrenal glomerulosa cells," *J. Pharm. Exp. Ther*., 1992, 263(1), 241-245.
O'Dowd, B.F. et al., "Site-directed mutagenesis of the cytoplasmic domains of the human β2-adrenergic receptor," *J. Biol. Chem*., 1988, 263(31), 15985-15992.
Offermanns, S. et al., "$G\alpha_{15}$ and $G\alpha_{16}$ Couple a Wide Variety of Receptors to Phospholipase C," *J. Biol. Chem*., 1995, 270, 15175-15180.
Palkowitz, A.D. et al., "Structural evolution and pharmacology of a novel series of triacid angiotensin II receptor antagonists," *J. Med. Chem*., 1994, 37, 4508-4521.
Parent, J. et al., "Mutations of two adjacent amino acids generate inactive and constitutively active forms of the human platelet-activating factor receptor," *J. Biol. Chem*., 1996, 271(14), 7949-7955.
Parfitt, A.M. et al., "Hypercalcemia due to constitutive activity of the parathyroid hormone (PTH)/PTH-related peptide receptor: comparison with primary hyperparathyroidism," *J. Clin. Endocr. Metabl*., 1996, 81, 3584-3588.
Parma, J. et al., "Somatic mutations in the thyrotropin receptor gene cause hyperfunctioning thyroid adenomas," *Nature*, 1993, 365, 649-651.
Pei, G. et al., "A constitutive active mutant $\beta_2$-adrenergic receptor is constitutively desensitized and phosphorylated," *Proc. Natl. Acad. Sci. USA*, 1994, 91, 2699-2702.
Pendley, C.E. et al., "The gastrin/cholecystokinin-B receptor antagonist L-365,260 reduces basal $_1$acid secretion and prevents gastrointestinal damage induced by aspirin, ethanol and cysteamine in the rat," *J. Pharmacol. Exp. Ther*., 1993, 265(3), 1348-1354.
Peroutka, S., "Serotonin receptor subtypes. Their evolution and clinical relevance," *CNS Drugs*, 1995, 4 (Suppl. 1), 18-28.
Pettibone, D.J. et al., "Development and pharmacological assessment of novel peptide and nonpeptide oxytocin antagonists," *Regul. Pept*., 1993, 45, 289-293.
Prat, M.P. et al., "The receptor encoded by the human c-*Met* oncogene is expressed in hepatocytes, epithelial cells and solid tumors," *Int. J. Cancer*, 1991, 49, 323-328.
Prezeua, L. et al., "Changes in the carboxy-terminal domain of metabotropic glutamate receptor 1 by alternate splicing generate splicing generate receptors with differing agonist-independent activity," *Mol. Pharmacol*., 1996, 49, 422-429.
Rakovska, A. et al., "Effect of loxiglumide (CR 1505) on CCK-induced contractions and $^3$H-acetylcholine release from guinea-pig gallbaldder," *Neuropeptides*, 1993, 25(5), 271-276.
Ren, Q. et al., "Constitutive active mutants of the $\alpha_2$-adrenergic receptor," *J. Biol. Chem*., 1993, 268, 16483-16487.
Reynolds, E.E. et al., "Pharmacological characterization of PD 156707, an orally active $ET_A$ receptor antagonist," *J. Pharmacol. Exp. Ther*., 1995, 273(3), 1410-1417.
Robbins, L.S. et al., "Pigmentation phenotypes of variant extension locus alleles result from point mutations that alter MSH receptor function," *Cell*, 1993, 72, 827-834.
Rong, S. et al., "Met expression and sarcoma tumorigenicity," *Cancer*, 1993, 53(22), 5355-5360.
Samama, P. et al., "A mutation-induced activation state of the β2-adrenergic receptor," *J. Biol. Chem*., 1993, 268(7), 4625-4636.
Sautel, M. et al., "Neuropeptide Y and the nonpeptide antagonist BIBP 3226 share an overlapping binding site at the human Y1 receptor," *Am. Soc. Pharm. Exp. Ther*., 1996, 50, 285-292.

Sawutz, D.G. et al., "Pharmacology and structure-activity relationships of the nonpeptide bradykinin receptor antagonist WIN 64338," *Can. J. Physiol. Pharmacol.*, 1995, 73, 805-811.
Scheer, A. et al., "Constitutively active G protein-coupled receptors: potential mechanisms of receptor activation," *J. Rec. Signal Transduct. Res.*, 1997, 17(1-3), 57-73.
Scheer, A. et al., "The activation process of the $\alpha_{1B}$-adrenergic receptor: Potential role of protonation and hydrophobicity of a highly conserved aspartate," *Proc. Natl. Acad. Sci. USA*, 1997, 94, 808-813.
Schwinn, D.A. et al., "Cloning and pharmacological characterization of human *Alpha*-1 adrenergic receptors: sequence corrections and direct comparison with other species homologues," *J. Pharmacol.*, 1995, 272(1), 134-142.
Schild, L. et al., "A mutation in the epithelial sodium channel causing Liddle disease increases channel activity in the *Xenopus laevis* oocyte expression system," *Proc. Natl. Acad. Sci. USA*, 1995, 92, 5699-5703.
Seeman, P. et al., "Dopamine receptor pharmacology," *Trends Pharmacol. Sci.*, 1994, 15, 264-270.
Seeman, P. et al., "Dopamine D4 receptors elevated in schizophrenia," *Nature*, 1993, 365, 441-445.
Serradeil-Le Gale, C. et al., "Biochemical and pharmacological properties of SR 49059, a new, potent, nonpeptide antagonist of rat and human vasopressin $V_{1a}$ receptors," *J. Clin. Invest.*, 1993, 92, 224-231.
Sharif, M. et al., "Malignant transformation by G protein-coupled hormone receptors," *Mol. Cell. Endocrinology*, 1994, 100, 115-119.
Showers, M.O. et al., "Activation of the erythropoietin receptor by the Friend spleen focus-forming virus gp55 glycoprotein induces constitutive protein tyrosine phosphorylation," *Blood*, 1992, 80(12), 3070-3078.
Skinner, R.H. et al., "Direct measurement of the binding of RAS to neurofibromin using scintillation proximity assay," *Anal. Biochem.*, 1994, 223, 259-265.
Slamon, D.J. et al., "Human breast cancer: correlation of relapse and survival with amplification of the HER-2/*neu* oncogene," *Science*, 1987, 235, 177-182.
Slamon, D. et al., "Studies of the HER-2/*neu* proto-oncogene in human breast and ovarian cancer," *Science*, 1989, 244, 707-712.
Solomon, Y. et al., "A highly sensitive adenylate cyclase assay," *Anal. Biochem.*, 1974, 58, 541-548.
Spiegel, A.M., "Defects in G protein-coupled signal transduction in human disease," *Ann. Rev. Physiol.*, 1995, 58, 143-170.
ter Laak, A., "Modelling and mutation studies on the histamine $H_1$-receptor agonist binding site reveal different binding modes for $H_1$-agonists: $Asp^{116}$ (TM3) has a constitutive role in receptor stimulation," *J. Computer-Aided Mol. Design*, 1995, 9, 319-330.
Tiberi, M. et al., "High agonist-independent activity is a distinguishing feature of the dopamine D1B receptor subtype," *J. Biol. Chem.*, 1994, 269(45), 27925-27931.
Tsujimura, T. et al., "Constitutive activation of c-*kit* in FMA3 murine mastocytoma cells caused by deletion of seven amino acids at the juxtamembrane domain," *Blood*, 1996, 87(1), 273-283.
Wang, Z. et al., "Constitutive μ opioid receptor activation as a regulatory mechanism underlying narcotic tolerance and dependence," *Life Sci.*, 1994, 54(20), 339-350.
Watowich, S.S. et al., "Homodimerization and constitutive activation of the erythropoietin receptor," *Proc. Natl. Acad. Sci USA*, 1992, 89, 2140-2144.
Weber-Nordt, R.M. et al., "Constitutive activation of STAT proteins in primary lymphoid and myeloid leukemia cells and in Epstein-Barr virus (EBV)-related lymphoma cell lines," *Blood*, 1996, 88(3), 809-816.
Webster, M.K. et al., "Constitutive activation of fibroblast growth factor receptor 3 by the transmembrane point mutation found in achondroplasia," *EMBO J.*, 1996, 15, 520-527.
Xu, Y. et al., "Characterization of epidermal growth factor receptor gene expression in malignant and normal human cell lines," *Proc. Natl. Acad. Sci. USA*, 1984, 81, 7308-7312.
Yamada, K. et al., "Substitution of the insulin receptor transmembrane domain with the *c-neu/erbB2* transmembrane domain constitutively activates the insulin receptor kinas *in vitro,*" *J. Biol. Chem.*, 1992, 267(18), 12452-12461.
Zhang, S. et al., "Identification of Dynorphins as Endogenous Ligands for an Opioid Receptor-Like Orphan Receptor," *J. Biol. Chem.*, 1995, 270, 22772-22778.
Zhen, Z. et al., "Structural and functional domains critical for constitutive activation of the HGF-receptor (*Met*)," *Oncogene*, 1994, 9, 1691-1697.
Pauwles, P.J. et al., "Review: Amino Acid Domains Involved in Constituve Activation of G-Protein-Coupled Receptors", *Molecular Neurobiology*, 1998, 17, 109-135.
Shryock, J. et al., "Inverse Agonists and Neutral Antagonists of Recombinant Human A1 Adenosine Receptors Stably Expressed in Chinese Hamster Ovary Cells", *Molecular Pharmacology*, 1998, 53, 886-893.
Wenzel-Seifert, et al., "High Constitutive Activity of the Human Fromyl Peptide Receptor", *Journal of Biological Chem.*, 1998, 273, 24181-24189.
Forman, B.M. et al., "Androstane Metabolites Bind to and Deactivate the Nuclear Receptor CAR-β", *Nature*, 1998, 395, 612-615.
Seifert, R. et al., different Effects of Gsβ Splice Variants on β2-Adrenoreceptor-mediated Signaling, *Jrl. of Biological Chem.*, 1998, 273, 5109-5116.
Abola, A.P. et al., "Omo sapiens chromosome 13 clone RP11-286P8, complete sequence," AC026756 XP-002175912, Apr. 24, 2000, 1-41.
Adams, M.D., et al., "CIT-HSP-2286K19.TF CIT-HSP *Homo sapiens* genomic clone 2286K19, genomic survey sequence," AQ001459, XP-002175783, Aug. 24, 2001, 1 page.
Birren, B., et al., "*Homo sapiens* chromosome 11, clone RP11-589F4," AC027026, XP002175913, Apr. 27, 2000, 1-40.
Birren, B., et al., "*Homo sapiens* clone RP11-15H8, 31 unordered pieces," AC011780, XP002175781, Oct. 18, 1999, 1-46.
Birren, B., et al., "*Homo sapiens* clone RP11-14N15," AC016468, XP002175784, Dec. 1, 1999, 1-38.
Boyer, J.L., et al., "Molecular cloning and expression of an avian G protein-coupled P2Y receptor," *Am. Soc. For Pharmacology & Experimental Therapeutics*, XP-002175907, 1997, 928-934.
Burton, J., et al., "Human DNA sequence from clone RP11-163L4," A1161458, XP002175911, Apr. 16, 2000, 1-39.
Burton, J., "Human DNA sequence from clone RP11-15909," AL136106, XP002175785, Jan. 7, 2000.
Collier, R., "DJ68ON, 3 (G-protein coupled receptors) (fragment)," Accession Nr. Q9NTTO, XP002168498, Jan. 10, 2001, 1 page.
Doe Joint Genome Institute, "*Homo sapiens* chromosome 5 clone CTC-502M5, complete sequence," AC008547, XP002175786, Aug. 4, 1999, 1-30.
Doe Joint Genome Institute, "*Homo sapiens* chomosome 19 clone CTD-3023J11, complete sequence," AC008754, XP002175778, Aug. 4, 1999, 1-18.
Doe Joint Genome Institute, "Sequencing of human chromosome 5," AC008728, XP002175776, Aug. 4, 1999, 1-42.
Gempscpue, "*Drosophila melanogaster* genome survey sequence TET3 end of BAC # BACRO8K10 of RPCI-98 library from *Drosophila melanogaster* (fruit fly)," AL065769, XP00217590.
Hattori, M., et al., "*Homo sapiens* 171, 539 genomic of 11q13," AP000808, XP002175780, Dec. 3, 1999, 1-45.
Heise, C.E., et al., "Characterization of the human cysteinyl leukotriene 2 receptor," *J. Biological Chemistry*, Sep. 29, 2000, 275(39), 30531-30536.
Kjelsberg, M.A., et al., "constitutive activation of the $\alpha_{1B}$-adrenergic receptor by all amino acid substitutions at a single site," *J. Biological Chemistry*, XP-002135768, 1992, 265(3), 1430-1433.
Mahairas, G.G., et al., "Sequence-tagged connectors: A sequence approach to mapping and scanning the human genome," *Proc. Natl. Acad. Sci. USA*, Aug. 1999, 96, 9739-9744.
Marchese, A., et al., "Novel GPCRs and their endogenous ligands: expanding the boundaries of physiology and pharmacology," *TiPS*, Sep. 1999, 20, 370-375.
O'Dowd, B.F., et al., "Discovery of three novel G-protein-coupled receptor genes," *Genomics*, XP-000863786, 1998, 310-313.

Ohono, M., et al., "Homo spiens mRNA for G proteine-coupled receptor C5L2, complete cds," AB038237, XP002175947, May 4, 2000, 1 page.

Stadel, J.M., et al., "Orphan G protein-coupled receptors: a neglected opportunity for pioneer drug discovery," *TiPS*, Nov. 1997, 18, 430-437.

Stone, N., et al., "*Homo sapiens* chromosome 4, 16 unordered pieces," AC007104, XP002175914, Apr. 23, 1999, 1-52.

Wallis, J., "Human DNA sequence from clone RP5-1160K1," AL355310, XP002175782, May 5, 2000, 1-39.

Waterson, R.H., "*Homo sapiens* chromosome 2 clone RP11-510c1," AC010984, XP002175915, Sep. 29, 1999, 1-50.

Weinshank, R.H., "5-hydroxytryptamine 1B receptor (-HT-1B) (serotonin receptor)," AC 008892, XP002175948, Jul. 15, 1998, 1 page.

Zhao, S., et al., "Use of BAC end sequences from library RPCI-11 for sequence-ready map building," AQ532303, XP002175779, May 18, 1999, 1 page.

PCT International Search Report dated Sep. 19, 2001.

Watson, S. et al., "The G-Protein linked receptor facts book", *Academic Press*,2-6, 162-169.

Rudinger, J. et al., *Peptide Hormones*, J.A. Parsons, Unoversity Park Press, Baltimore, 1-7.

Bergsma, D.J., et al., "Cloning and characterization of a human angiotensin II type 1 receptor," *Biochem. & Biophy. Res. Comm.*, 1992, XP-002145165, 183(3), 989-995.

Gantz, I., et al., "Molecular cloning, expression, and gene localization of a fourth melanocortin receptor," *J. Biol. Chem.*, 1993, XP-002051983, 268(20), 15174-15178.

Groblewski, T., et al., "Mutation of $Asn^{111}$ in the third transmembrane domain of the $AT_{1a}$ angiotensin II receptor induces its constitutive activation," *J. Biol. Chem.*, 1997, XP-002145162, 272(3), 1822-1826.

Koike, G., et al., "Human type 2 angiotensin II receptor gene: cloned, mapped to the X chromosome, and its mRNA is expressed in the human lung," *Biochem. And Biophys. Res. Comm.*, 1994, XP-002145166, 203(3), 1842-1850.

Kyaw, H., et al., "Cloning, characterization, and mapping of human homolog of mouse T-cell death-associated gene," *DNA and Cell Biology*, 1998, XP000929737, 17(6), 493-500.

Noda, K., et al., "The active state of the $AT_1$ angiotensin receptor is generated by angiotensin II induction," *Biochem.*, 1996, XP-002145163, 35, 16435-16442.

Reppert, S.M., et al., "Cloning of a melatonin-related receptor from human pituitary," *FEBS Letts.*, 1996, XP-002145161, 219-2254.

Scheer, A., et al., "Constitutively active G protein-coupled receptors: potential mechanisms of receptor activation," *J. Receptor & Signal Transduction Res.*, 1997, XP-000867531, 17(1-3), 57-73.

* cited by examiner

Cell-Based cAMP Assay

Cell-Based cAMP Assay
basal
300nM TSH
cAMP
(pmol/mg protein)
750
500
250
0
CMV only
CMV
GPR45 wt
Co-Transfection with TSHR(A623I)

Co-Transfection with TSHR(A623I)

Northern Analysis of GPCR GPR37 expression in forskolin treated Rat Schwann cells Northern Analysis of GPCR GPR37 Expression in Crushed Rat Sciatic Nerve

Cell-specific expression of GPR66 variants in pancreatic cell lines

Expression of GPR35 in colorectal cancer cells

Co-Transfection with TSHR(A623I)

Northern Analysis of ETBR-LP2 in Forskolin Treated Rat Schwann Cells

Northern Analysis of ETBR-LP2 Expression in Crushed Rat Sciatic Nerve

Figure 20A

Alignment Report: hETBRL2p (SEQ ID NO:18) and hGRP37p (SEQ ID NO:10)

```
    M R A L G A L A A S L A V L L A V G L L K V S G G A A L G V G P A S R N E T C L  Majority
                      10                  20                  30                  40
  1 M R W L W P L A V S L A V I L A V G L S R V S G G A P L H L G - - - - - - - - - -  HETBRL2p
  1 M R A P G A L L A R M S R L L L L L L L K V S A S S A L G V A P A S R N E T C L  HGPR37p

    G E S C A P T V I Q R R G R D A W G P G N S A R D V L R A R A E T E E Q G A A F  Majority
                      50                  60                  70                  80
 32 - - - - - - - - - - - - - - - - - - - - - - - - - - - R H R A E T Q E Q Q S - -  HETBRL2p
 41 G E S C A P T V I Q R R G R D A W G P G N S A R D V L R A R A P R E E Q G A A F  HGPR37p

    L A G P S W D L P A A P G R D P A A G R G A E A S A A G P P G P P T R P P G P W  Majority
                      90                 100                 110                 120
 43 - - - - - - - - - - - - - - - - - - - - - - - - - - - - - - - - - - - - - - - -  HETBRL2p
 81 L A G P S W D L P A A P G R D P A A G R G A E A S A A G P P G P P T R P P G P W  HGPR37p

    R W K G A R G T E P S E T L G R G N P T A L Q L F L Q I S D E E A K G V Q G A G  Majority
                     130                 140                 150                 160
 43 - - R S K R G T E - - - - - - - - - - - - - - - - - - - D E E A K G V Q - - -   HETBRL2p
121 R W K G A R G Q E P S E T L G R G N P T A L Q L F L Q I S E E E E K G P R G A G  HGPR37p

    I S G R S Q E Q S V Q T V P G A S A L F Y R P I H A G G L Q G S H H K P L V A T  Majority
                     170                 180                 190                 200
 58 - - - - - - - - - - Q Y V P E E W A E Y P R P I H P A G L Q P T - - K P L V A T  HETBRL2p
161 I S G R S Q E Q S V K T V P G A S D L F Y W P R R A G K L Q G S H H K P L S K T  HGPR37p

    A N G L A G D G G W T I A L P G S G L A L N G S L G G G I H E P G G P R R G N S  Majority
                     210                 220                 230                 240
 86 S P N P D K D G G - - - - T P D S G Q E L R G N L T G A - - - P G - - - - - - -  HETBRL2p
201 A N G L A G H E G W T I A L P G R A L A Q N G S L G E G I H E P G G P R R G N S  HGPR37p

    T N Q R V Q L Q N P L Y P V T E S S Y G A Y A V M L L A V V V F G V G I V G N L  Majority
                     250                 260                 270                 280
112 - - Q R L Q I Q N P L Y P V T E S S Y S A Y A I M L L A L V V F A V G I V G N L  HETBRL2p
241 T N R R V R L K N P F Y P L T Q E S Y G A Y A V M C L S V V I F G T G I I G N L  HGPR37p

    A V M C I V W H S Y Y L K S A S N S L L A S L A L W D F L V L F F C L P L V I F  Majority
                     290                 300                 310                 320
150 S V M C I V W H S Y Y L K S A W N S I L A S L A L W D F L V L F F C L P I V I F  HETBRL2p
281 A V M C I V C H N Y Y M R S I S N S L L A N L A F W D F L I I F F C L P L V I F  HGPR37p

    N E L T K Q R L L G D V S C K A V P F I E V A S L G V T T F S L C A L G I D R F  Majority
                     330                 340                 350                 360
190 N E I T K Q R L L G D V S C R A V P F M E V S S L G V T T F S L C A L G I D R F  HETBRL2p
321 H E L T K K W L L E D F S C K I V P Y I E V A S L G V T T F T L C A L C I D R F  HGPR37p
```

Figure 20B

Alignment Report: hETBRL2p (SEQ ID NO:18) and hGRP37p (SEQ ID NO:10)

```
    HAATSVLMKVEMIENCSSILAKLAVIWVGALLLAVPEVVL Majority
              370       380       390       400
230 HVATSTLPKVRPIERCQSILAKLAVIWVGSMTLAVPELLL HETBRLP2p
361 RAATNVQMYYEMIENCSSTTAKLAVIWVGALLLALPEVVL HGPR37p

    RQLAQEDAGFSGRGTADSCIIKISASLPDSLYVLALTYDS Majority
              410       420       430       440
270 WQLAQEPA--PTMGTLDSCIMKPSASLPESLYSLVMTYQN HETBRLP2p
401 RQLSKEDLGFSGRAPAERCIIKISPDLPDTIYVLALTYDS HGPR37p

    ARLWWYFGCYFCLPILFTVTCSLVTARKVRGAPGRESACT Majority
              450       460       470       480
308 ARMWWYFGCYFCLPILFTVTCQLVT-WRVRGPPGRKSEC- HETBRLP2p
441 ARLWWYFGCYFCLPTLFTITCSLVTARKIRKA---EKACT HGPR37p

    RGSKHEIQLESQLNSTVVGLTVVYGFCILPENVCNIVVAY Majority
              490       500       510       520
346 RASKHE-QCESQLNSTVVGLTVVYAFCTLPENVCNIVVAY HETBRLP2p
478 RGNKRQIQLESQMNCTVVALTILYGFCIIPENICNIVTAY HGPR37p

    LATGVSQQTLDLLGLISQFLLFFKGAVTPVLLLCLCKPLG Majority
              530       540       550       560
385 LSTELTRQTLDLLGLINQFSTFFKGAITPVLLLCICRPLG HETBRLP2p
518 MATGVSQQTMDLLNIISQFLLFFKSCVTPVLLFCLCKPFS HGPR37p

    QAFLDCCCCCCCEECGGASSAVAADGSDNELTTEVSLSIF Majority
              570       580       590       600
425 QAFLDCCCCCCCEECGGASEASAANGSDNKLKTEVSSSIY HETBRLP2p
558 RAFMECCCCCC-EECIQKSSTVTSDDNDNEYTTELELSPF HGPR37p

    STIRRESSTLASVGTHC                        Majority
              610
465 FHKPRESPPLLPLGTPC                        HETBRLP2p
597 STIRREMSTFASVGTHC                        HGPR37p
```

Decoration 'Decoration #1': Box residues that match the Consensus exactly.

Decoration 'Decoration #2': Box residues that match the Consensus exactly.

ENDOGENOUS AND NON-ENDOGENOUS VERSIONS OF HUMAN G PROTEIN-COUPLED RECEPTORS

CROSS-REFERENCE TO RELATED APPLICATIONS

This application is a continuation-in-part of U.S. Ser. No. 09/170,496, filed on Oct. 13, 1998 (now U.S. Pat. No. 6,555,339 issued Apr. 29, 2003) and its corresponding PCT application number PCT/US99/23938, published as WO 00/22129 on Apr. 20, 2000. This application also is a continuation in part of U.S. Ser. No. 09/060,188, filed Apr. 14, 1998 which is a continuation in part of U.S. Ser. No. 08/839,449, filed Apr. 14, 1997 (abandoned). The priority benefit of each of the foregoing is claimed herein, and the disclosures of each of the foregoing is incorporated by reference herein in its entirety. This application also claims the benefit of U.S. Provisional No. 60/271,913, filed Feb. 26, 2001, also incorporated herein by reference in its entirety. This document is related to the following applications: U.S. Provisional No. 60/250,881, filed Dec. 1, 2000; U.S. Provisional No. 60/253,428, filed Nov. 27, 2000; U.S. Provisional No. 60/234,317, filed Sep. 20, 2000; U.S. Provisional No. 60/245,853, filed Nov. 3, 2000; U.S. Provisional No. 60/234,045, filed Sep. 20, 2000; U.S. Provisional No. 60/200,568, filed Apr. 28, 2000; U.S. Provisional No. 60/198,518, filed Apr. 19, 2000; U.S. Provisional No. 60/189,353, filed Mar. 14, 2000; U.S. Provisional No. 60/166,084, filed Nov. 17, 1999; and U.S. Provisional No. 60/106,451, filed Oct. 30, 1998, the disclosures of each of which are incorporated herein by reference in their entirety.

FIELD OF THE INVENTION

The present invention relates to transmembrane receptors, in some embodiments to G protein-coupled receptors and, in some preferred embodiments, to endogenous GPCRs that are altered to establish or enhance constitutive activity of the receptor. In some embodiments, the constitutively activated GPCRs will be used for the direct identification of candidate compounds as receptor agonists or inverse agonists having applicability as therapeutic agents.

BACKGROUND OF THE INVENTION

Although a number of receptor classes exist in humans, by far the most abundant and therapeutically relevant is represented by the G protein-coupled receptor (GPCR) class. It is estimated that there are some 30,000–40,000 genes within the human genome, and of these, approximately 2% are estimated to code for GPCRs. Receptors, including GPCRs, for which the endogenous ligand has been identified, are referred to as "known" receptors, while receptors for which the endogenous ligand has not been identified are referred to as "orphan" receptors.

GPCRs represent an important area for the development of pharmaceutical products: from approximately 20 of the 100 known GPCRs, approximately 60% of all prescription pharmaceuticals have been developed. For example, in 1999, of the top 100 brand name prescription drugs, the following drugs interact with GPCRs (diseases and/or disorders treated are indicated in parentheses):

| | | |
|---|---|---|
| Claritin ® (allergies) | Prozac ® (depression) | Vasotec ® (hypertension) |
| Paxil ® (depression) | Zoloft ® (depression) | Zyprexa ® (psychotic disorder) |
| Cozaar ® (hypertension) | Imitrex ® (migraine) | Zantac ® (reflux) |
| Propulsid ® (reflux disease) | Risperdal ® (schizophrenia) | Serevent ® (asthma) |
| Pepcid ® (reflux) | Gaster ® (ulcers) | Atrovent ® (bronchospasm) |
| Effexor ® (depression) | Depakote ® (epilepsy) | Cardura ® (prostatic hypertrophy) |
| Allegra ® (allergies) | Lupron ® (prostate cancer) | Zoladex ® (prostate cancer) |
| Diprivan ® (anesthesia) | BuSpar ® (anxiety) | Ventolin ® (bronchospasm) |
| Hytrin ® (hypertension) | Wellbutrin ® (depression) | Zyrtec ® (rhinitis) |
| Plavix ® (MI/stroke) | Toprol-XL ® (hypertension) | Tenormin ® (angina) |
| Xalatan ® (glaucoma) | Singulair ® (asthma) | Diovan ® (hypertension) |
| Harnal ® (prostatic hyperplasia) | | |

(Med Ad News 1999 Data).

GPCRs share a common structural motif, having seven sequences of between 22 to 24 hydrophobic amino acids that form seven alpha helices, each of which spans the membrane (each span is identified by number, i.e., transmembrane-1 (TM-1), transmebrane-2 (TM-2), etc.). The transmembrane helices are joined by strands of amino acids between transmembrane-2 and transmembrane-3, transmembrane-4 and transmembrane-5, and transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when an endogenous ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., 43 *Life Sciences* 1095 (1988). Although other G proteins exist, currently, $G_q$, $G_s$, $G_i$, $G_z$ and $G_o$ are G proteins that have been identified. Ligand-activated GPCR coupling with the G-protein initiates a signaling cascade process (referred to as "signal transduction"). Under normal conditions, signal transduction ultimately results in cellular activation or cellular inhibition. Although not wishing to be bound to theory, it is thought that the IC-3 loop as well as the carboxy terminus of the receptor interact with the G protein.

Under physiological conditions, GPCRs exist in the cell membrane in equilibrium between two different conformations: an "inactive" state and an "active" state. A receptor in an inactive state is unable to link to the intracellular signaling transduction pathway to initiate signal transduction leading to a biological response. Changing the receptor conformation to the active state allows linkage to the transduction pathway (via the G-protein) and produces a biological response.

A receptor may be stabilized in an active state by a ligand or a compound such as a drug. Recent discoveries, including but not exclusively limited to modifications to the amino acid sequence of the receptor, provide means other than ligands or drugs to promote and stabilize the receptor in the active state conformation. These means effectively stabilize the receptor in an active state by simulating the effect of a ligand binding to the receptor. Stabilization by such ligand-independent means is termed "constitutive receptor activation."

SUMMARY OF THE INVENTION

Disclosed herein are endogenous and non-endogenous versions of human GPCRs and uses thereof.

Some embodiments of the present invention relate to a G protein-coupled receptor encoded by an amino acid sequence of SEQ.ID.NO.:2, non-endogenous, constitutively activated versions of the same encoded by an amino acid of SEQ.ID.NO.:63, and host cells comprising the same.

Some embodiments of the present invention relate to a plasmid comprising a vector and the cDNA of SEQ.ID.NO.: 62 and host cells comprising the same.

Some embodiments of the present invention relate to a G protein-coupled receptor encoded by an amino acid sequence of SEQ.ID.NO.:4, non-endogenous, constitutively activated versions of the same encoded by an amino acid of SEQ.ID.NO.:65, and host cells comprising the same.

Some embodiments of the present invention relate to a plasmid comprising a vector and the cDNA of SEQ.ID.NO.: 64 and host cells comprising the same.

Some embodiments of the present invention relate to G protein-coupled receptor encoded by an amino acid sequence of SEQ.ID.NO.:6, non-endogenous, constitutively activated versions of the same, and host cells comprising the same.

Some embodiments of the present invention relate to a plasmid comprising a vector and the cDNA of SEQ.ID.NO.:5 and host cells comprising the same.

Some embodiments of the present invention relate to a G protein-coupled receptor encoded by an amino acid sequence of SEQ.ID.NO.:8, non-endogenous, constitutively activated versions of the same encoded by an amino acid of SEQ.ID.NO.:67, SEQ.ID.NO.:69, SEQ.ID.NO.:71, and SEQ.ID.NO.:73, and host cells comprising the same.

Some embodiments of the present invention relate to a plasmid comprising a vector and the cDNA of SEQ.ID.NO.: 66, SEQ.ID.NO.:68, SEQ.ID.NO.:70, and SEQ.ID.NO.:72, and host cells comprising the same.

Some embodiments of the present invention relate to a G protein-coupled receptor encoded by an amino acid sequence of SEQ.ID.NO.:10, non-endogenous, constitutively activated versions of the same encoded by an amino acid of SEQ.ID.NO.:75 and SEQ.ID.NO.:77, and host cells comprising the same.

Some embodiments of the present invention relate to a plasmid comprising a vector and the cDNA of SEQ.ID.NO.: 74 and SEQ.ID.NO.:76, and host cells comprising the same.

Some embodiments of the present invention relate to a G protein-coupled receptor encoded by an amino acid sequence of SEQ.ID.NO.:12, non-endogenous, constitutively activated versions of the same encoded by an amino acid of SEQ.ID.NO.:79 and SEQ.ID.NO.:81, and host cells comprising the same.

Some embodiments of the present invention relate to a plasmid comprising a vector and the cDNA of SEQ.ID.NO.: 78 and SEQ.ID.NO.:80, and host cells comprising the same.

Some embodiments of the present invention relate to a G protein-coupled receptor encoded by an amino acid sequence of SEQ.ID.NO.:14, constitutively activated versions of the same encoded by an amino acid of SEQ.ID.NO.: 83, and host cells comprising the same.

Some embodiments of the present invention relate to a plasmid comprising a vector and the cDNA of SEQ.ID.NO.: 82 and host cells comprising the same.

Some embodiments of the present invention relate to a G protein-coupled receptor encoded by an amino acid sequence of SEQ.ID.NO.:16, constitutively activated versions of the same encoded by an amino acid of SEQ.ID.NO.: 85, and host cells comprising the same.

Some embodiments of the present invention relate to a plasmid comprising a vector and the cDNA of SEQ.ID.NO.: 84 and host cells comprising the same.

Some embodiments of the present invention relate to a G protein-coupled receptor encoded by an amino acid sequence of SEQ.ID.NO.:18, constitutively activated versions of the same encoded by an amino acid of SEQ.ID.NO.: 87, and host cells comprising the same.

Some embodiments of the present invention relate to a plasmid comprising a vector and the cDNA of SEQ.ID.NO.: 86 and host cells comprising the same. Some embodiments of the present invention relate to a plasmid comprising a vector and the cDNA of SEQ.ID.NO.:84 and host cells comprising the same.

Some embodiments of the present invention relate to a G protein-coupled receptor encoded by an amino acid sequence of SEQ.ID.NO.:98, non-endogenous, constitutively activated versions of the same and host cells comprising the same.

Some embodiments of the present invention relate to a plasmid comprising a vector and the cDNA of SEQ.ID.NO.: 97 and host cells comprising the same.

BRIEF DESCRIPTION OF THE DRAWINGS

FIGS. 20A and 20B provides an alignment report between the putative amino acid sequence of the human ETBR-LP2 ("hETBRLP2p") and the reported amino acid sequence of human GPR37 ("hGPR37p").

DETAILED DESCRIPTION

Figure 1:
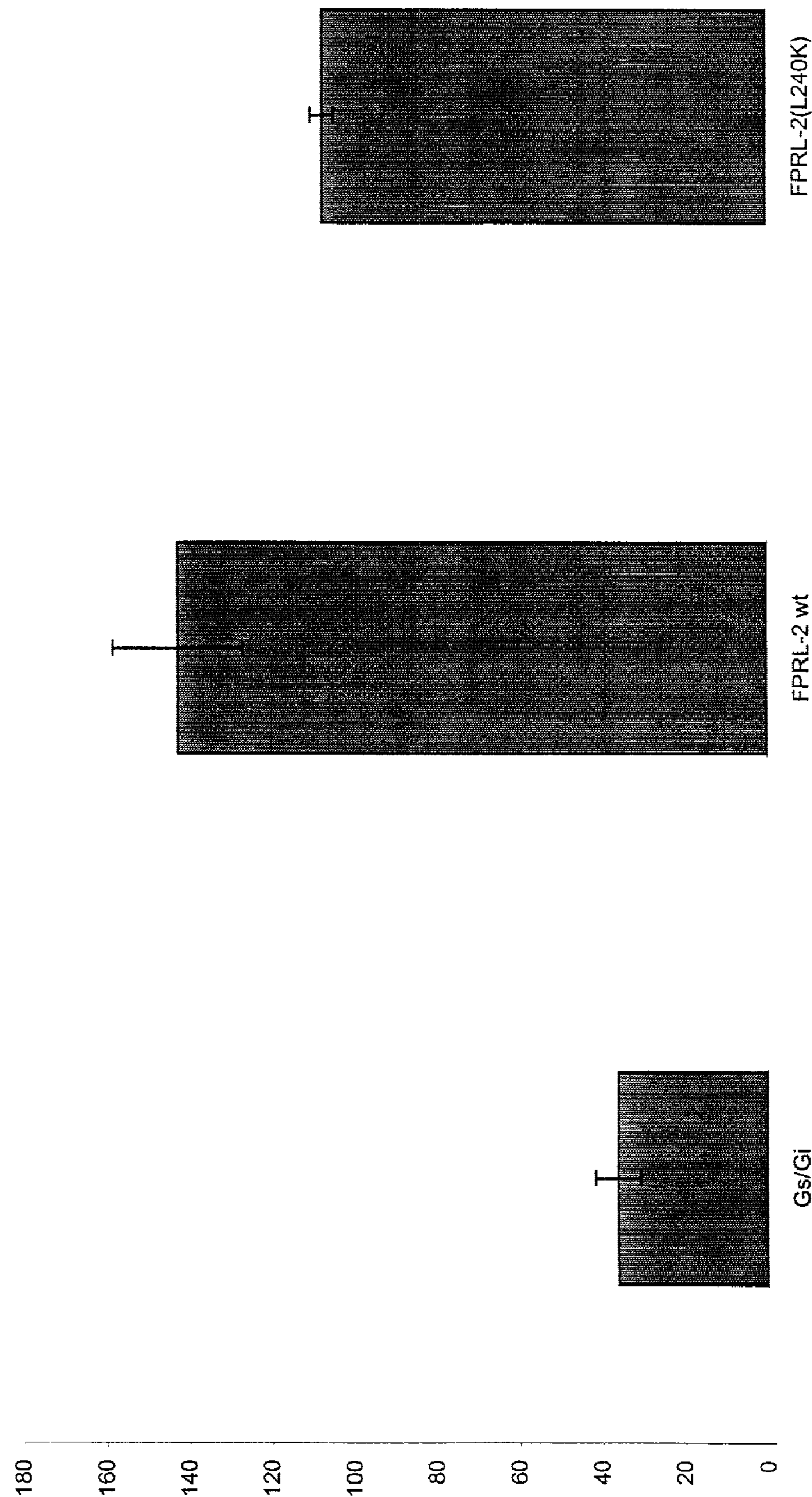
FIG. 1 is a graphic representation of the results of a second messenger cell-based cyclic AMP assay providing comparative results for constitutive signaling of endogenous, constitutively active FPRL-2 ("FPRL-2 wt"), non-endogenous, constitutively activated version of FPRL-2 ("FPRL-2 (L240K)") fused with a Gs/Gi Fusion Protein Construct and a control ("Gs/Gi").

The scientific literature that has evolved around receptors has adopted a number of terms to refer to ligands having various effects on receptors. For clarity and consistency, the following definitions will be used throughout this patent document. To the extent that these definitions conflict with other definitions for these terms, the following definitions shall control:

AGONISTS shall mean materials (e.g., ligands, candidate compounds) that activate the intracellular response when they bind to the receptor, or enhance GTP binding to membranes. In some embodiments, AGONISTS are those materials not previously known to activate the intracellular response when they bind to the receptor or to enhance GTP binding to membranes.

AMINO ACID ABBREVIATIONS used herein are set out in Table A:

TABLE A

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

ANTAGONIST shall mean materials (e.g., ligands, candidate compounds) that competitively bind to the receptor at the same site as the agonists but which do not activate the intracellular response initiated by the active form of the receptor, and can thereby inhibit the intracellular responses by agonists. ANTAGONISTS do not diminish the baseline intracellular response in the absence of an agonist. In some embodiments, ANTAGONISTS are those materials not previously known to activate the intracellular response when they bind to the receptor or to enhance GTP binding to membranes.

CANDIDATE COMPOUND shall mean a molecule (for example, and not limitation, a chemical compound) that is amenable to a screening technique. Preferably, the phrase “candidate compound” does not include compounds which were publicly known to be compounds selected from the group consisting of inverse agonist, agonist or antagonist to a receptor, as previously determined by an indirect identification process (“indirectly identified compound”); more preferably, not including an indirectly identified compound which has previously been determined to have therapeutic efficacy in at least one mammal; and, most preferably, not including an indirectly identified compound which has previously been determined to have therapeutic utility in humans.

COMPOSITION means a material comprising at least one component; a “pharmaceutical composition” is an example of a composition.

COMPOUND EFFICACY shall mean a measurement of the ability of a compound to inhibit or stimulate receptor functionality; i.e. the ability to activate/inhibit a signal transduction pathway, as opposed to receptor binding affinity. Exemplary means of detecting compound efficacy are disclosed in the Example section of this patent document.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

CONSTITUTIVELY ACTIVATED RECEPTOR shall mean a receptor subjected to constitutive receptor activation. A constitutively activated receptor can be endogenous or non-endogenous.

CONSTITUTIVE RECEPTOR ACTIVATION shall mean stabilization of a receptor in the active state by means other than binding of the receptor with its ligand or a chemical equivalent thereof.

CONTACT or CONTACTING shall mean bringing at least two moieties together, whether in an in vitro system or an in vivo system.

DIRECTLY IDENTIFYING or DIRECTLY IDENTIFIED, in relationship to the phrase “candidate compound”, shall mean the screening of a candidate compound against a constitutively activated receptor, preferably a constitutively activated orphan receptor, and most preferably against a constitutively activated G protein-coupled cell surface orphan receptor, and assessing the compound efficacy of such compound. This phrase is, under no circumstances, to be interpreted or understood to be encompassed by or to encompass the phrase “indirectly identifying” or “indirectly identified.”

ENDOGENOUS shall mean a material that a mammal naturally produces. ENDOGENOUS in reference to, for example and not limitation, the term “receptor,” shall mean that which is naturally produced by a mammal (for example, and not limitation, a human) or a virus. By contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a “non-endogenous, constitutively activated receptor.” Both terms can be utilized to describe both “in vivo” and “in vitro” systems. For example, and not limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

G PROTEIN COUPLED RECEPTOR FUSION PROTEIN and GPCR FUSION PROTEIN, in the context of the invention disclosed herein, each mean a non-endogenous protein comprising an endogenous, constitutively activate GPCR or a non-endogenous, constitutively activated GPCR fused to at least one G protein, most preferably the alpha ($\alpha$) subunit of such G protein (this being the subunit that binds GTP), with the G protein preferably being of the same type as the G protein that naturally couples with endogenous orphan GPCR. For example, and not limitation, in an endogenous state, if the G protein “$G_s\alpha$” is the predominate G protein that couples with the GPCR, a GPCR Fusion Protein based upon the specific GPCR would be a non-endogenous protein comprising the GPCR fused to $G_s\alpha$; in some circumstances, as will be set forth below, a non-predominant G protein can be fused to the GPCR. The G protein can be fused directly to the C-terminus of the constitutively active GPCR or there may be spacers between the two.

HOST CELL shall mean a cell capable of having a Plasmid and/or Vector incorporated therein. In the case of a prokaryotic Host Cell, a Plasmid is typically replicated as a autonomous molecule as the Host Cell replicates (generally, the Plasmid is thereafter isolated for introduction into a eukaryotic Host Cell); in the case of a eukaryotic Host Cell, a Plasmid is integrated into the cellular DNA of the Host Cell such that when the eukaryotic Host Cell replicates, the Plasmid replicates. In some embodiments the Host Cell is eukaryotic, more preferably, mammalian, and most preferably selected from the group consisting of 293, 293T and COS-7 cells.

INDIRECTLY IDENTIFYING or INDIRECTLY IDENTIFIED means the traditional approach to the drug discovery process involving identification of an endogenous ligand specific for an endogenous receptor, screening of candidate compounds against the receptor for determination of those which interfere and/or compete with the ligand-receptor interaction, and assessing the efficacy of the compound for affecting at least one second messenger pathway associated with the activated receptor.

INHIBIT or INHIBITING, in relationship to the term “response” shall mean that a response is decreased or prevented in the presence of a compound as opposed to in the absence of the compound.

INVERSE AGONISTS shall mean materials (e.g., ligand, candidate compound) which bind to either the endogenous form of the receptor or to the constitutively activated form of the receptor, and which inhibit the baseline intracellular response initiated by the active form of the receptor below the normal base level of activity which is observed in the absence of agonists, or decrease GTP binding to membranes. Preferably, the baseline intracellular response is inhibited in the presence of the inverse agonist by at least 30%, at least 50%, at least 60%, at least 70%, at least 75%, at least 80%, at least 85%, at least 90%, at least 92%, at least 94%, at least 95%, at least 96%, at least 97%, at least 98%, and most preferably at least 99% as compared with the baseline response in the absence of the inverse agonist.

KNOWN RECEPTOR shall mean an endogenous receptor for which the endogenous ligand specific for that receptor has been identified.

LIGAND shall mean a molecule specific for a naturally occurring receptor.

MUTANT or MUTATION in reference to an endogenous receptor's nucleic acid and/or amino acid sequence shall mean a specified change or changes to such endogenous sequences such that a mutated form of an endogenous, non-constitutively activated receptor evidences constitutive activation of the receptor. In terms of equivalents to specific sequences, a subsequent mutated form of a human receptor is considered to be equivalent to a first mutation of the human receptor if (a) the level of constitutive activation of the subsequent mutated form of a human receptor is substantially the same as that evidenced by the first mutation of the receptor; and (b) the percent sequence (amino acid and/or nucleic acid) homology between the subsequent mutated form of the receptor and the first mutation of the receptor is at least 80%, at least 85%, at least 90%, at least 92%, at least 94%, at least 95%, at least 96%, at least 97%, at least 98%, and most preferably at least 99%. In some embodiments, owing to the fact that some preferred cassettes disclosed herein for achieving constitutive activation include a single amino acid and/or codon change between the endogenous and the non-endogenous forms of the GPCR, it is preferred that the percent sequence homology should be at least 98%.

NON-ORPHAN RECEPTOR shall mean an endogenous naturally occurring molecule specific for an identified ligand wherein the binding of a ligand to a receptor activates an intracellular signaling pathway.

ORPHAN RECEPTOR shall mean an endogenous receptor for which the ligand specific for that receptor has not been identified or is not known.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

PLASMID shall mean the combination of a Vector and cDNA. Generally, a Plasmid is introduced into a Host Cell for the purposes of replication and/or expression of the cDNA as a protein.

SECOND MESSENGER shall mean an intracellular response produced as a result of receptor activation. A second messenger can include, for example, inositol triphosphate ($IP_3$), diacycglycerol (DAG), cyclic AMP (cAMP), and cyclic GMP (cGMP). Second messenger response can be measured for a determination of receptor activation. In addition, second messenger response can be measured for the direct identification of candidate compounds, including for example, inverse agonists, agonists, and antagonists.

SIGNAL TO NOISE RATIO shall mean the signal generated in response to activation, amplification, or stimulation wherein the signal is above the background noise or the basal level in response to non-activation, non-amplification, or non-stimulation.

SPACER shall mean a translated number of amino acids that are located after the last codon or last amino acid of a gene, for example a GPCR of interest, but before the start codon or beginning regions of the G protein of interest, wherein the translated number amino acids are placed in-frame with the beginnings regions of the G protein of interest. The number of translated amino acids can be tailored according to the needs of the skilled artisan and is generally from about one amino acid, preferably two amino acids, more preferably three amino acids, more preferably four amino acids, more preferably five amino acids, more preferably six amino acids, more preferably seven amino acids, more preferably eight amino acids, more preferably nine amino acids, more preferably ten amino acids, more preferably eleven amino acids, and even more preferably twelve amino acids.

STIMULATE or STIMULATING, in relationship to the term "response" shall mean that a response is increased in the presence of a compound as opposed to in the absence of the compound.

SUBSTANTIALLY shall refer to a result which is within 40% of a control result, preferably within 35%, more preferably within 30%, more preferably within 25%, more preferably within 20%, more preferably within 15%, more preferably within 10%, more preferably within 5%, more preferably within 2%, and most preferably within 1% of a control result. For example, in the context of receptor functionality, a test receptor may exhibit substantially similar results to a control receptor if the transduced signal, measured using a method taught herein or similar method known to the art-skilled, if within 40% of the signal produced by a control signal.

VECTOR in reference to cDNA shall mean a circular DNA capable of incorporating at least one cDNA and capable of incorporation into a Host Cell.

The order of the following sections is set forth for presentational efficiency and is not intended, nor should be construed, as a limitation on the disclosure or the claims to follow.

A. Introduction

The traditional study of receptors has typically proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been heretofore recognized is that it is the active state of the receptor that is most useful for discovering agonists and inverse agonists of the receptor. For those diseases which result from an overly active receptor or an under-active receptor, what is desired in a therapeutic drug is a compound which acts to diminish the active state of a receptor or enhance the activity of the receptor, respectively, not necessarily a drug which is an antagonist to the endogenous ligand. This is because a compound that reduces or enhances the activity of the active receptor state need not bind at the same site as the endogenous ligand. Thus, as taught by a method of this invention, any search for therapeutic compounds should start by screening compounds against the ligand-independent active state.

B. Identification of Human GPCRs

The efforts of the Human Genome project have led to the identification of a plethora of information regarding nucleic acid sequences located within the human genome; it has been the case in this endeavor that genetic sequence information has been made available without an understanding or recognition as to whether or not any particular genomic sequence does or may contain open-reading frame information that translate human proteins. Several methods of identifying nucleic acid sequences within the human genome are within the purview of those having ordinary skill in the art.

Receptor homology is useful in terms of gaining an appreciation of a role of the receptors within the human body. As the patent document progresses, techniques for mutating these receptors to establish non-endogenous, constitutively activated versions of these receptors will be discussed.

The techniques disclosed herein are also applicable to other human GPCRs known to the art, as will be apparent to those skilled in the art.

C. Receptor Screening

Screening candidate compounds against a non-endogenous, constitutively activated version of the GPCRs disclosed herein allows for the direct identification of candidate compounds which act at the cell surface receptor, without requiring use of the receptor's endogenous ligand. Using routine, and often commercially available techniques, one can determine areas within the body where the endogenous version of human GPCRs disclosed herein is expressed and/or over-expressed. The expression location of a receptor in a specific tissue provides a scientist with the ability to assign a physiological functional role of the receptor. It is also possible using these techniques to determine related disease/disorder states which are associated with the expression and/or over-expression of the receptor; such an approach is disclosed in this patent document. Furthermore, expression of a receptor in diseased organs can assist one in determining the magnitude of the clinical relevance of the receptor.

Constitutive activation of the GPCRs disclosed herein is based upon the distance from the proline residue at which is presumed to be located within TM6 of the GPCR; this algorithmic technique is disclosed in co-pending and commonly assigned patent document PCT Application No. PCT/US99/23938, published as WO 00/22129 on Apr. 20, 2000, which, along with the other patent documents listed herein, is incorporated herein by reference in its entirety. The algorithmic technique is not predicated upon traditional sequence "alignment" but rather a specified distance from the aforementioned TM6 proline residue (or, of course, endogenous constitutive substitution for such proline residue). By mutating an amino acid of residue located 16 amino acid residues from this residue (presumably located in the IC3 region of the receptor) to, most preferably, a lysine residue, constitutive activation of the receptor may be obtained. Other amino acid residues may be useful in the mutation at this position to achieve this objective.

D. Disease/Disorder Identification and/or Selection

As will be set forth in greater detail below, inverse agonists and agonists to the non-endogenous, constitutively activated GPCR can be identified by the methodologies of this invention. Such inverse agonists and agonists are ideal candidates as lead compounds in drug discovery programs for treating diseases related to this receptor. Because of the ability to directly identify inverse agonists to the GPCR, thereby allowing for the development of pharmaceutical compositions, a search for diseases and disorders associated with the GPCR is relevant. The expression location of a receptor in a specific tissue provides a scientist with the ability to assign a physiological function to the receptor. For example, scanning both diseased and normal tissue samples for the presence of the GPCR now becomes more than an academic exercise or one which might be pursued along the path of identifying an endogenous ligand to the specific GPCR. Tissue scans can be conducted across a broad range of healthy and diseased tissues. Such tissue scans provide a potential first step in associating a specific receptor with a disease and/or disorder. Furthermore, expression of a receptor in diseased organs can assist one in determining the magnitude of clinical relevance of the receptor. Skilled artisans, aimed with the present specification, are credited with the ability to infer the function of a GPCR once the receptor is localized to a certain tissue or region.

The DNA sequence of the GPCR can be used to make a probe/primer. In some preferred embodiments the DNA sequence is used to make a probe for (a) dot-blot analysis against tissue-mRNA, and/or (b) RT-PCR identification of the expression of the receptor in tissue samples. The presence of a receptor in a tissue source, or a diseased tissue, or the presence of the receptor at elevated concentrations in diseased tissue compared to a normal tissue, can be used to correlate location to function and indicate the receptor's physiological role/function and create a treatment regimen, including but not limited to, a disease associated with that function/role. Receptors can also be localized to regions of organs by this technique. Based on the known or assumed roles/functions of the specific tissues to which the receptor is localized, the putative physiological function of the receptor can be deduced. For example and not limitation, proteins located/expressed in areas of the thalamus are associated with sensorimotor processing and arousal (see, Goodman & Gilman's, *The Pharmacological Basis of Therapeutics,* 9$^{th}$ Edition, page 465 (1996)). Proteins expressed in the hippocampus or in Schwann cells are associated with learning and memory, and myelination of peripheral nerves, respectively (see, Kandel, E. et al., *Essentials of Neural Science and Behavior pages* 657, 680 and 28, respectively (1995)). In some embodiments, the probes and/or primers may be used to detgect and/or diagnose diseases and/or disorders, including but not limited to, those diseases and disorders identified in Example 6, infra. Methods of generating such primers and/or probes are well known to those of skill in the art as well as methods of using primers and/or probes to detect diseases and/or disorders.

E. Screening of Candidate Compounds

1. Generic GPCR Screening Assay Techniques

When a G protein receptor becomes constitutively active, it binds to a G protein (e.g., $G_q$, $G_s$, $G_i$, $G_z$, $G_o$) and stimulates the binding of GTP to the G protein. The G protein then acts as a GTPase and hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The use of this assay system is typically for initial screening of candidate compounds because the system is generically applicable to all G protein-coupled receptors regardless of the particular G protein that interacts with the intracellular domain of the receptor.

2. Specific GPCR Screening Assay Techniques

Once candidate compounds are identified using the "generic" G protein-coupled receptor assay (i.e., an assay to select compounds that are agonists or inverse agonists), further screening to confirm that the compounds have interacted at the receptor site is preferred. For example, a compound identified by the "generic" assay may not bind to the receptor, but may instead merely "uncouple" the G protein from the intracellular domain.

a. $G_s$, $G_z$ and $G_i$.

$G_s$ stimulates the enzyme adenylyl cyclase. $G_i$ (and $G_z$ and Go), on the other hand, inhibits adenylyl cyclase. Adenylyl cyclase catalyzes the conversion of ATP to cAMP; thus, constitutively activated GPCRs that couple the $G_s$ protein are associated with increased cellular levels of cAMP. On the other hand, constitutively activated GPCRs that couple $G_i$ (or $G_z$, Go) protein are associated with decreased cellular levels of cAMP. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Thus, assays that detect cAMP can be utilized to determine if a candidate compound is, e.g., an inverse agonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites (cAMP response elements) and drives the expression of the gene. Reporter systems can be constructed which have a promoter containing multiple cAMP response elements before the reporter gene, e.g., β-galactosidase or luciferase. Thus, a constitutively activated $G_s$-linked receptor causes the accumulation of cAMP that then activates the gene and leads to the expression of the reporter protein. The reporter protein such as β-galactosidase or luciferase can then be detected using standard biochemical assays (Chen et al. 1995).

b. $G_o$ and $G_q$.

$G_q$ and $G_o$ are associated with activation of the enzyme phospholipase C, which in turn hydrolyzes the phospholipid $PIP_2$, releasing two intracellular messengers: diacycloglycerol (DAG) and inositol 1,4,5-triphoisphate ($IP_3$). Increased accumulation of $IP_3$ is associated with activation of $G_q$- and Go-associated receptors. See, generally, "Indirect Mechanisms of Synaptic Transmission," Chpt. 8, *From Neuron To Brain* ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a $G_q$- or Go-associated receptor (i.e., such a compound would decrease the levels of $IP_3$). $G_q$-associated receptors can also be examined using an AP1 reporter assay wherein $G_q$-dependent phospholipase C causes activation of genes containing AP1 elements; thus, activated $G_q$-associated receptors will evidence an increase in the expression of such genes, whereby inverse agonists thereto will evidence a decrease in such expression, and agonists will evidence an increase in such expression. Commercially available assays for such detection are available.

3. GPCR Fusion Protein

The use of an endogenous, constitutively activated GPCR or a non-endogenous, constitutively activated GPCR, for use in screening of candidate compounds for the direct identification of inverse agonists, agonists provide an interesting screening challenge in that, by definition, the receptor is active even in the absence of an endogenous ligand bound thereto. Thus, in order to differentiate between, e.g., the non-endogenous receptor in the presence of a candidate compound and the non-endogenous receptor in the absence of that compound, with an aim of such a differentiation to allow for an understanding as to whether such compound may be an inverse agonist or agonist or have no affect on such a receptor, it is preferred that an approach be utilized that can enhance such differentiation. A preferred approach is the use of a GPCR Fusion Protein.

Generally, once it is determined that a non-endogenous GPCR has been constitutively activated using the assay techniques set forth above (as well as others), it is possible to determine the predominant G protein that couples with the endogenous GPCR. Coupling of the G protein to the GPCR provides a signaling pathway that can be assessed. In some embodiments it is preferred that screening take place using a mammalian expression system, such a system will be expected to have endogenous G protein therein. Thus, by definition, in such a system, the non-endogenous, constitutively activated GPCR will continuously signal. In some embodiments it is preferred that this signal be enhanced such that in the presence of, e.g., an inverse agonist to the receptor, it is more likely that it will be able to more readily differentiate, particularly in the context of screening, between the receptor when it is contacted with the inverse agonist.

The GPCR Fusion Protein is intended to enhance the efficacy of G protein coupling with the non-endogenous GPCR. The GPCR Fusion Protein is preferred for screening with either an endogenous, constitutively active GPCR or a non-endogenous, constitutively activated GPCR because such an approach increases the signal that is utilized in such screening techniques. This is important in facilitating a significant "signal to noise" ratio; such a significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. Important criteria on the construction of such a GPCR Fusion Protein construct include but are not limited to, that the endogenous GPCR sequence and the G protein sequence both be in-frame (preferably, the sequence for the endogenous GPCR is upstream of the G protein sequence), and that the "stop" codon of the GPCR be deleted or replaced such that upon expression of the GPCR, the G protein can also be expressed. Other embodiments include constructs wherein the endogenous GPCR sequence and the G protein sequence are not in-frame and/or the "stop" codon is not deleted or replaced. The GPCR can be linked directly to the G protein, or there can be spacer residues between the two preferably, no more than about 12, although this number can be readily ascertained by one of ordinary skill in the art). Based upon convenience it is preferred to use a spacer. Preferably, the G protein that couples to the non-endogenous GPCR will have been identified prior to the creation of the GPCR Fusion Protein construct. Because there are only a few G proteins that have been identified, it is preferred that a construct comprising the sequence of the G protein (i.e., a universal G protein construct (see Examples)) be available for insertion of an endogenous GPCR sequence therein; this provides for further efficiency in the context of large-scale screening of a variety of different endogenous GPCRs having different sequences.

As noted above, constitutively activated GPCRs that couple to $G_i$, $G_z$ and $G_o$ are expected to inhibit the formation of cAMP making assays based upon these types of GPCRs challenging (i.e., the cAMP signal decreases upon activation thus making the direct identification of, e.g., inverse agonists (which would further decrease this signal), challenging. As will be disclosed herein, we have ascertained that for these types of receptors, it is possible to create a GPCR Fusion Protein that is not based upon the GPCRs endogenous G protein, in an effort to establish a viable cyclase-based assay.

Thus, for example, an endogenous $G_i$ coupled receptor can be fused to a $G_s$ protein—such a fusion construct, upon expression, "drives" or "forces" the endogenous GPCR to couple with, e.g., $G_s$ rather than the "natural" $G_i$ protein, such that a cyclase-based assay can be established. Thus, for $G_i$, $G_z$ and $G_o$ coupled receptors, in some embodiments it is preferred that when a GPCR Fusion Protein is used and the assay is based upon detection of adenylyl cyclase activity, that the fusion construct be established with $G_s$ (or an equivalent G protein that stimulates the formation of the enzyme adenylyl cyclase).

| G protein | Effect of cAMP Production upon Activation of GPCR (i.e., constitutive activation or agonist binding) | Effect of $IP_3$ Accumulation upon Activation of GPCR (i.e., constitutive activation or agonist binding) | Effect of cAMP Production upon contact with an Inverse Agonist | Effect on $IP_3$ Accumulation upon contact with an Inverse Agonist |
|---|---|---|---|---|
| $G_s$ | Increase | N/A | Decrease | N/A |
| $G_i$ | Decrease | N/A | Increase | N/A |
| $G_z$ | Decrease | N/A | Increase | N/A |
| Go | Decrease | Increase | Increase | Decrease |
| $G_q$ | N/A | Increase | N/A | Decrease |

Equally effective is a G Protein Fusion construct that utilizes a $G_q$ Protein fused with a $G_s$, $G_i$, $G_z$ or $G_o$ Protein. In some embodiments a preferred fusion construct can be accomplished with a $G_q$ Protein wherein the first six (6) amino acids of the G-protein α-subunit ("Gαq") is deleted and the last five (5) amino acids at the C-terminal end of Gαq is replaced with the corresponding amino acids of the Gα of the G protein of interest. For example, a fusion construct can have a $G_q$ (6 amino acid deletion) fused with a $G_i$ Protein, resulting in a "$G_q/G_i$ Fusion Construct". This fusion construct will forces the endogenous $G_i$ coupled receptor to couple to its non-endogenous G protein, $G_q$, such that the second messenger, for example, inositol triphosphate or diacylgycerol, can be measured in lieu of cAMP production.

4. Co-transfection of a Target $G_i$ Coupled GPCR with a Signal-Enhancer $G_s$ Coupled GPCR (cAMP Based Assays)

A $G_i$ coupled receptor is known to inhibit adenylyl cyclase, and, therefore, decreases the level of cAMP production, which can make assessment of cAMP levels challenging. An effective technique in measuring the decrease in production of cAMP as an indication of constitutive activation of a receptor that predominantly couples $G_i$ upon activation can be accomplished by co-transfecting a signal enhancer, e.g., a non-endogenous, constitutively activated receptor that predominantly couples with $G_s$ upon activation (e.g., TSHR-A623I, disclosed below), with the $G_i$ linked GPCR. As is apparent, constitutive activation of a $G_s$ coupled receptor can be determined based upon an increase in production of cAMP. Constitutive activation of a $G_i$ coupled receptor leads to a decrease in production cAMP. Thus, the co-transfection approach is intended to advantageously exploit these "opposite" affects. For example, co-transfection of a non-endogenous, constitutively activated $G_s$ coupled receptor (the "signal enhancer") with the endogenous $G_i$ coupled receptor (the "target receptor") provides a baseline cAMP signal (i.e., although the $G_i$ coupled receptor will decrease cAMP levels, this "decrease" will be relative to the substantial increase in cAMP levels established by constitutively activated $G_s$ coupled signal enhancer). By then co-transfecting the signal enhancer with a constitutively activated version of the target receptor, cAMP would be expected to further decrease (relative to base line) due to the increased functional activity of the $G_i$ target (i.e., which decreases cAMP).

Screening of candidate compounds using a cAMP based assay can then be accomplished, with two 'changes' relative to the use of the endogenous receptor/G-protein fusion: first, relative to the $G_i$ coupled target receptor, "opposite" effects will result, i.e., an inverse agonist of the $G_i$ coupled target receptor will increase the measured cAMP signal, while an agonist of the $G_i$ coupled target receptor will decrease this signal; second, as would be apparent, candidate compounds that are directly identified using this approach should be assessed independently to ensure that these do not target the signal enhancing receptor (this can be done prior to or after screening against the co-transfected receptors).

F. Medicinal Chemistry

Generally, but not always, direct identification of candidate compounds is conducted in conjunction with compounds generated via combinatorial chemistry techniques, whereby thousands of compounds are randomly prepared for such analysis. Generally, the results of such screening will be compounds having unique core structures; thereafter, these compounds may be subjected to additional chemical modification around a preferred core structure(s) to further enhance the medicinal properties thereof. Such techniques are known to those in the art and will not be addressed in detail in this patent document.

G. Pharmaceutical Compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, $16^{th}$ Edition, 1980, Mack Publishing Co., (Osol et al., eds.).

H. Other Utilities

Although a preferred use of the non-endogenous versions of the GPCRs disclosed herein may be for the direct identification of candidate compounds as inverse agonists or agonists (preferably for use as pharmaceutical agents), other uses of these versions of GPCRs exist. For example, in vitro and in vivo systems incorporating GPCRs can be utilized to further elucidate and understand the roles these receptors play in the human condition, both normal and diseased, as well as understanding the role of constitutive activation as it applies to understanding the signaling cascade. In some embodiments it is preferred that the endogenous receptors be "orphan receptors", i.e., the endogenous ligand for the receptor has not been identified. In some embodiments, therefore, the modified, non-endogenous GPCRs can be used to understand the role of endogenous receptors in the human body before the endogenous ligand therefore is identified. Such receptors can also be used to further elucidate known receptors and the pathways through which they transduce a signal. Other uses of the disclosed receptors will become apparent to those in the art based upon, inter alia, a review of this patent document.

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. The traditional approach to application or understanding of sequence cassettes from one sequence to another (e.g. from rat receptor to human receptor or from human receptor A to human receptor B) is generally predicated upon sequence alignment techniques whereby the sequences are aligned in an effort to determine areas of commonality. The mutational approach disclosed herein does not rely upon this approach but is instead based upon an algorithmic approach and a positional distance from a conserved proline residue located within the TM6 region of human GPCRs. Once this approach is secured, those in the art arc credited with the ability to make minor modifications thereto to achieve substantially the same results (i.e., constitutive activation) disclosed herein. Such modified approaches are considered within the purview of this disclosure.

Example 1

Endogenous Human GPCRs

The following cDNA receptors were cloned by utilizing the techniques in this Section, see below. Table B lists the receptors disclosed throughout this patent applications, the open reading frame, the nucleic acid and the amino acid sequences for the endogenous GPCR (Table B).

TABLE B

| Disclosed Human GPCRS | Open Reading Frame (Base Pairs) | Nucleic Acid SEQ. ID. NO. | Amino Acid SEQ. ID. NO. |
|---|---|---|---|
| FPRL-2 | 1,062 bp | 1 | 2 |
| STLR33 | 1,029 bp | 3 | 4 |
| GPR45 | 1,119 bp | 5 | 6 |
| mGluR7 | 2,748 bp | 7 | 8 |
| GPR37 | 1,842 bp | 9 | 10 |
| HF1948 | 1,086 bp | 11 | 12 |
| GPR66 | 957 bp | 13 | 14 |
| GPR35 | 930 bp | 15 | 16 |
| ETBR-LP2 | 1,446 bp | 17 | 18 |
| GPR26 | 1,011 | 97 | 98 |

2. Full Length Cloning Protocol a. FPRL-2 (Seq. Id. Nos. 1 & 2)

FPRL-2 was cloned and sequenced in 1992. Bao, L. et al., 13(2) *Genomics* 437–40 (1992). FPRL-2 has been reported to be located on chromosome 19 having a sequence similarity to N-formyl peptide receptor like-1 (FPRL-1) both of which share significant similarity with the N-formyl peptide receptor (FPR). The endogenous ligand for FPR is formyl peptide, however, the two homologues of FPR, FPRL-1 and FPRL-2, do not bind to the same ligand but are likely chemotactic receptors. 13(2) *Genomics* 437–40 (1992). Chemotactic receptors are reported to be involved in inflammation. FPRL-2 is a GPCR having an open reading frame of 1062 bp encoding a 353 amino acid protein.

PCR was performed using genomic cDNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 64° C. for 1 min 20 sec and 72 C for 2 min. The 5' PCR contained an EcoRI site with the following sequence 5'-AAAGATTCAGGTGTGGGAAGATGGAAACC-3' (SEQ.ID.NO.:19) and the 3' primer contained an ApaI site with the following sequence:

5'-AAAGGATCCCCGACCTCACATTGCTTGTA-3' (SEQ.ID.NO.:20).

The PCR fragment was digested with EcoRI and ApaI and cloned into an EcoRI-ApaI site of CMV expression vector. Nucleic acid (SEQ.ID.NO.:1) and amino acid (SEQ.ID.NO.:2) sequences for human FPRL-2 were thereafter determined and verified.

b. STLR33 (Seq. Id. Nos. 3 & 4)

PCR was performed using genomic cDNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 62° C. for 1 min 20 sec and 72° C. for 2 min. The 5' PCR contained an EcoRI site with the following sequence 5'-CAGGAATTCATCAGAACAGACACCATGGCA-3' (SEQ.ID.NO.:21) and the 3' primer contained a BamHI site with the following sequence:

5'-GCAGGATCCAGAGCAGTTTTTCGAAACCCT-3' (SEQ.ID.NO.:22).

The PCR fragment was digested with EcoRI and BamHI and cloned into an EcoRI-BamHI site of CMV expression vector. Nucleic acid (SEQ.ID.NO.:3) and amino acid (SEQ.ID.NO.:4) sequences for human STRL33 were thereafter determined and verified.

c. GPR45 (Seq. Id. Nos. 5 & 6)

PCR was performed using genomic cDNA as template and rTth polymerase (Perkin Elmer) with the buffer system provided by the manufacturer, 0.25 μM of each primer, and 0.2 mM of each 4 nucleotides. The cycle condition was as follows with cylces 2 through four repeated 35 times: 96° C. for 2 min, 96° C. for 30 sec, 55° C. for 20 sec. 72° C. for 1 min and 20 sec, and 72° C. for 5 min. The 5' PCR contained a HindIII site with the following sequence 5'-TCCAAGCTTCAAGGGTCTCTCCACGATGGCCTG-3' (SEQ.ID.NO.:23) and the 3' primer contained an EcoRI site with the following sequence:

5'-TGCGAATTCTCTGTGGCCCCCTGACCCCCTAAA-3' (SEQ.ID.NO.:24).

The PCR fragment was digested with HindIII and EcoRI and cloned into a HindIII-EcoRI site of CMV expression vector. Nucleic acid (SEQ.ID.NO.:5) and amino acid (SEQ.ID.NO.:6) sequences for human GPR45 were thereafter determined and verified.

The cDNA was then tagged with V5 by resubcloning into V5-His vector using pfu PCR and the following two primers utilized had the following sequence:

```
                                    (SEQ.ID.NO.:25)
5'-GGTAAGCTTACCATGGCCTGCAACAGCACGTCCCTT-3' and

                                    (SEQ.ID.NO.:26)
5'-GACGAATTCAACCGCAGACTGGTTTTCATTGCA-3'.
```

The cycle condition was 30 cycles of 94° C. for 1 min, 60° C. for 2min and 72° C. for 2 min.

d. mGLUR7 (Seq. Id. Nos. 7 & 8)

Glutamate is an excitatory neurotransmitter which is abundantly found in the mammalian brain. See, Dingledine, R. et al., 130(4S Suppl) J Nutr. 1039S (2000). There are two classes of glutamate receptor, the ionotropic (ligand-gated ion channels) and the metabotropic (GPCRs). Metabotropic glutamate receptors are a heterogenous family of GPCRs that are linked to several second messenger pathways to regulate neuronal excitability and synaptic transmission.

(See, Phillips, T. et al., 57(1) Brain Res Mol Brain Res 132 (1998)). Metabotropic glutamate receptor type 7 (mGluR7) has been reported to be expressed in the brain, with highest levels of expression found in the hippocampus, cerebral cortex and cerebellum. See, Makoff, A. et al., 40(1) Brain Res Mol Brain Res 165 (1996). Based on the areas of the brain in which the receptor is localized, the putative functional role of the receptor can be deduced. For example, and while not wishing to be bound by any particular theory, mGluR7 is thought to play a role in depression, anxiety, obesity, Alzheimer's Disease, pain and stroke.

mGluR7 cDNA was generously supplied by Elizabeth Hoffman, Ph.D. The vector utilized for mGluR7 was pRc-CMV (the coding region for mGluR7 was subcloned into pCMV vector at an EcoRI-ClaI site). See, SEQ.ID.NO.:7 for nucleic acid sequence and SEQ.ID.NO.:8 for the deduced amino acid sequence of mGluR7.

e. GPR37 (Seq. Id. Nos. 9 & 10)

The present invention also relates to the human GPR37. GPR37 was cloned and sequenced in 1997. Marazziti, D. et al., 45 (1) Genomics 68–77 (1997). GPR37 is an orphan GPCR having an open reading frame of 1839 bp encoding a 613 amino acid protein. GPR37 has been reported to share homology with the endothelin type B-like receptor and expressed in the human brain tissues, particularly in corpus callosum, medulla, putamen, and caudate nucleus.

PCR was performed using brain cDNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 62° C. for 1 min and 72° C. for 2 min. The 5' PCR contained a HindIII site with the following sequence 5'-GCAAGCTTGTGCCCTCACCAAGCCATGCGAGCC-3' (SEQ.ID.NO.:27) and the 3' primer contained an EcoRI site with the following sequence:

5'-CGGAATTCAGCAATGAGTTCCGACAGAAGC-3' (SEQ.ID.NO.:28).

The 1.9 kb PCR fragment was digested with HindIII and EcoRI and cloned into a HindIII-EcoRI site of CMVp expression vector. Nucleic acid (SEQ.ID.NO.:9) and amino acid (SEQ.ID.NO.:10) sequences for human GPR37 were thereafter determined and verified.

f. HF1948 (Seq. Id. Nos. 11 & 12)

HF1948 cDNA was generously supplied by Elizabeth Hoffman, Ph.D. The vector utilized for HF1948 was pRc-CMV (the coding region for HF1948 was subcloned into pCMV vector at an HindIII-BamHI site). See, SEQ.ID.NO.: 11 for nucleic acid sequence and SEQ.ID.NO.:12 for the deduced amino acid sequence of HF1948.

g. GPR66 (Seq. Id. Nos. 13 & 14)

The cDNA for human GPR66 (GenBank Accession Numbers AF044600 and AF044601) was generated and cloned into pCMV expression vector as follows: PCR was performed using genomic DNA as template and TaqPlus Precision polymerase (Stratagene) for first round PCR or pfu polymerase (Stratagene) for second round PCR with the buffer system provided by the manufacturer, 0.25 μM of each primer, and 0.2 mM (TaqPlus Precision) or 0.5 mM (pfu) of each of the 4 nucleotides. When pfu was used, 10% DMSO was included in the buffer. The cycle condition was 30 cycles of: 94° C. for 1 min; 65° C. for 1 min; and 72° C. for: (a) 1 min for first round PCR; and (b) 2 min for second round PCR. Because there is an intron in the coding region, two sets of primers were separately used to generate overlapping 5' and 3' fragments. The 5' fragment PCR primers were:

```
5'-ACCATGGCTTGCAATGGCAGTGCGGCCAGGGGGCACT-3'
(external sense) (SEQ. ID. NO.:29) and

5'-CGACCAGGACAAACAGCATCTTGGTCACTTGTCTCCGGC-3'
(internal antisense) (SEQ. ID. NO.:30).
```

The 3' fragment PCR primers were:

```
5'-GACCAAGATGCTGTTTGTCCTGGTCGTGGTGTTTGGCAT-3'
(internal sense) (SEQ. ID.NO.:31) and

5'-CGGAATTCAGGATGGATCGGTCTCTTGCTGCGCCT-3' (external
antisense with an EcoRI site) (SEQ. ID. NO.:32).
```

The 5' and 3' fragments were ligated together by using the first round PCR as template and the kinased external sense primer and external antisense primer to perform second round PCR. The 1.2 kb PCR fragment was digested with EcoRI and cloned into the blunt-EcoRI site of pCMV expression vector, Nucleic acid (SEQ.ID.NO.:13) and amino acid (SEQ.ID.NO.:14) sequences for human GPR66 were thereafter determined and verified.

h. GPR35 (Seq. Id. Nos. 15 & 16)

GPR35 is a 309 amino acid sequence whereby the endogenous ligand for GPR35 is unknown (O'Dowd B. et al., 47(2) Genomics 310 (1998)). GPR35 was determined to interact with a specific transcription factor, known as E2F, which is necessary for initiating DNA replication and, ultimately, cell proliferation. Within a cell, E2F couples to a tumor suppressor gene, known as retino-blastoma ("Rb"). Upon phosphorylation of this transcription factor construct, E2F is liberated from the Rb gene and then enters the nucleus of the cell. Inside the nucleus, E2F binds to genes, such as DNA polymerase, to initiate DNA replication, which results in proliferation of the cell.

PCR was performed using genomic DNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 62° C. for 1 min and 72 ° C. for 1 min and 20 sec. The 5' PCR primer was kinased with the following sequence:

5'-GCGAATTCCGGCTCCCTGTGCTGCCCCAGG-3' (SEQ.ID.NO.:33) and the 3' primer contains a BamHI site with the following sequence:

5'-GCGGATCCCGGAGCCCCCGAGACCTGGCCC-3' (SEQ.ID.NO.:34).

The 1 kb PCR fragment was digested with BamHI and cloned into EcoRV-BamHI site of CMVp expression vector. All 6 clones sequenced contain a potential polymorphism involving change of amino acid 294 from Arg to Ser. Nucleic acid (SEQ.ID.NO.:15) and amino acid (SEQ.ID.NO.:16) sequences for human GPR35 were thereafter determined and verified.

i. ETBR-LP2 (Seq. Id. Nos. 17 & 18)

ETBR-LP2 was cloned and sequenced in 1998. Valdenaire O. et al., 424(3) *FEBS Lett.* 193 (1998); see FIG. 1 of Valdenaire for deduced nucleic and amino acid sequences. ETBR-LP2 has an open reading frame of 1839 bp encoding a 613 amino acid protein. ETBR-LP2 has been reported to share homology with the endothelin type B receptor (ETBR-LP). Further, ETBR-LP2 evidences about a 47% amino acid sequence homology with human GPR37. ETBR-LP2 has been reported to be expressed in the human central nervous system (e.g., cerebral cortex, internal capsule fibers and Bergmann glia (424 *FEBS Lett* at 196).

PCR was performed using brain cDNA as template and rTth polymerase (Perkin Elmer) with the buffer system provided by the manufacturer, 0.25 μM of each primer, and 0.2 mM of each 4 nucleotides. The cycle condition was 30 cycles of 94° C. for 1 min, 65° C. for 1 min and 72° C. for 1.5 min. The 5' PCR contained an EcoRI site with the sequence:

5'-CTGGAATTCTCCTGCTCATCCAGCCATGCGG-3' (SEQ.ID.NO.:35) and the 3' primer contained a BamHI site with the sequence:

5'-CCTGGATCCCCACCCCTACTGGGGCCTCAG-3' (SEQ.ID.NO.:36).

The resulting 1.5 kb PCR fragment was digested with EcoRI and BamHI and cloned into EcoRI-BamHI site of pCMV expression vector. Nucleic acid (SEQ.ID.NO.:17) and amino acid (SEQ.ID.NO.:18) sequences for human ETBR-LP2 were thereafter determined and verified.

j. GPR26 (Seq. Id. Nos. 97 & 98)

EST clone HIBB055, a 3' 400 bp PCR fragment used to screen the Human Genomic lambda Dash II Library (Stratagene catalog special order). The screening conditions were as follows: filters were hybridize overnight at 55° C. in a formamide based hybridization solution. The washing conditions were 2× SSC/1% SDS twice at 65° and 0.2× SSC/0.1% SDS twice at 65° C. for 20min at each wash. The filters were placed on film exposed overnight at −80° C. and developed the next day. The positive plaques were further characterized by a second round of phage screening from the primary plugs under the same conditions.

Human Fetal Brain cDNA library Uni-ZAP XR Vector (catalog#937227, Stratagene) was then probed with a 250 bp probe generated from new sequence from the genomic library screening. The 250 bp probe was generated by PCR with Taqplus Precision PCR system (Stratagene #600210) with manufacturer supplied buffer system. The cycling parameters were as follows: 30 cycles with 95° C. for 45 sec, 55° C. for 40 sec, 72° C. for 1 min and final extension for 10 min. The primers utilized were as follows:

```
                                    (SEQ.ID.NO.:99)
5'-CGAGAAGGTGCTCAAGGTGGC-3'              and

                                    (SEQ.ID.NO.:100)
5'-GAGAAGAGCTCCACTAGCCTGGTGATCACA-3'.
```

The Human Fetal Brain cDNA library was probed with the same 250 bp PCR fragment under the same conditions as the genomic library except the hybridization temp was 42° C. The positive primary plugs were further characterized by a second round of screening under the same conditions with a hybridization temp. of 55° C. Positive plaques were analyzed by sequence via Sanger method and the start codon was obtained from one of the positive clones The human GPR26 full length clone was then generated by PCR using PfuTurbo DNA Polymerase (Stratagene #600250) with the following parameters:

40 cycles of 95° C. for 45 sec., 62° C. for 1 min. and 72° C. for 1.2 min. and a final extension of 10 min. at 72° C. The template used was Human Fetal Brain cDNA (Clonetech# 7402-1) and the primers were as follows:

```
                                         (SEQ.ID.NO.:101)
5'-GAATTCATGAACTCGTGGGACGCGGGCCTGGCGGGC-3' and

                                         (SEQ.ID.NO.:102)
5'-CTCGAGTCACTCAGACACCGGCAGAATGTTCT-3'.
```

The fragment generated had a 5' EcoR1 linker and a 3' Xho1 linker. The PCR product was digested using the given linker enzymes and subcloned into the expression vector pcDNA3.1(+) (Invitrogen#V790-20) at the EcoR1/Xho1 sites using the Rapid Ligation Kit (Roche#1635 379). Nucleic acid (SEQ.ID.NO.:97) and amino acid (SEQ.ID.NO.:98) sequences for human GPR26 were thereafter determined and verified.

Example 2

Preparation of Non-Endogenous, Constitutively Activated GPCRs

Those skilled in the art are credited with the ability to select techniques for mutation of a nucleic acid sequence. Presented below are approaches utilized to create non-endogenous versions of several of the human GPCRs disclosed above. The mutations disclosed below are based upon an algorithmic approach whereby the 16$^{th}$ amino acid (located in the IC3 region of the GPCR) from a conserved proline (or an endogenous, conservative substitution therefore) residue (located in the TM6 region of the GPCR, near the TM6/IC3 interface) is mutated, preferably to an alanine, histimine, arginine or lysine amino acid residue, most preferably to a lysine amino acid residue.

1. Site-Directed Mutagenesis

Preparation of non-endogenous human GPCRs was accomplished on human GPCRs using, inter alia, Transformer Site-Directed™ Mutagenesis Kit (Clontech) according to the manufacturer instructions or QuikChange™ Site-Directed™ Mutagenesis Kit (Stratagene, according to manufacturer's instructions). The following GPCRs were mutated according with the above method using the designated sequence primers (Table C). For convenience, the codon mutation to be incorporated into the human GPCR is also noted, in standard form (Table C):

TABLE C

| Receptor Identifier | Codon Mutation | 5'-3' orientation, mutation sequence underlined (SEQ.ID.NO.) | 5'-3'orientation (SEQ.ID.NO.) |
|---|---|---|---|
| ELPR-2 | T240K | TCCAGCCGTCCC<u>AAA</u>CGT GTCTTCGCTGC (37) | CTCCTTCGGTCCTCCTA TCGTTGTCAGAAGT (38) |

TABLE C-continued

| Receptor Identifier | Codon Mutation | 5'-3' orientation, mutation sequence underlined (SEQ.ID.NO.) | 5'-3'orientation (SEQ.ID.NO.) |
|---|---|---|---|
| STRL33 | L230K | CAGAAGCACAGATCAAAAAAGATCATCTTCCTG (39) | CTCCTTCGGTCCTCCTATCGTTGTCAGAAGT (38) |
| mGIuR7 | W590S | AGTGGCACTCCCCCTCGGCTGTGATTCCTGT(59) | ACAGGAATCACAGCCGGGGGGAGTGCCACT(40) |
| | R659H | TGTGTTCTTTCCGGCATGTTTTCTTGGGCTTG (41) | CAAGCCCAAGAAAACATGCCGGAAAGAACACA (42) |
| | T771C | CTCATGGTCACATGTTGTGTGTATGCCATCAAG (43) | CTTGATGGCATACACACAACATGTGACCATGAG(44) |
| | 1790K | ACGAAGCCAAGCCCAAGGGATTCACTATGTACAC (45) | GTGTACATAGTGAATCCCTTGGGCTTGGCTCCGT(46) |
| GPR37 | L352R | GTCACCACCTTTCACCCGATGTGCTCTGTGCATAG (47) | CTATGCACAGAGCACATCGGGTGAAAGGTGGTGAC (48) |
| | C543Y | CCTTTTGTTCTTTAAGTCCTATGTCACCCCAGTCCT (49) | AGGACTGGGGTGACATAGGACTTAAAGAACAAAAGG (50) |
| H1F1948 | 1281F | ATGTGGAGCCCCATCTTCATCACCATCCTCC (51) | GGAGGATGGTGATGAAGATGGGGCTCCACAT (52) |
| | E135N | GCCGCGGTCAGCCTGAATCGCATGGTGTGCATC (53) | GATGCACACCATGCGATTCAGGCTGACCGCGGC(54) |
| GPR66 | T273K | GGCCGGAGACAAGTGAAAAGATGCTGTTT (55) | AAACAGCATCTTTTTCACTTGTCTCCGGCC (56) |
| GPR35 | A216K | See alternate approaches | See alternate approaches |
| ETBR-LP2 | N358K | GAGAGCCAGCTCAAGAGCACCGTGGTG (57) | CTCCTTCGGTCCTCCTATCGTTGTCAGAAGT (58) |

1. Alternative Approaches for Creation of Non-endogenous Human GPCRs

Preparation of the non-endogenous, constitutively activated human GPR35 receptor was accomplished by creating a A216K mutation. Mutagenesis was performed using Transformer Site-Directed™ Mutagenesis Kit (Clontech) according to manufacturer's instructions. (see, SEQ.ID.NO.:84 for nucleic acid sequence, SEQ.ID.NO.:85 for amino acid sequence). The two mutagenesis primers were utilized, a lysine mutagenesis oligonucleotide and a selection marker oligonucleotide, which had the following sequences:

```
5'-GCCACCCGCAAGGCTAAACGCATGGTCTGG-3'
(SEQ. ID. NO.:60 sense) and

5'-CTCCTTCGGTCCTCCTATCGTTGTCAGAAGT-3'
(SEQ. ID. NO.:61; antisense),
```

respectively.

For first round PCR, SEQ.ID.NO.:33 and SEQ.ID.NO.:61 were used to generate the 5' 700 bp fragment, while SEQ.ID.NO.:34 and SEQ.ID.NO.:60 were used to generate the 3' 350 bp fragment. PCR was performed using endogenous GPR35 cDNA as template and pfu polymerase (Stratagene) with the buffer system provided by the manufacturer supplemented with 10% DMSO, 0.25 μM of each primer, and 0.5 mM of each 4 nucleotides. The cycle condition was 25 cycles of 94° C. for 30 sec, 65° C. for 1 min and 72° C. for 2 min and 20 sec. The 5' and 3' PCR fragment from first round PCR were then used as cotemplate to perform second round PCR using oligo 1 and 2 as primers and pfu polymerase as described above except the annealing temperature was 55° C., and the extention time was 2 min. The resulting PCR fragment was then digested and subcloned into pCMV as described for the endogenous cDNA.

The non-endogenous human GPCRs were then sequenced and the derived and verified nucleic acid and amino acid sequences are listed in the accompanying "Sequence Listing" appendix to this patent document, as summarized in Table D below:

TABLE D

| Non-Endogenous Receptor | Nucleic Acid Sequence Listing | Amino Acid Sequence Listing |
|---|---|---|
| FPRL-2 | | |
| L240K | SEQ. ID. NO.:62 | SEQ. ID. NO.:63 |

TABLE D-continued

| Non-Endogenous Receptor | Nucleic Acid Sequence Listing | Amino Acid Sequence Listing |
|---|---|---|
| STRL33 | | |
| L230K | SEQ. ID. NO.:64 | SEQ. ID. NO.:65 |
| MgluR7 | | |
| W590S | SEQ. ID. NO.:66 | SEQ. ID. NO.:67 |
| R659H | SEQ. ID. NO.:68 | SEQ. ID. NO.:69 |
| T771C | SEQ. ID. NO.:70 | SEQ. ID. NO.:71 |
| I790K | SEQ. ID. NO.:72 | SEQ. ID. NO.:73 |
| GPR37 | | |
| L352R | SEQ. ID. NO.:74 | SEQ. ID. NO.:75 |
| C543Y | SEQ. ID. NO.:76 | SEQ. ID. NO.:77 |
| HF1948 | | |
| I281F | SEQ. ID. NO.:78 | SEQ. ID. NO.:79 |
| E135N | SEQ. ID. NO.:80 | SEQ. ID. NO.:81 |
| GPR66 | | |
| T273K | SEQ. ID. NO.:82 | SEQ. ID. NO.:83 |
| GPR35 | | |
| A216K | SEQ. ID. NO.:84 | SEQ. ID. NO.:85 |
| ETBR-LP2 | | |
| N358K | SEQ. ID. NO.:86 | SEQ. ID. NO.:87 |

Example 3

Receptor Expression

Although a variety of cells are available to the art-skilled for the expression of proteins, it is preferred that mammalian cells be utilized. The primary reason for this is predicated upon practicalities, i.e., utilization of, e.g., yeast cells for the expression of a GPCR, while possible, introduces into the protocol a non-mammalian cell which may not (indeed, in the case of yeast, does not) include the receptor-coupling, genetic-mechanism and secretary pathways that have evolved for mammalian systems—thus, results obtained in non-mammalian cells, while of potential use, are not as preferred as those obtained using mammalian cells. Of the mammalian cells, COS-7, 293 and 293T cells are particularly preferred, although the specific mammalian cell utilized can be predicated upon the particular needs of the artisan.

a. Transient Transfection of 293 Cells

On day one, $6\times10^6$ cells/10 cm dish of 293 cells well were plated out. On day two, two reaction tubes were prepared (the proportions to follow for each tube are per plate): tube A was prepared by mixing 4 μg DNA (e.g., pCMV vector; pCMV vector with receptor cDNA, etc.) in 0.5 ml serum free DMEM (Gibco BRL); tube B was prepared by mixing 24 μl lipofectamine (Gibco BRL) in 0.5 ml serum free DMEM. Tubes A and B were admixed by inversion (several times), followed by incubation at room temperature for 30–45 min. The admixture is referred to as the "transfection mixture". Plated 293 cells were washed with 1×PBS, followed by addition of 5 ml serum free DMEM. One ml of the transfection mixture were added to the cells, followed by incubation for 4 hrs at 37° C./5% $CO_2$. The transfection mixture was removed by aspiration, followed by the addition of 10 ml of DMEM/10% Fetal Bovine Serum. Cells were incubated at 37° C./5% $CO_2$. After 48 hr incubation, cells were harvested and utilized for analysis.

b. Stable 293 Cell Lines

Approximately $12\times10^6$ 293 cells will be plated on a 15 cm tissue culture plate, and grown in DME High Glucose Medium containing 10% fetal bovine serum and one percent sodium pyruvate, L-glutamine, and antibiotics. Twenty-four hours following plating of 293 cells (to approximately ~80% confluency), the cells will be transfected using 12 μg of DNA. The 12 μg of DNA is combined with 60 μl of lipofectamine and 2 mL of DME High Glucose Medium without serum. The medium will be aspirated from the plates and the cells washed once with medium without serum. The DNA, lipofectamine, and medium mixture will be added to the plate along with 10 mL of medium without serum. Following incubation at 37° C. for four to five hours, the medium will be aspirated and 25 ml of medium containing serum will be added. Twenty-four hours following transfection, the medium will be aspirated again, and fresh medium with serum will be added. Forty-eight hours following transfection, the medium will be aspirated and medium with serum will be added containing geneticin (G418 drug) at a final concentration of 500 μg/mL. The transfected cells will then undergo selection for positively transfected cells containing the G418 resistant gene. The medium will be replaced every four to five days as selection occurs. During selection, cells will be grown to create stable pools, or split for stable clonal selection.

C. RGT Cells (Used for mGluR7)

RGT cells were derived from an adenovirus transformed Syrian hamster cell line (AV12-664) into which a glutamate-aspartate transporter was stably transfected.

On day one, $5\times10^6$/10 cm dish of RGT cells were plated out. On day two, 91 μl of serumfree media was added to a tube, followed by the addition of 9 μl of Fugene 6 (Roche). To the same mix 3 ug of DNA was added (at 0.5 ug/ul). The mixture was gently mixed and incubated at room temperature for 15 min, then this mixture was added dropwise to the cells growing in DMEM/10% FBS and incubated for 48 hours at 37° C./5% $CO_2$. After 48 hr incubation, cells were harvested and utilized for analysis.

Example 4

Assays for Determination of Constitutive Activity of Non-Endogenous GPCRs

A variety of approaches are available :for assessment of constitutive activity of the non-endogenous human GPCRs. The following are illustrative; those of ordinary skill in the art are credited with the ability to determine those techniques that are preferentially beneficial for the needs of the artisan.

1. Membrane Binding Assays: [$^{35}$S]GTPγS Assay

When a G protein-coupled receptor is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyzes the GTP to GDP, at which point the receptor normally is deactivated. Constitutively activated receptors continue to exchange GDP for GTP. The non-hydrolyzable GTP analog, [$^{35}$S]GTPγS, can be utilized to demonstrate enhanced binding of [$^{35}$S]GTPγS to membranes expressing constitutively activated receptors. Advantages of using [$^{35}$S]GTPγS binding to measure constitutive activation include but are not limited to the following: (a) it is generically applicable to all G protein-coupled receptors;

(b) it is proximal at the membrane surface making it less likely to pick-up molecules which affect the intracellular cascade.

The assay takes advantage of the ability of G protein coupled receptors to stimulate [$^{35}$S]GTPγS binding to membranes expressing the relevant receptors. The assay can, therefore, be used in the direct identification method to screen candidate compounds to constitutively activated G protein-coupled receptors. The assay is generic and has application to drug discovery at all G protein-coupled receptors.

The [$^{35}$S]GTPγS assay is incubated in 20 mM HEPES and between 1 and about 20 mM $MgCl_2$ (this amount can be adjusted for optimization of results, although 20 mM is preferred) pH 7.4, binding buffer with between about 0.3 and about 1.2 nM [$^{35}$S]GTPγS (this amount can be adjusted for optimization of results, although 1.2 is preferred ) and 12.5 to 75 μg membrane protein (e.g., 293 cells expressing the $G_s$ Fusion Protein; this amount can be adjusted for optimization) and 10 μM GDP (this amount can be changed for optimization) for 1 hour. Wheatgerm agglutinin beads (25 μl; Amersham) will then be added and the mixture incubated for another 30 minutes at room temperature. The tubes will be then centrifuged at 1500×g for 5 minutes at room temperature and then counted in a scintillation counter.

2. Cell-based cAMP Detection Assay

A Flash Plate™ Adenylyl Cyclase kit (New England Nuclear; Cat. No. SMP004A) designed for cell-based assays can be modified for use with crude plasma membranes. The Flash Plate wells can contain a scintillant coating which also contains a specific antibody recognizing cAMP. The cAMP generated in the wells can be quantitated by a direct competition for binding of radioactive cAMP tracer to the cAMP antibody. The following serves as a brief protocol for the measurement of changes in cAMP levels in whole cells that express the receptors.

Transfected cells were harvested approximately twenty four hours after transient transfection. Media was carefully aspirated and discarded. Ten ml of PBS was gently added to each dish of cells followed by careful aspiration. One ml of Sigma cell dissociation buffer and 3 ml of PBS was added to each plate. Cells were pipetted off the plate and the cell suspension collected into a 50 ml conical centrifuge tube. Cells were centrifuged at room temperature at 1,100 rpm for 5 min. The cell pellet was carefully resuspended into an appropriate volume of PBS (about 3 ml/plate). The cells were then counted using a hemocytometer and additional PBS was added to give the appropriate number of cells (to a final volume of about 50 μl/well).

cAMP standards and Detection Buffer (comprising 1 μCi of tracer [$^{125}$I cAMP (50 μl] to 11 ml Detection Buffer) was prepared and maintained in accordance with the manufacturer's instructions. Assay Buffer was prepared fresh for screening and contained 50 μl of Stimulation Buffer, 3 μl of test compound (12 μM final assay concentration) and 50 μl cells, Assay Buffer was be stored on ice until utilized. The assay was initiated by addition of 50 μl of cAMP standards to appropriate wells followed by addition of 50 μl of PBSA to wells H-11 and H12. Fifty μl of Stimulation Buffer was added to all wells. DMSO (or selected candidate compounds) was added to appropriate wells using a pin tool capable of dispensing 3 μl of compound solution, with a final assay concentration of 12 μM test compound and 100 μl total assay volume. The cells were then added to the wells and incubated for 60 min at room temperature. One hundred μl of Detection Mix containing tracer cAMP was then added to the wells. Plates were incubated for an additional 2 hours followed by counting in a Wallac MicroBeta™ scintillation counter. Values of cAMP/well were then extrapolated from a standard cAMP curve which were contained within each assay plate.

3. Co-transfection of Gi Coupled FPRL-2 with a Gs/Gi Fusion Protein Construct

The transfection mixture (from Example 3A) containing FPRL-2 and Gs/Gi Fusion Protein Construct was removed by aspiration, followed by the addition of 10 ml of DMEM/10% Fetal Bovine Serum. Cells were then incubated at 37° C./5% $CO_2$. After 48 hr incubation, cells were harvested and utilized for analysis. Cell-based cAMP detection assay was then performed according to the protocol in Example 4(2) above.

Because endogenous FPRL-2 is believed to predominantly couple with the Gi protein in its active state, a decrease in cAMP production signifies that the disclosed non-endogenous version of FPRL-2 is constitutively active. Thus, a candidate compound which impacts the FPRL-2 receptor by increasing the cAMP signal is an inverse agonist, while a FPRL-2 agonist will decrease the cAMP signal. See, FIG. 1.

FIG. 1 evidence about a 4 fold increase in activity of FPRL-2 when compared to the Gs/Gi. When comparing the endogenous version of FPRL-2 with that of the non-endogenous version, the non-endogenous FPRL-2 ("FPRL-2 (L240K)")) evidence about a 3 fold increase in receptor activity when compared to the control, Gs/Gi. Therefore, this data suggests that both the endogenous and non-endogenous versions of FPRL-2 are constitutively active.

Figure 9:
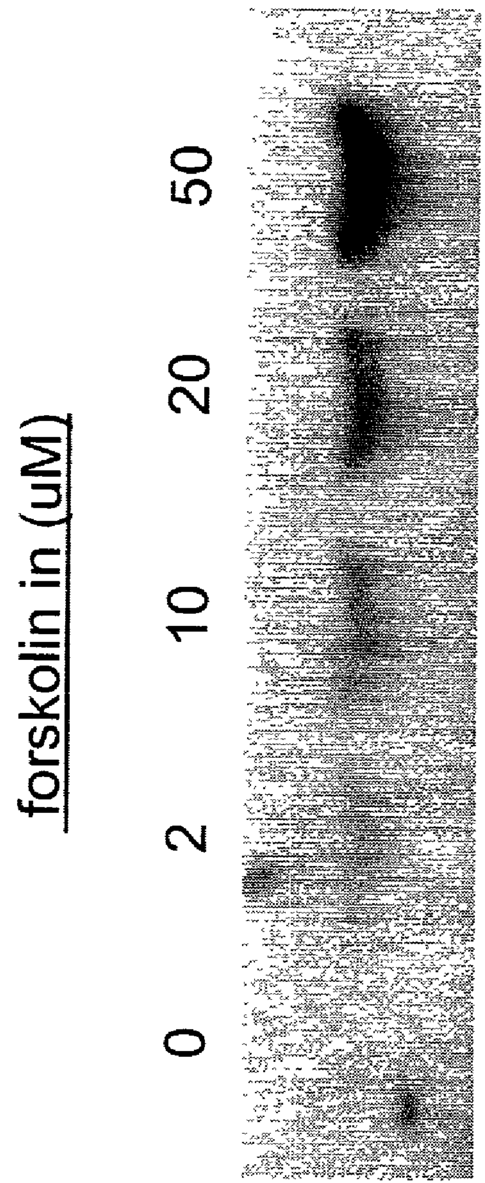
FIG. 9 is a representation of a Northern Analysis of GPR37 expressed in forskolin treated rat Schwann cells. Cell differentiation was maintained at 20 uM of forskolin.

Reference is made to FIG. 9. In FIG. 9, non-endogenous GPR37(L352R) produced about a 354% increase in cAMP when compared with the endogenous version of GPR37 ("GPR37 wt"), while GPR37(C543Y) produced about a 189% increase in cAMP when compared with GPR37 wt. This data suggests that both non-endogenous L352R and C543Y versions of GPR37 are constitutively activated.

4. Cell-based cAMP for $G_i$ Coupled Target GPCRs

TSHR is a $G_s$ coupled GPCR that causes the accumulation of cAMP upon activation. TSHR will be constitutively activated by mutating amino acid residue 623 (i.e., changing an alanine residue to an isoleucine residue). A $G_i$ coupled receptor is expected to inhibit adenylyl cyclase, and, therefore, decrease the level of cAMP production, which can make assessment of cAMP levels challenging. An effective technique for measuring the decrease in production of cAMP as an indication of constitutive activation of a $G_i$ coupled receptor can be accomplished by co-transfecting, most preferably, non-endogenous, constitutively activated TSHR (TSHR-A623I) (or an endogenous, constitutively active $G_s$ coupled receptor) as a "signal enhancer" with a $G_i$ linked target GPCR to establish a baseline level of cAMP. Upon creating a non-endogenous version of the $G_i$ coupled receptor, this non-endogenous version of the target GPCR is then co-transfected with the signal enhancer, and it is this material that can be used for screening. This approach will be utilized to effectively generate a signal when a cAMP assay is used; this approach is preferably used in the direct identification of candidate compounds against $G_i$ coupled receptors. It is noted that for a $G_i$ coupled GPCR, when this approach is used, an inverse agonist of the target GPCR will increase the cAMP signal and an agonist will decrease the cAMP signal.

Cells were transfected according to Example 3A above. The transfected cells were then transfected cells will be harvested approximately twenty four hours after transient transfection. Cell-based cAMP detection assay was then performed according to the protocol in Example 4(2) above.

Preferably, and as noted previously, to ensure that a small molecule candidate compound is targeting the $G_i$ coupled target receptor and not, for example, the TSHR(A623I), the directly identified candidate compound is preferably screened against the signal enhancer in the absence of the target receptor.

Figure 3:
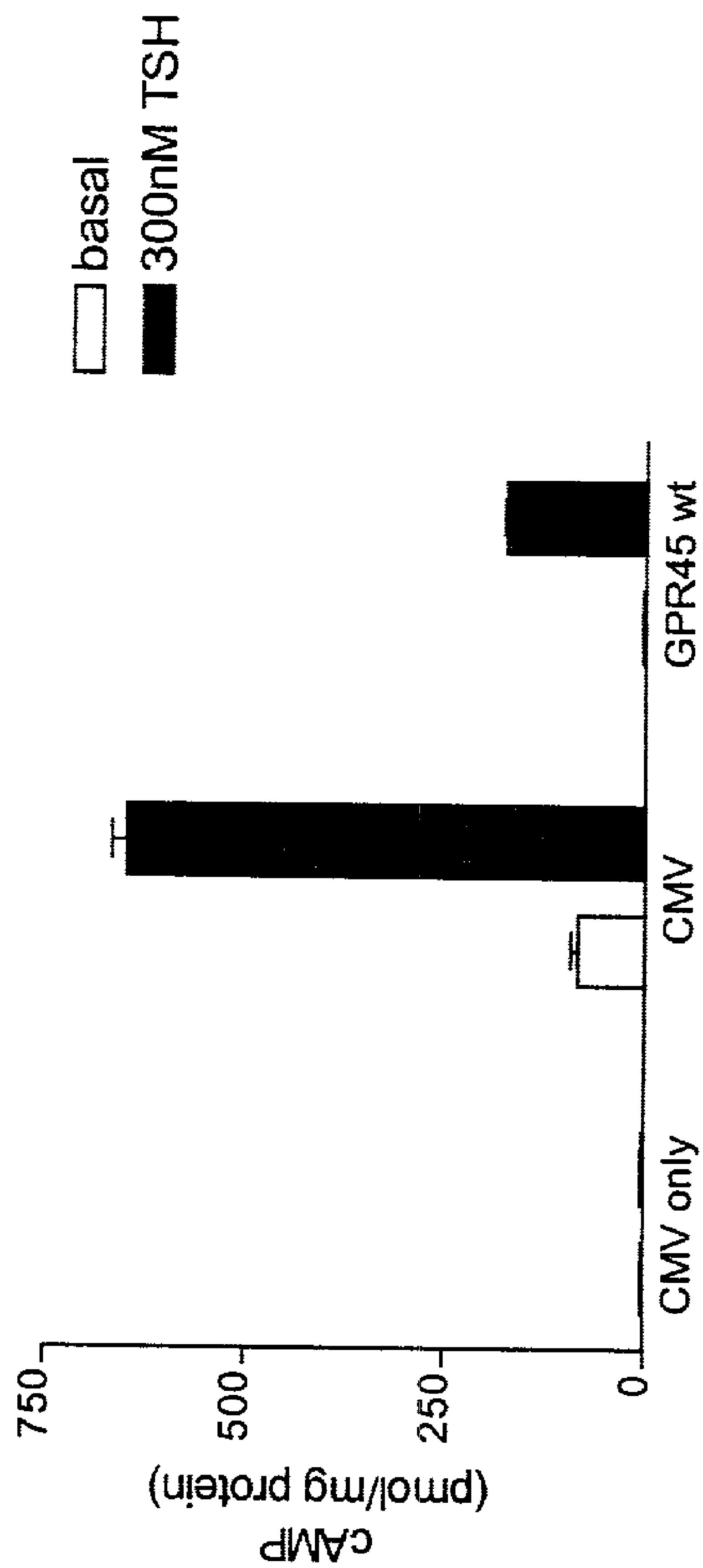
FIG. 3 provides graphic results of comparative analysis of a co-transfection of non-endogenous TSHR(A623I) ("signal enhancer") with an endogenous target receptor, in this case GPR45 ("GPR45 wt"), versus a control ("CMV"), utilizing a cell-based adenylyl cyclase assay in 293 cells. This assay involved the addition of TSH, the endogenous ligand for TSHR.

Reference is made to FIG. 3. FIG. 3 is a comparative analysis of endogenous GPR45 ("GPR45 wt") versus a control ("CMV") in 293 cells. Endogenous target receptor GPR45 was co-transfected with a signal enhancer, TSHR (A623I). In the absence of TSH, the endogenous ligand for TSH receptor, co-transfection of TSHR(A623I) with endogenous GPR45 evidence about a 96% decrease in production of cAMP when compared with the control (CMV). In the presence of TSH, endogenous GPR45 ("GPR45 wt") evidence about a 73% decrease in cAMP production when compared to the control ("CMV"). This data indicates that GPR45 is endogenously constitutively active and couples through the Gi protein.

Figure 4:
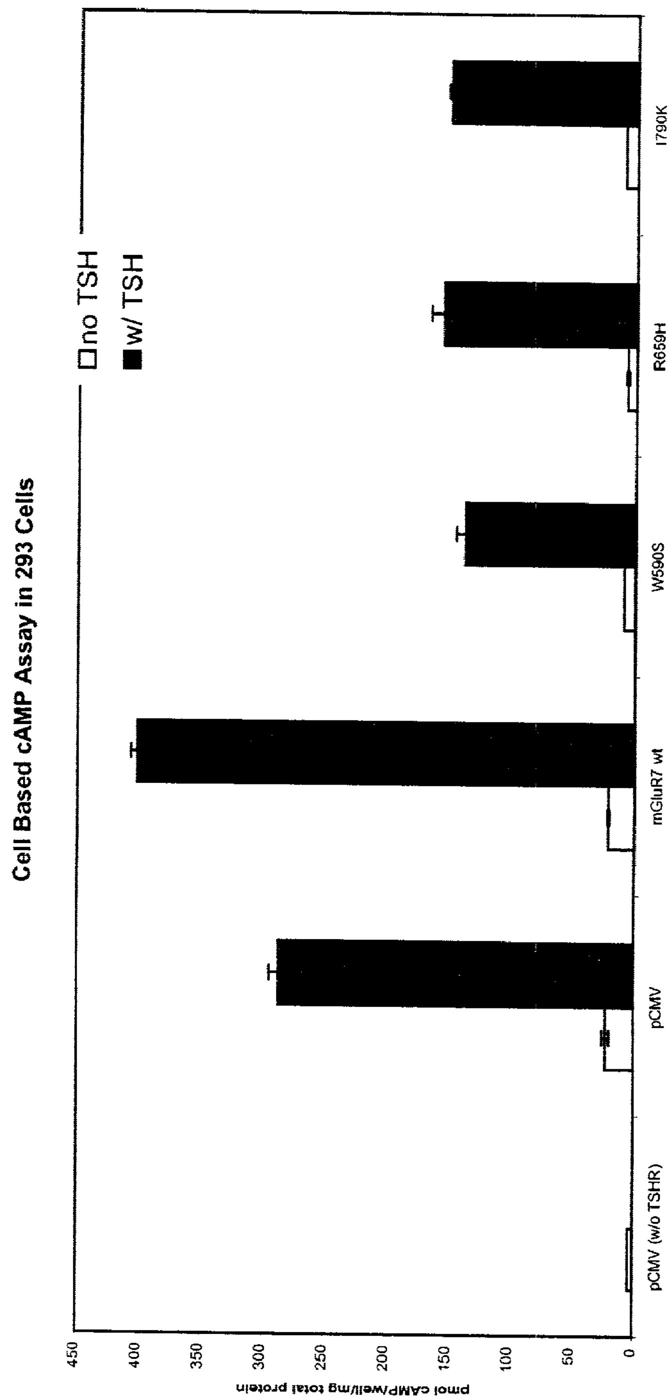
FIG. 4 provides graphic results of comparative analysis of a co-transfection of non-endogenous TSHR(A623I) ("signal enhancer") and an endogenous target receptor, in this case mGluR7 ("mGluR7 wt"), versus non-endogenous, constitutively activated versions of the target receptor mGluR7 ("W590S," "R659H" "T771C" and "I790K") co-transfected with non-endogenous TSHR(A623I), utilizing a cell-based adenylyl cyclase assay in 293 cells. This assay involved the addition of TSH, the endogenous ligand for TSHR.

Reference is made to FIG. 4 and Table E. Table E is a summary of FIG. 4, which is a comparative analysis of endogenous mGluR7 ("mGluR7 wt") with several non-endogenous versions of mGluR7 ("W590S," "R659H," "T771C" and "I790K") and the control ("pCMV") in 293 cells. Table E summarizes the cAMP production of the vector containing the signal enhancer receptor (i.e., TSHR (A623I)) with the target receptor (mGluR7) in the absence of its endogenous ligand (i.e., TSH); the cAMP production of the co-transfection of the signal enhancer with the target receptor in the presence of TSH percent (%) decrease, in cAMP production, between the endogenous version of mGluR7 and the non-endogenous versions of mGluR7, co-transfected with TSHR(A623I) in the presence of TSH. This data evidences that the non-endogenous versions of mGluR7 ("W590S," "R659H," "T771C" and "I790K") reduce the production of cAMP when compared to the endogenous mGluR7, and thus has been constitutively activated by the methods disclosed above.

TABLE E

| Versions of mGluR7 | Co-Transfection of 1) Vector-TSHR(A623I) 2) mGluR7 versions 3) without 16 mU/ml TSH (pmol cAMP) | Co-Transfection of 1) Vector-TSHR(A623I) 2) mGluR7 versions 3) 16 mU/ml TSH (pmol cAMP) | Percent (%) Decrease between Endogenous and Non-endogenous Version of mGluR7 (with TSH) | mGluR7 Inverse Agonist | MGluR7 Agonist |
|---|---|---|---|---|---|
| pCMV (without TSHR) | 4 | — | — | Increase | Decrease |
| pCMV | 23 | 288 | — | | |
| MgluR7 wt | 21 | 402 | 0 | | |
| W590S | 9 | 138 | 66 | | |
| R659H | 7 | 156 | 61 | | |
| T771C | 7 | 156 | 61 | | |
| I790K | 9 | 151 | 62 | | |

Figure 5:
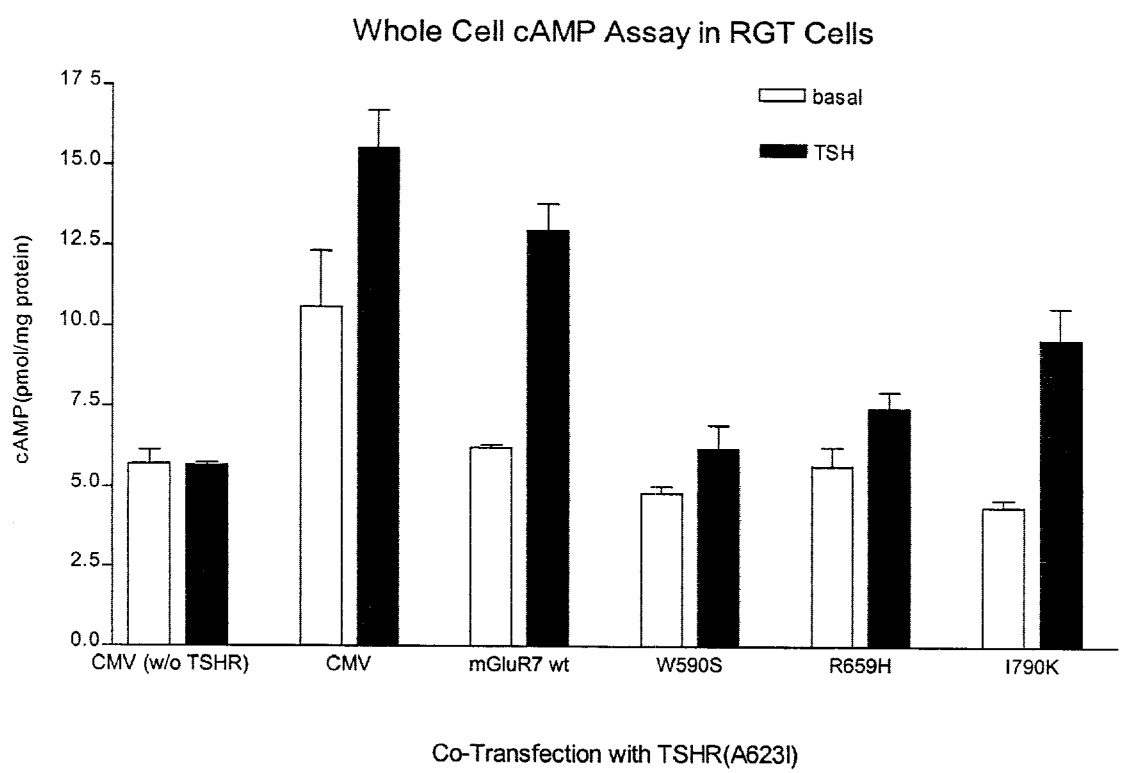
FIG. 5 provides graphic results of comparative analysis of a co-transfection of non-endogenous TSHR(A623I) ("signal enhancer") and an endogenous target receptor, in this case mGluR7 ("mGluR7 wt"), versus non-endogenous, constitutively activated versions of the target receptor mGluR7 ("W590S," "R659H" "T771C" and "I790K") co-transfected with non-endogenous TSHR(A623I), utilizing a cell-based adenylyl cyclase assay in RGT cells. This assay involved the addition of TSH, the endogenous ligand for TSHR.

Versions of mGluR7 transfected in RGT cells support the data of above. Reference is made to FIG. 5. In FIG. 5, W590S evidenced about a 52% decrease in cAMP production; R659H evidenced about a 43% reduction; T771C evidenced about a 5% reduction; and I790K evidenced about a 28% reduction in the production of cAMP when compared to the endogenous version of mGluR7 receptor.

Because mGluR7 predominantly couples with Gi in its active state, a decrease in cAMP production signifies that the disclosed non-endogenous versions of mGluR7 are constitutively active. Thus, a candidate compound which impacts the mGluR7 receptor by increasing the cAMP signal is an inverse agonist, while a mGluR7 agonist will decrease the cAMP signal. Based upon the data generated for FIGS. 5 and 6, "W590S," "R659H," "T771C" and "I790K" are preferred non-endogenous versions of mGluR7, most preferably is "W590S" when used in a TSHR constitutively activated co-transfection approach using a cAMP assay in both 293 and RGT cells.

Figure 11:
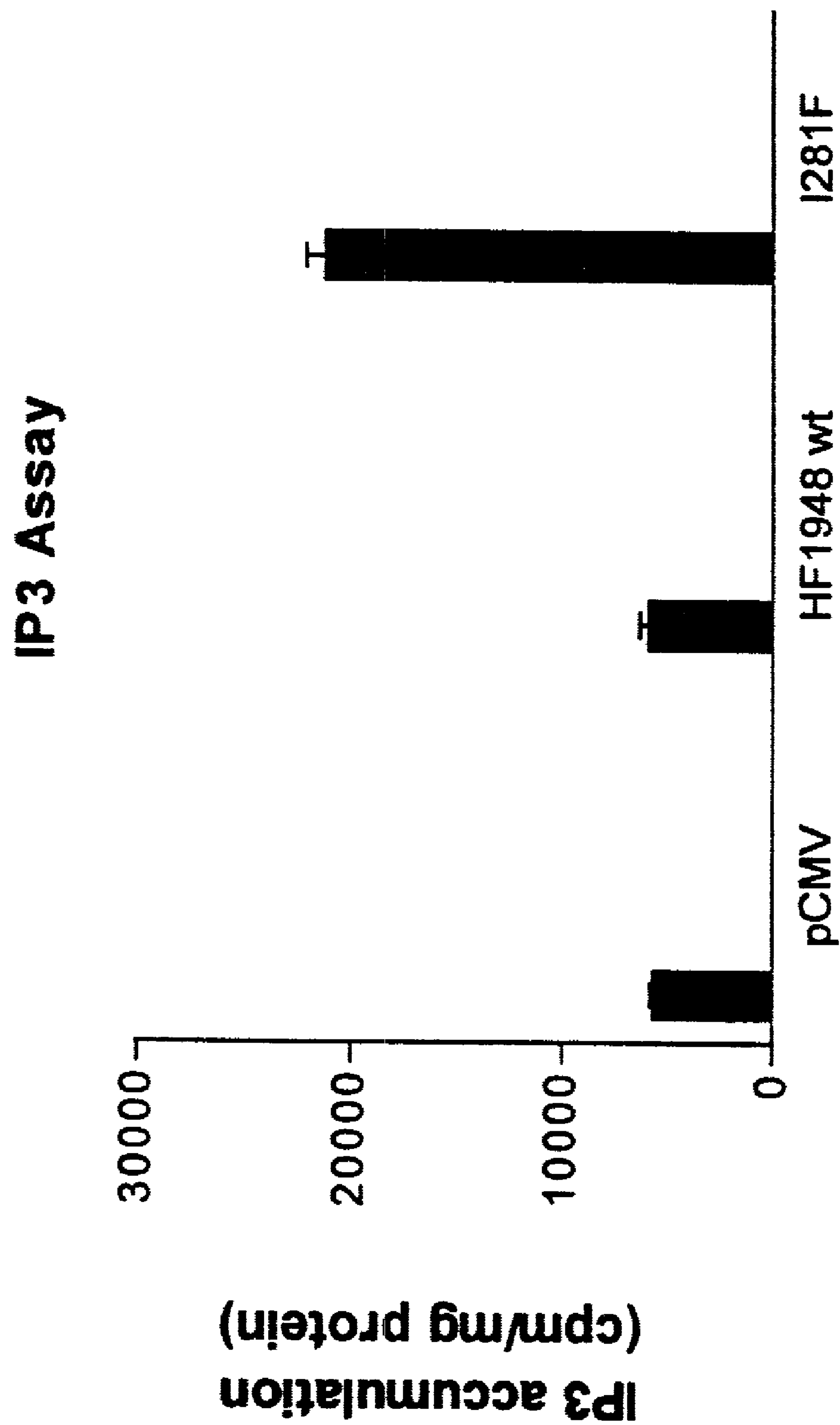
FIG. 11 is a comparative analysis of endogenous, non-constitutively active HF1948 ("wt") and non-endogenous, constitutively activated version of HF1948 ("I281F") in an IP3 assay, where the control is expression vector ("pCMV").
Figure 12:
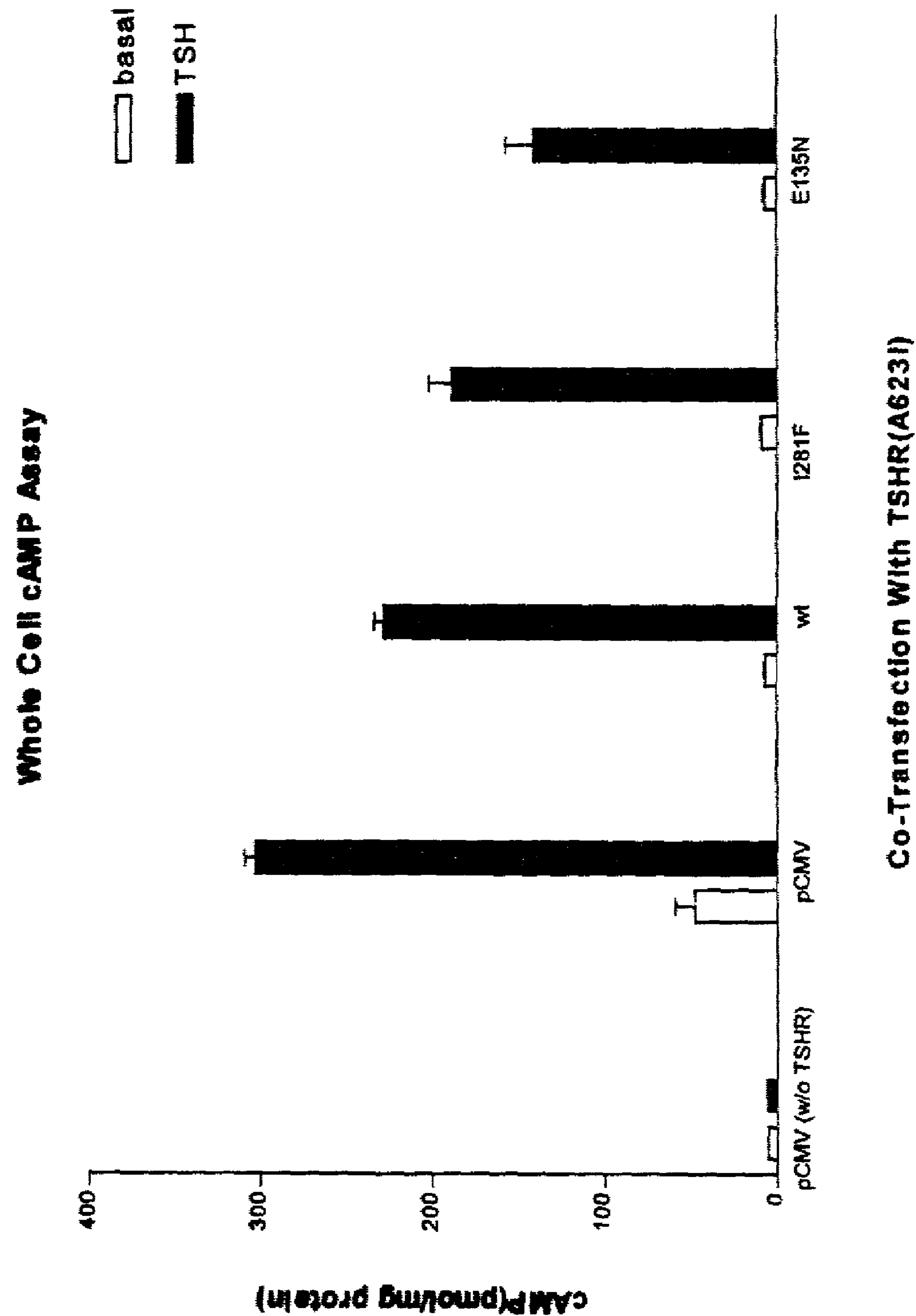
FIG. 12 is comparative analysis of a co-transfection of non-endogenous TSHR-A623I ("signal enhancer") and an endogenous target receptor, in this case HF1948 ("HF1948 wt"), versus non-endogenous, constitutively activated versions of the target receptor HF1948 ("I281F" and "E135N") co-transfected with non-endogenous TSHR-A623I, utilizing a whole cell adenylyl cyclase assay. This assay involved the addition of TSH, the endogenous ligand for TSHR.

Reference is made to FIG. 12. In FIG. 12, non-endogenous versions of HF1948 ("I281F" and "E135N") evidenced a reduction in cAMP production, about an 18% and about a 39% reduction, respectively, when compared to the endogenous version of HF1948 ('wt"). This data suggests that both non-endogenous I281F and E135N versions of HF1948 are constitutively activated. This decrease in cAMP further suggests that these versions may be Gi-coupled. In addition to being Gi-coupled, FIG. 11 suggests that non-endogenous I281F version of HF1948 may also couple to Gq G protein. (See, Example 4(5)(f) below).

Figure 16:
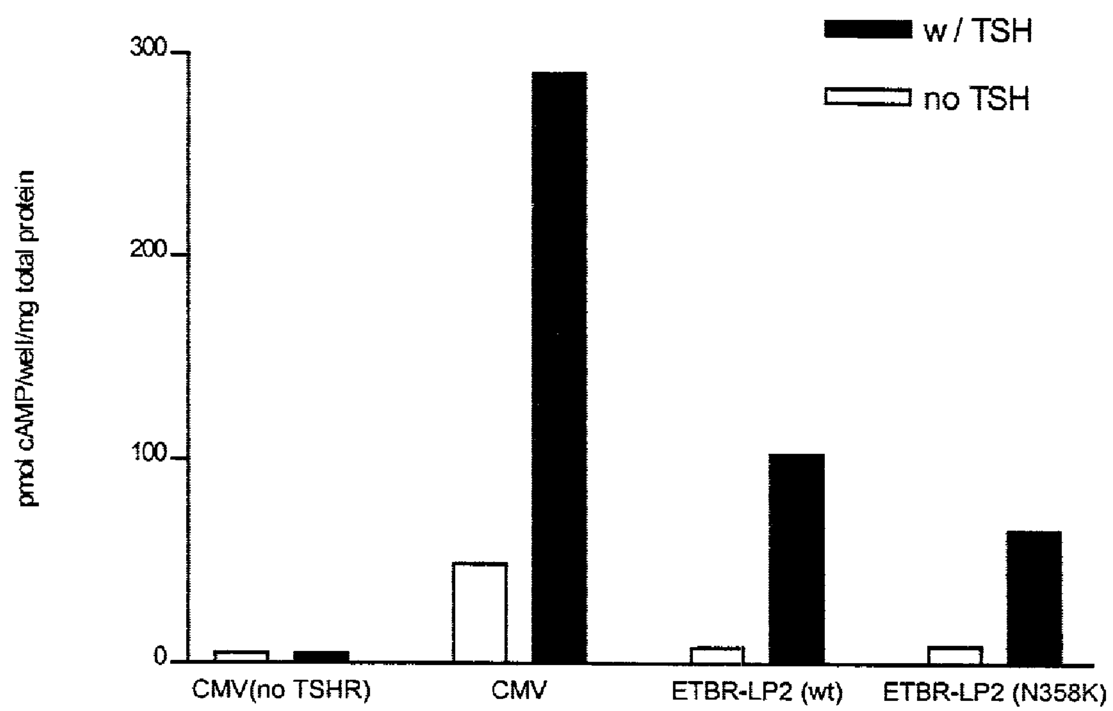
FIG. 16 provides graphic results of comparative analysis of a co-transfection of non-endogenous TSHR-A623I ("TSHR-A623I") (with and without TSH) and endogenous ETBR-LP2 ("WT"), versus non-endogenous, constitutively activated ETBR-LP2 ("N358K") co-transfected with mutated TSHR-A623I (with and without TSH) utilizing an adenylyl cyclase assay.

Reference is made to FIG. 16. FIG. 16 evidences about a 36% decrease in cAMP production of cells co-transfected with TSHR-A623I ("TSHR-A623I") (in the presence of TSH) and non-endogenous, constitutively activated ETBR-LP2 ("N358K") (65.96 pmole cAMP/well) compared to TSHR-A623I with endogenous ETBR-LP2 ("WT") (102.59 pmol cAMP/well). About a 77% and about a 65% decrease in production of cAMP was evidenced when comparing TSHR-A623I co-transfected with ETBR-LP2("N358K") and TSHR-A623I co-transfected with ETBR-LP2("WT") against TSHR-A623I co-transfected with pCMV (290.75 pmol cAMP/well), respectively. Preferably, this approach is used for screening an inverse agonist, which would increase the signal, whereas an agonist should decrease the signal. To confirm that a small molecule binds ETBR-LP2 and not to the TSHR-A623I construct, the small molecule is preferably screened against the construct in the absence of ETBR-LP2.

5. Reporter-based Assays a. CRE-Luc Reporter Assay ($G_s$-associated Receptors)

293 and 293T cells were plated-out on 96 well plates at a density of $2\times10^4$ cells per well and were transfected using Lipofectamine Reagent (BRL) the following day according to manufacturer instructions. A DNA/lipid mixture was prepared for each 6-well transfection as follows: 260 ng of plasmid DNA in 100 μl of DMEM are gently mixed with 2 μl of lipid in 100 μl of DMEM (the 260 ng of plasmid DNA consisted of 200 ng of a 8×CRE-Luc reporter plasmid, 50 ng of pCMV comprising endogenous receptor or non-endogenous receptor or pCMV alone, and 10 ng of a GPRS expression plasmid (GPRS in pcDNA3 (Invitrogen)). The 8×CRE-Luc reporter plasmid is prepared as follows: vector SRIF-β-gal was obtained by cloning the rat somatostatin promoter (−71/+51) at BglV-HindIII site in the pβgal-Basic Vector (Clontech). Eight (8) copies of cAMP response element were obtained by PCR from an adenovirus template AdpCF126CCRE8 (see, 7 *Human Gene Therapy* 1883 (1996)) and cloned into the SRIF-β-gal vector at the Kpn-BglV site, resulting in the 8×CRE-β-gal reporter vector. The 8×CRE-Luc reporter plasmid was generated by replacing the beta-galactosidase gene in the 8×CRE-β-gal reporter vector with the luciferase gene obtained from the pGL3-basic vector (Promega) at the HindIII-BamHI site. Following 30 min. incubation at room temperature, the DNA/lipid mixture was diluted with 400 μl of DMEM and 100 μl of the diluted mixture was added to each well. One hundred μl of DMEM with 10% FCS was added to each well after a 4 hr incubation in a cell culture incubator. The following day the transfected cells were changed with 200 μl/well of DMEM with 10% FCS. Eight hours later, the wells were changed to 100 μl /well of DMEM without phenol red, after one wash with PBS. Luciferase activity was measured the next day using the LucLite™ reporter gene assay kit (Packard) following manufacturer's instructions and read on a 1450 MicroBeta™ scintillation and luminescence counter (Wallac).

Figure 2:
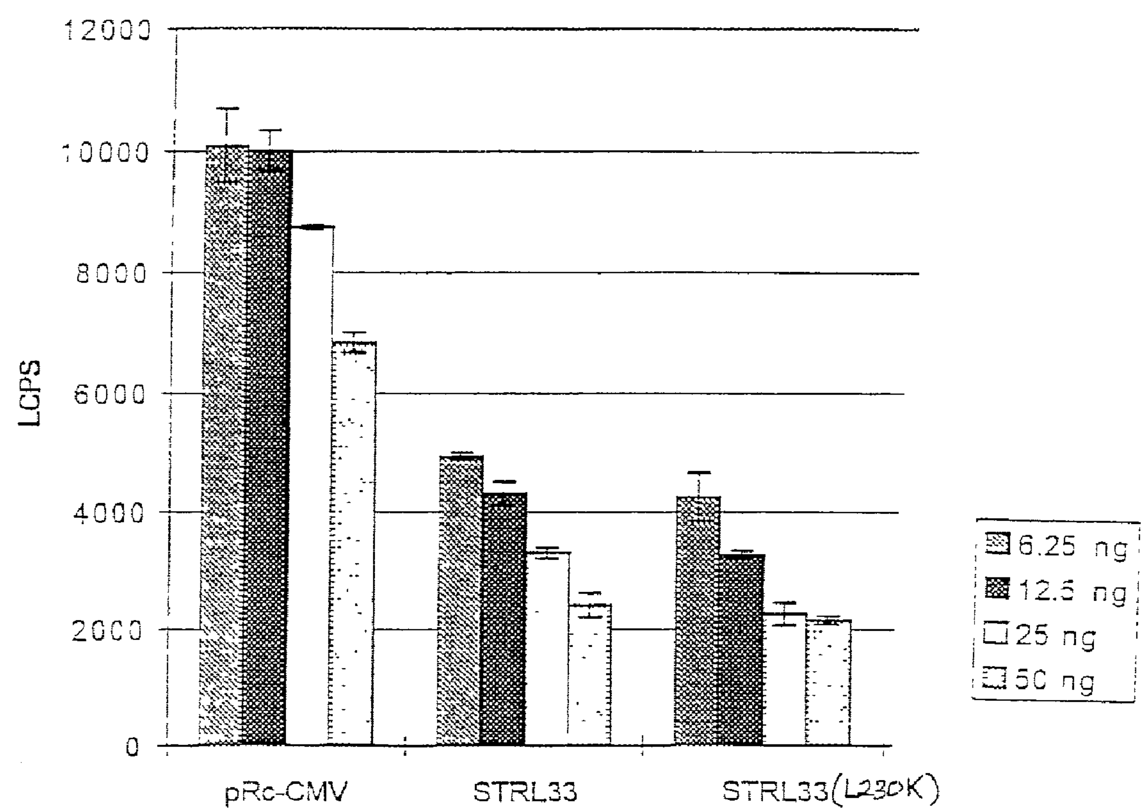
FIG. 2 provides graphic results of comparative analysis of endogenous STRL33 against non-endogenous, constitutively activated STRL33 ("STRL33(L230K)") utilizing an 8×CRE-Luc Reporter assay in 293T cells as compared with the control ("CMV").

Reference is made to FIG. 2. FIG. 2 evidences about a 50% decrease in activity of STRL33 when compared to the control (CMV) at 12.5 ng of STRL33 receptor. When comparing the endogenous version of STRL33 with that of the non-endogenous version, the non-endogenous STRL33 ("STRL33(L230K)")) evidence about a 30% decrease in receptor activity when comparing at 12.5 ng of protein, and about a 40% decrease in activity at 25 ng of protein. This data suggests that non-endogenous version of STRL33 receptor is constitutively active and may couple to the G protein, Gi.

b. AP1 Reporter Assay ($G_q$-associated Receptors)

A method to detect $G_q$ stimulation depends on the known property of $G_q$-dependent phospholipase C to cause the activation of genes containing AP1 elements in their promoter. A Pathdetect™ AP-1 cis-Reporting System (Stratagene, Catalogue # 219073) was utilized following the protocol set forth above with respect to the CREB reporter assay, except that the components of the calcium phosphate precipitate were 410 ng pAP1-Luc, 80 ng pCMV-receptor expression plasmid, and 20 ng CMV-SEAP.

Figure 17:
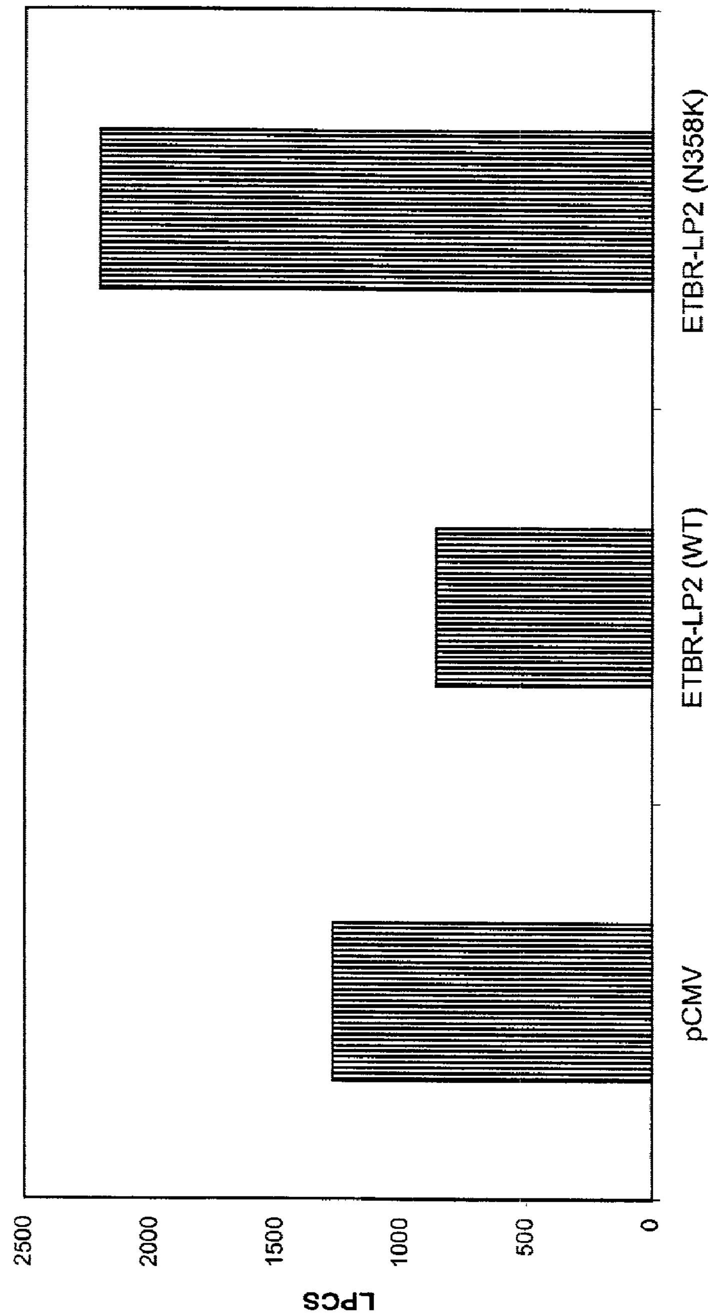
FIG. 17 provides a graphic result comparative analysis of endogenous ETBR-LP2 ("WT") and non-endogenous, constitutively activated ETBR-LP2 ("N358K") utilizing an AP1 reporter assay system.

Reference is made to FIG. 17. FIG. 17 represents a 61.1% increase in activity of the non-endogenous, constitutively active version of human ETBR-LP2 ("N358K") (2203 relative light units) compared with that of the endogenous ETBR-LP2 (862 relative light units). This data suggests that non-endogenous version of ETBR-LP2 receptor is constitutively active and may couple to the G protein, Gi.

c. SRF-Luc Reporter Assay ($G_q$-associated Receptors)

One method to detect $G_q$ stimulation depends on the known property of $G_q$-dependent phospholipase C to cause the activation of genes containing serum response factors in their promoter. A Pathdetect™ SRF-Luc-Reporting System (Stratagene) can be utilized to assay for $G_q$ coupled activity in, e.g., COS7 cells. Cells are transfected with the plasmid components of the system and the indicated expression plasmid encoding endogenous or non-endogenous GPCR using a Mammalian Transfection™ Kit (Stratagene, Catalogue #200285) according to the manufacturer's instructions. Briefly, 410 ng SRF-Luc, 80 ng pCMV-receptor expression plasmid and 20 ng CMV-SEAP (secreted alkaline phosphatase expression plasmid; alkaline phosphatase activity is measured in the media of transfected cells to control for variations in transfection efficiency between samples) are combined in a calcium phosphate precipitate as per the manufacturer's instructions. Half of the precipitate is equally distributed between 3 wells in a 96-well plate, kept on the cells in a serum free media for 24 hours. The last 5 hours the cells are incubated with 1 μM Angiotensin, where indicated. Cells are then lysed and assayed for luciferase activity using a Luclite™ Kit (Packard, Cat. # 6016911) and "Trilux 1450 Microbeta" liquid scintillation and luminescence counter (Wallac) as per the manufacturer's instructions. The data can be analyzed using GraphPad Prism™ 2.0a (GraphPad Software Inc.).

d. SRE Reporter Assay

A SRE-Luc Reporter (a component of Mercury Luciferase System 3, Clontech Catalogue # K2053-1) was utilized in 293 cells. Cells were transfected with the plasmid components of this system and the indicated expression plasmid encoding endogenous or non-endogenous receptor using Lipofectamine Reagent (Gibco/BRL, Catalogue #18324-012) according to the manufacturer's instructions. Briefly, 420 ng SRE-Luc, 50 ng CMV (comprising the GPR37 receptor) and 30 ng CMV-SEAP (secreted alkaline phosphatase expression plasmid; alkaline phosphatase activity is measured in the media of transfected cells to control for variations in transfection efficiency between samples) were combined in a cationic lipid-DNA precipitate as per the manufacturer's instructions. The final volume was 25 μl brought up with Optimem (Vendor). This is referred to as the "template mix." The template mix was combined with the lipfectamine in a polystrene tube and was incubated for 30 minutes. During the incubation, the cells were washed with 100 μl Optimem. After incubation, 200 μl of Optimem was added to mix and 40 μl–50 μl/well. The cells were left to mix overnight. The media was replaced with fresh medium the following morning to DMEM/Phenol red free/1% FBNS at 130μl/well. The The cells were then assayed for luciferase activity using a Luclite™ Kit (Packard, Cat. # 6016911) and "Trilux 1450 Microbeta" liquid scintillation and luminescence counter (Wallac) as per the manufacturer's instructions. The data were analyzed using GraphPad Prism™ 2.0a (GraphPad Software Inc.).

Figure 7:
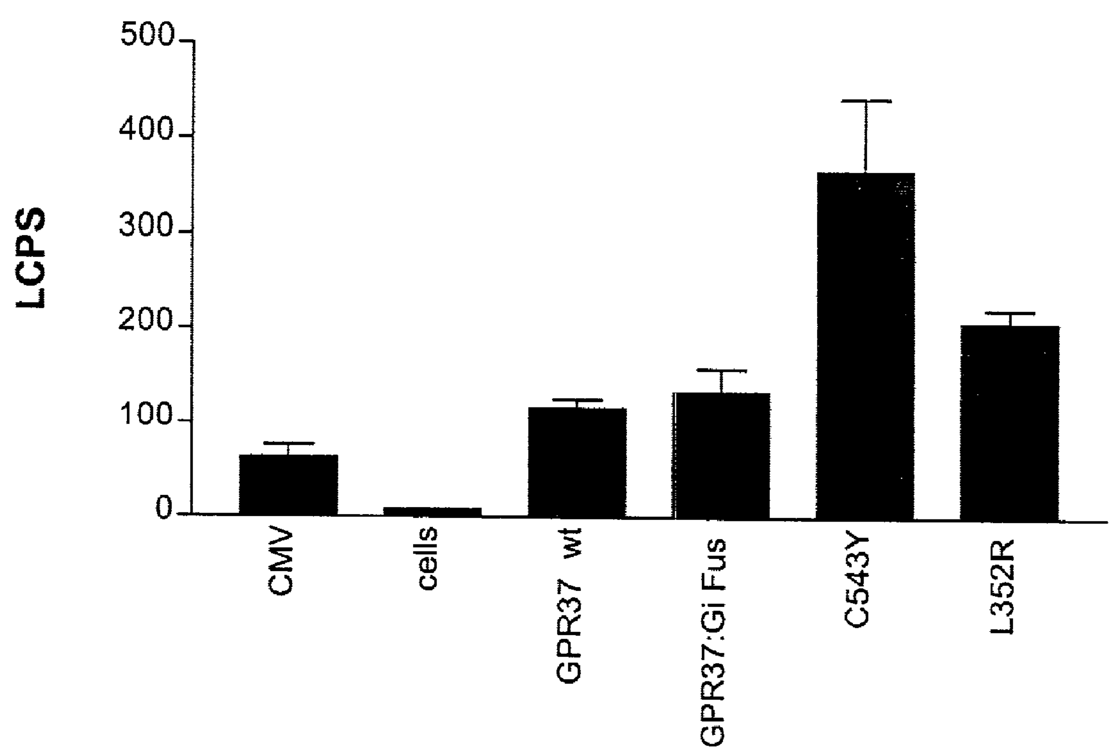
FIG. 7 is a comparative analysis of endogenous, non-constitutively active GPR37 ("wt") and non-endogenous, constitutively activated versions of GPR37 ("C543Y" and "L352R") in an SRE Reporter assay, where the control is expression vector ("CMV").
Figure 8:
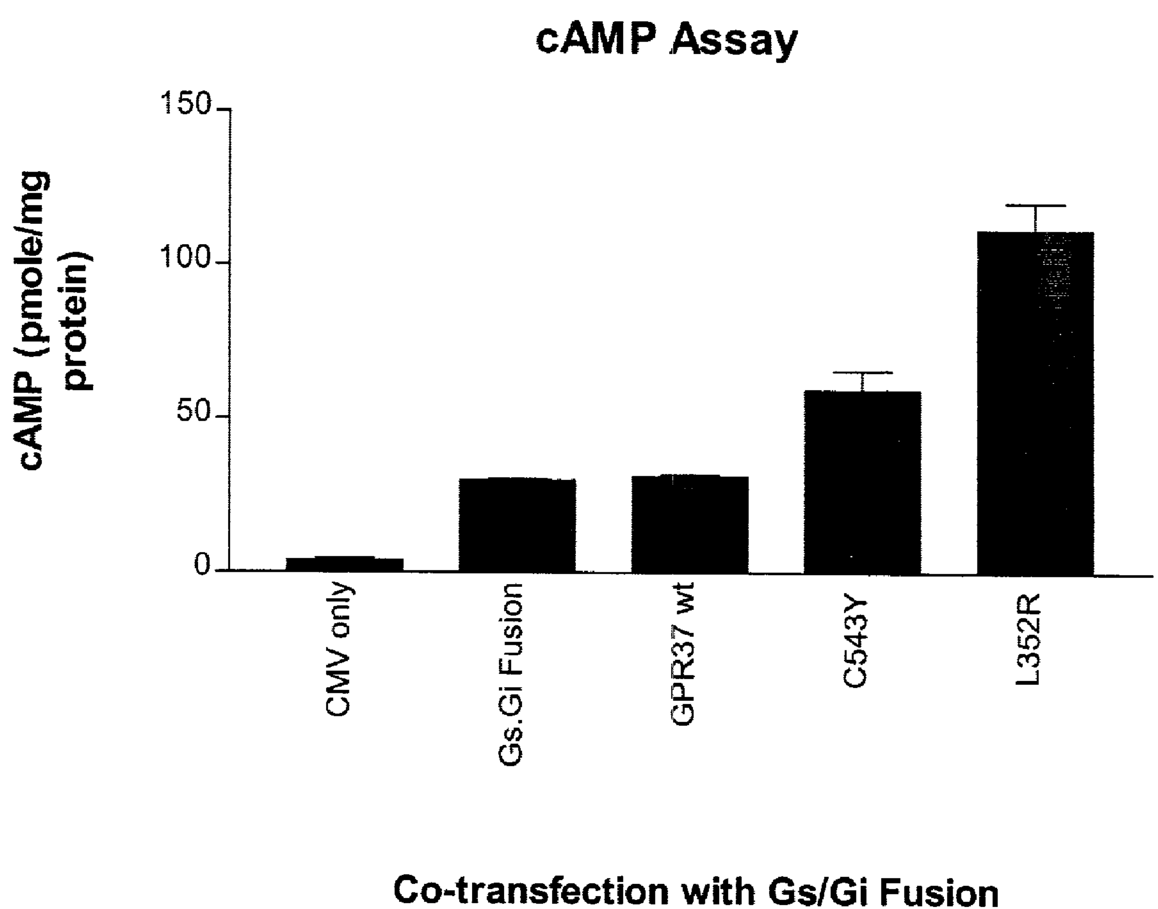
FIG. 8 is comparative analysis of a co-transfection of Gs/Gi Fusion Construct and an endogenous target receptor, in this case GPR37 ("GPR37 wt"), versus non-endogenous, constitutively activated versions of the target receptor GPR37 ("C543Y" and "L352R") co-transfected with Gs/Gi Fusion Construct utilizing a whole cell second messenger cAMP assay.

Reference is made to FIG. 7. In FIG. 7, when comparing the non-endogenous version of GPR37 ("C543Y") with the endogenous version ("wt"), the C543Y mutation evidences about a 316% increase in cAMP production over the wt version, while the non-endogenous version "L352R" evidence about a 178% increase in production of cAMP over the wt version. This data suggests that both non-endogenous versions of GPR37, C543Y and L352R, are constitutively activated.

e. E2F-Luc Reporter Assay

A pE2F-Luc Reporter (a component of Mercury Luciferase System 3, Clontech Catalogue # K2053-1) was utilized in 293A cells. Cells were transfected with the plasmid components of this system and the indicated expression plasmid encoding endogenous or non-endogenous receptor using Lipofectamine Reagent (Gibco/BRL, Catalogue #18324-012) according to the manufacturer's instructions. Briefly, 400 ng pE2F-Luc, 80 ng CMV (comprising the GPR35 receptor) and 20 ng CMV-SEAP (secreted alkaline phosphatase expression plasmid; alkaline phosphatase activity is measured in the media of transfected cells to control for variations in transfection efficiency between samples) were combined in a cationic lipid-DNA precipitate as per the manufacturer's instructions. Half of the precipitate was equally distributed over 3 wells in a 96-well plate, kept on the cells overnight, and replaced with fresh medium the following day. Forty-eight (48) hr after the start of the transfection, cells were treated and assayed for luciferase activity using a Luclite™ Kit (Packard, Cat. # 6016911) and "Trilux 1450 Microbeta" liquid scintillation and luminescence counter (Wallac) as per the manufacturer's instructions. The data were analyzed using GraphPad Prism™ 2.0a (Graph Pad Software Inc.).

Figure 14:
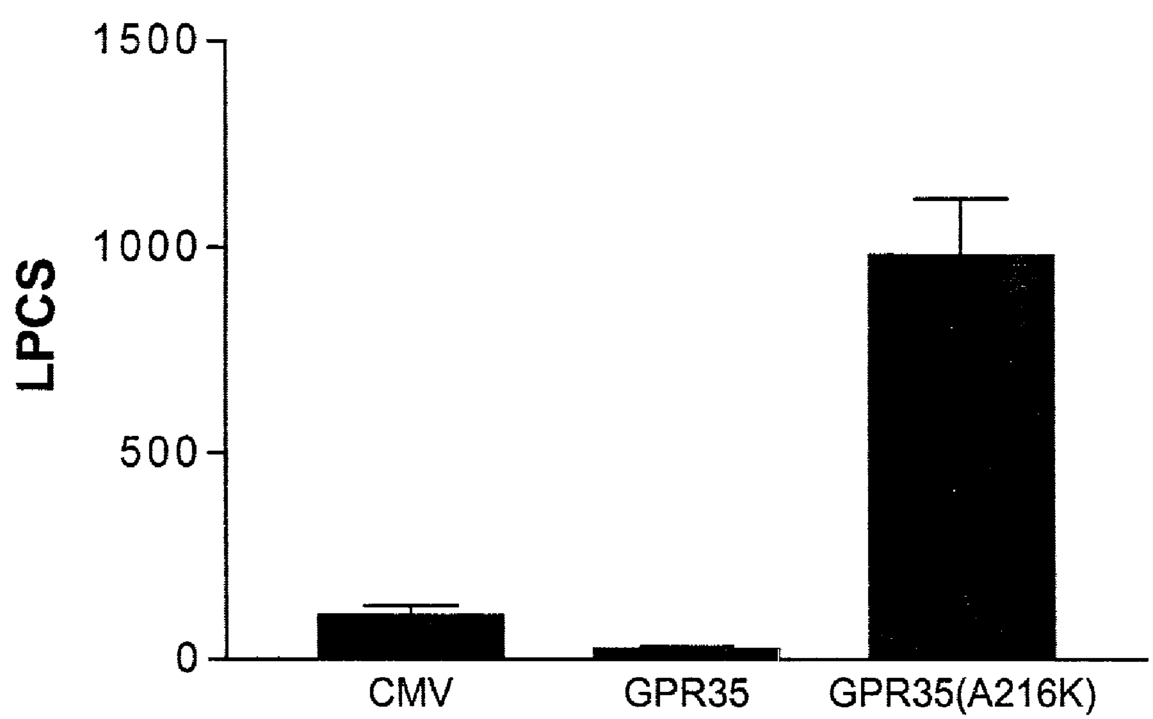
FIG. 14 provides graphic results of comparative analysis of endogenous GPR35 against non-endogenous, constitutively activated GPR35 ("GPR35(A216K)") utilizing an E2F-Luc Reporter assay in 293A cells.

Reference is made to FIG. 14. FIG. 14 represents about a 100% increase in activity of the non-endogenous, constitutively active version of human GPR35 (A216K) (607.13 relative light units) compared with that of the endogenous GPR35 (24.97 relative light units). This data suggests that GPR35(A216K) interacts with the transcription factor E2F to drive the expression of the luciferase protein. Such interaction with E2F, along with evidence that GPR35 is expressed in colorectal cancer cells, further suggests that GPR35 may play a role in cancer cell proliferation. Thus, based upon these data, a preferred candidate compound which impacts the GPR35 receptor would be an inverse agonist. This data suggest that an inverse agonist of GPR35 would be useful in the treatment of cancerous conditions, colorectal cancer in particular.

f. Intracellular $IP_3$ Accumulation Assay ($G_q$-associated Receptors)

On day 1, cells comprising the receptors (endogenous and/or non-endogenous) are plated onto 24 well plates, usually $1\times10^5$ cells/well (although his number can be optimized. On day 2 cells were transfected by firstly mixing 0.25 ug DNA in 50 μl serum free DMEM/well and 2 μl lipofectamine in 50 μl serum free DMEM/well. The solutions were gently mixed and incubated for 15–30 min at room temperature. Cells were then washed with 0.5 ml PBS and 400 μl of serum free media and then mixed with the transfection media and added to the cells. The cells were incubated for 3–4 hrs at 37° C./5% $CO_2$ and then the transfection media was removed and replaced with 1 ml/well of regular growth media. On day 3 the cells are labeled with $^3$H-myo-inositol. Briefly, the media was removed and the cells are washed with 0.5 ml PBS. Then 0.5 ml inositol-free/serum free media (GIBCO BRL) were added/well with 0.25 μCi of $^3$H-myo-inositol/well and the cells incubated for 16–18 hrs overnight at 37° C./5%$CO_2$. On Day 4 the cells are washed with 0.5 ml PBS and 0.45 ml of assay medium was added containing inositol-free/serum free media 10 μM pargyline 10 mM lithium chloride or 0.4 ml of assay medium. The cells were then incubated for 30 min at 37° C. The cells are then washed with 0.5 ml PBS and 200 μl of fresh/ice cold stop solution (1M KOH; 18 mM Na-borate; 3.8 mM EDTA) is added to each well. The solution was kept on ice for 5–10 min (or until cells are lysed) and then neutralized by 200 μl of fresh/ice cold neutralization solution (7.5% HCL). The lysate was then transferred into 1.5 ml Eppendorf tubes and 1 ml of chloroform/methanol (1:2) was added/tube. The solution was vortexed for 15 sec and the upper phase was applied to a Biorad AG1-X8™ anion exchange resin (100–200 mesh). First, the resin was washed with water at 1:1.25 W/V and 0.9 ml of upper phase was loaded onto the column. The column was then washed with 10 ml of 5 mM myo-inositol and 10 ml of 5 mM Na-borate/60 mM Na-formate. The inositol tris phosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at 4° C. in water.

Figure 6:
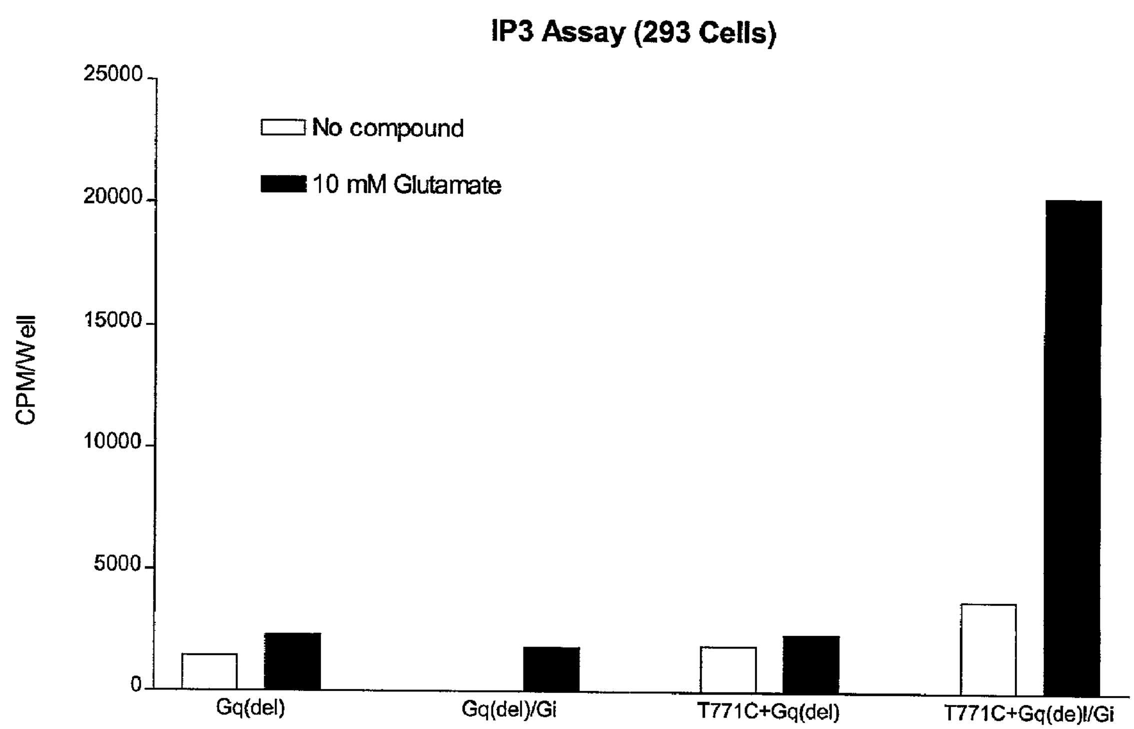
FIG. 6 provides an illustration of second messenger $IP_3$ production of non-endogenous mGluR7, "T771C", co-transfected with non-endogenous versions of Gq protein, "Gq (del)" and "Gq(del)/Gi" compared with "Gq(del)" and "Gq (del)/Gi" in the presence and absence of glutamate.

Reference is made to FIG. 6. In FIG. 6, 293 cells were transfected with Gq protein containing a six amino acid deletion, "Gq(del)"; Gq protein fused to a Gi protein, "Gq(del)/Gi", and non-endogenous mGluR7, T771C together with Gq(del), "T771C+Gq(del)" and T771C with Gq(del)/Gi, "T771C+Gq(del)/Gi". Inositol triphosphate was measured in the presence and absence of glutamate. Co-transfection of non-endogenous version of mGluR7 with Gq(del)/Gi evidence about a 1850 fold increase when compared to the Gq(del)/Gi in the presence of glutamate; and about a 860 fold increase compared with T771C+Gq(del)/Gi in the presence of glutamate. These data evidences that mGluR7, a Gi coupled receptor, can be activated via the Gq protein. Therefore, the Gq(del)/Gi Fusion Construct can be co-transfected with a GPCR and used to as a tool to screen for candidate compounds.

Reference is made to FIG. 11. In FIG. 11, when comparing the non-endogenous version of HF1948 ("I281F") with the endogenous version ("wt"), the I281F mutation evidences about a 361% increase in IP3 accumulation over the wt version. This data suggests that the non-endogenous I281F version of HF1948 is constitutively activated and is Gq-coupled.

Example 5

Fusion Protein Preparation a. GPCR: $G_s$ Fusion Construct

The design of the constitutively activated GPCR-G protein fusion construct can be accomplished as follows: both the 5' and 3' ends of the rat G protein $G_s\alpha$ (long form; Itoh, H. et al., 83 *PNAS* 3776 (1986)) is engineered to include a HindIII (5'-AAGCTT-3') sequence thereon. Following confirmation of the correct sequence (including the flanking HindIII sequences), the entire sequence is shuttled into pcDNA3.1(−) (Invitrogen, cat. no. V795-20) by subcloning using the HindIII restriction site of that vector. The correct orientation for the $G_s\alpha$ sequence will be determined after subcloning into pcDNA3.1(−). The modified pcDNA3.1(−) containing the rat $G_s\alpha$ gene at HindIII sequence is then verified; this vector will then be available as a "universal" $G_s\alpha$ protein vector. The pcDNA3.1 (−) vector contains a variety of well-known restriction sites upstream of the HindIII site, thus beneficially providing the ability to insert, upstream of the $G_s$ protein, the coding sequence of an endogenous, constitutively active GPCR. This same approach can be utilized to create other "universal" G protein vectors, and, of course, other commercially available or proprietary vectors known to the artisan can be utilized. In some embodiments, the important criteria is that the sequence for the GPCR be upstream and in-frame with that of the G protein.

Spacers in the restriction sites between the G protein and the GPCR are optional. The sense and anti-sense primers included the restriction sites for XbaI and EcoRV, respectively, such that spacers (attributed to the restriction sites) exist between the G protein and the GPCR.

PCR will then be utilized to secure the respective receptor sequences for fusion within the $G_s\alpha$ universal vector disclosed above, using the following protocol for each: 100 ng cDNA for GPCR will be added to separate tubes containing 2 μl of each primer (sense and anti-sense), 3 μl of 10 mM dNTPs, 10 μl of 10×TaqPlus™ Precision buffer, 1 μl of TaqPlus™ Precision polymerase (Stratagene: #600211), and 80 μl of water. Reaction temperatures and cycle times for the GPCR will be as follows with cycle steps 2 through 4 were repeated 35 times: 94° C. for 1 min; 94° C. for 30 seconds; 62° C. for 20 sec; 72° C. 1 min 40 sec; and 72° C. 5 min. PCR products will be run on a 1% agarose gel and then purified. The purified products will be digested with XbaI and EcoRV and the desired inserts purified and ligated into the $G_s$ universal vector at the respective restriction sites. The positive clones will be isolated following transformation and determined by restriction enzyme digestion; expression using 293 cells will be accomplished following the protocol set forth infra. Each positive clone for GPCR-$G_s$ Fusion Protein will be sequenced to verify correctness.

g. $G_q$(6 Amino Acid Deletion)/$G_i$ Fusion Construct

The design of a $G_q$ (del)/$G_i$ fusion construct was accomplished as follows: the N-terminal six (6) amino acids (amino acids 2 through 7), having the sequence of TLESIM (SEQ.ID.NO.:88) Gαq-subunit was deleted and the C-terminal five (5) amino acids, having the sequence EYNLV (SEQ.ID.NO.:89) was replaced with the corresponding amino acids of the Gαi Protein, having the sequence DCGLF (SEQ.ID.NO.:90). This fusion construct was obtained by PCR using the following primers:

5'-gatcAAGCTTCCATGGCGTGCTGCCTGAGCGAGG-3' (SEQ.ID.NO.:91) and

5'-gatcGGATCCTTAGAACAGGCCGCAGTC-CTTCAGGTTCAGCTGCAGGATGGTG-340 (SEQ.ID.NO.:92) and Plasmid 63313 which contains the mouse Gαq-wild type version with a hemagglutinin tag as template. Nucleotides in lower caps are included as spacers.

TaqPlus® Precision DNA polymerase (Stratagene) was utilized for the amplification by the following cycles, with steps 2 through 4 repeated 35 times: 95° C. for 2 min; 95° C. for 20 sec; 56° C. for 20 sec; 72° C. for 2 min; and 72° C. for 7 min. The PCR product will be cloned into a pCRII-TOPO vector (Invitrogen) and sequenced using the ABI Big Dye Terminator kit (P.E. Biosystems). Inserts from a TOPO clone containing the sequence of the fusion construct will be shuttled into the expression vector pcDNA3.1 (+) at the HindIII/BamHI site by a 2 step cloning process.

c. Gs/Gi Fusion Protein Construct

The design of a Gs/Gi Fusion Protein Construct was accomplished as follows: the C-terminal five (5) amino acids of Gαs-subunit was deleted, having the sequence 5'-QYELL-3' (SEQ.ID.NO.:93) and replaced with the corresponding amino acids of the Gαi protein, having the sequence 5'-DCGLF-3' (SEQ.ID.NO.:94). This protein fusion construct was obtained by PCR using a 5' and 3' oligonucleotides.

TaqPlus Precision DNA polymerase (Stratagene) was utilized for the amplification by the following cycles, with steps 2 through 4 repeated 25 times: 98° C. for 2 min; 98° C. for 30 sec; 60° C. for 30 sec; 72° C. for 2 min; and 72° C. for 5 min. The PCR product was cloned into a pCRII-TOPO vector (Invitrogen) and sequenced using the ABI Big Dye Terminator kit (P.E. Biosystems). Inserts from a TOPO clone containing the sequence of the protein fusion construct was shuttled into the expression vector pcDNA3.1(+) at the restriction site. The nuclei acid sequence for Gs/Gi Protein Fusion Construct was then determined. See SEQ.ID.NO.:95 for the nucleic acid sequence and SEQ.ID.NO.:96 for the amino acid sequence.

Example 6

Schwann Cell Preparation

2 L of neonate rat pups (Sprague Dawley) (at Post-pardum day 2-Post-pardum day 3 stage) were placed on ice to euthanize. Pups were then removed and decapitated to drain the blood. The neonates were placed, belly-down, on a dissection board and rinsed with 70% ethanol to sterilize. Using a scalpel, the skin was removed in the thigh area until the sciatic nerve was exposed (or until a thin white "string" extended from the spinal cord to the knee was visible). The nerves were placed in DMEM medium and then aspirated, followed by bringing the volume to 2.4 ml with DMEM media and adding 300 uL 10× Collagenase (0.3%, Sigma Cat. #C-9891) and 300 uL 10× Trypsin (0.25%, GIBCO Cat. #25095-019) for dissociation. Nerves were then incubated at 37° C. for 15 min, centrifuged for 5 min at 1,000 rpm followed by removing the media (repeated twice). 1 mL DMEM-HEPES and 1 mL DMEM/10% FBS were added and then transfered to a 50 mL conical tube. The contents of the tube were sheared with the following gauge needles (VWR): once with 18 G, twice with 21 G and twice with 23 G. The contents were placed on a Falcon cell strainer and spun at a very low speed (about 1200 rpm). The total volume was brought to 10 mL with DMEM/10% FBS and plated on a Poly-L-lysine treated 10 cm plate (Sigma, Cat. #P-1274). Plates were then incubated overnight in 37° C. humid incubator at 7% $CO_2$. Fresh media added with 100× ARA C (10 mM, Sigma, Cat. #C-1768) and cultured for an additional 48 hours. The cells were then washed with PBS (three times) to remove the ARA C and the following were added: DMEM/10% FBS, different concentrations of Forskolin in 100% ethanol (2 uM, 5 uM, 10 uM, 20 uM and 50 uM) (Calbiochem, Cat#344270), 80 ug of Pituitary Extract (Sigma, #P-1167) in PBS and 0.1% BSA, followed by growing the cells for 30 hours at 37° C. humidifier at 7% $CO_2$. The cells were then collected and the RNA was isolated and analyzed.

Antibody selection was accomplished according to the following: the Poly-L-Lysine treated plates were first washed with 1×PBS (three times), trypsinized with 1 mL of 0.5% trypsin-EDTA, for about 1 min and then neutralized with 9 mL of DMEM-HEPES buffer and 10% FBS. Cells were centrifuged at 1200 rpm for 5 min, resuspended in 3 mL of DMEM-HEPES to wash out the trypsin and spun for 5 min at 1200 rpm. Cells were then resuspended in 600 uL of DMEM-HEPES, leaving some media after the spin in order to have single cells. Thy1.1 antibody (Monoclonal Antibody, Sigma, Cat. #P-1274) was added at a 1:1000 dilution.

The cells were then incubated for 20 min at 37° C., slightly agitating the tube every two minutes. 20 uL of Guinea Pig complement (GIBCO, Cat. #19195-015) was thawed before using it, followed by adding the complement to the cells with the antibody to a final volume of 1 mL. The cells were incubated for about 20 min–30 min at 37° C. water bath and 10 mL of DMEM-HEPES was added and spun down for 5 min at 1200 rpm. Cells were resuspended in 5 mLs of DMEM/10% FBS and added to poly-L-lysine treated plates that contains pituitary extract and forskolin. The cells were left to recover for 24–48 hours and the immune selection procedure was repeated twice.

Example 7

Preparation of Crushed Rat Sciatic Nerve

The sciatic nerves of anesthetized (iso-florene), adult (10–13 week old) Sprague-Dawley rats were exposed at the sciatic notch. Nerve crush was produced by tightly compressing the sciatic nerve at the sciatic notch with flattened forceps twice, each time for 10 sec; this technique causes the axons to degenerate, but allows axonal regeneration. At varying times after nerve injury, the animals were euthanized by $CO_2$ inhalation, the distal nerve stumps were removed, and the most proximal 2–3 mm was trimmed off. For crushed nerves, the entire distal nerve was harvested. The nerves were immediately frozen in liquid nitrogen and stored at −80° C. Unlesioned sciatic nerves were obtained from animals of varying ages, from P0 (post crush) to P13.

Example 8

Tissue Distribution of the Disclosed Human GPCRs

1. RT-PCR

RT-PCR can be applied to confirm the expression and to determine the tissue distribution of several novel human GPCRs. Oligonucleotides utilized will be GPCR-specific and the human multiple tissue cDNA panels (MTC, Clontech) as templates. Taq DNA polymerase (Stratagene) will be utilized for the amplification in a 40 μl reaction according to the manufacturer's instructions. Twenty μl of the reaction will be loaded on a 1.5% agarose gel to analyze the RT-PCR products.

2. Dot-Blot

Using a commercially available human-tissue dot-blot format, endogenous GPCR was used to probe for a determination of the areas where such receptor is localized. The PCR fragments of Example 1 were used as the probe: radiolabeled probe was generated using this fragment and a Prime-It II™ Random Primer Labeling Kit (Stratagene, #300385), according to manufacturer's instructions. A human RNA Master Blot™ (Clontech, #7770-1) was hybridized with GPCR radiolabeled probe and washed under stringent conditions according manufacturer's instructions. The blot was exposed to Kodak BioMax Autoradiography film overnight at −80° C. Table F, below, lists the receptors and the tissues wherein expression was found. Exemplary diseases/disorders linked to the receptors are discussed in Example 6, infra.

TABLE F

| Receptor Identifier | Tissue Expression |
|---|---|
| STRL33 | Placenta, spleen and lung |
| GPR45 | Central nervous system, brain |
| GPR37 | central nervous system, specifically in the brain tissues, pituitary gland and placenta |
| GPR66 | pancreas, bone, testis, mammary glands, small intestine, and spleen |
| GPR26 | Brain |
| ETBR-LP2 | Brain, pituitary gland and placenta |

3. Northern Blot a. GPR37

RNA from Example 6 was harvested utilizing RNAzol B reagent (TelTest Inc., Cat. #CS-104), according to manufacturer's instructions. After electrophoresis in an 1% agarose/formaldehyde gel, the RNA was transferred to a nylon membrane (Sachleicher Schull) by capillary action using 10× SSC. A $^{32}$P-labelled GPR37 DNA probe was synthesized using a DNA fragment corresponding precisely to the 3' end of GPR37 and a High Prime labeling kit (Roche Molecular Biochemical) according to the manufacturer's instructions. Hybridization was performed using ExpressHyb Solution (Clontech, Cat. #8015-2) supplemented with 100 μg/ml salmon sperm DNA as follows. The membrane containing the separated RNA samples was first incubated with ExpressHyb solution at 65° C. overnight. The $^{32}$P-labelled GPR37 DNA probe was denatured by boiling for 2 minutes, placed on ice for 5 minutes and then transferred into the ExpressHyb solution bathing the membrane. After an overnight incubation at 65° C., the membrane was removed from the hybridization solution and washed four times for 15 minutes each in 2×SSC/1% SDS at 65° C., followed by two washes for 15 minutes each in 0.2×SSC/0.1% SDS at 55° C. Excess moisture was removed from the blot by gentle shaking, after which the blot was wrapped in plastic wrap and exposed to film overnight at −80° C.

Reference is made to FIG. 9. FIG. 9 evidences that GPR37 is expressed in Schwann cells, such that myelination can be maintained at 20 uM Forskolin.

Figure 10:
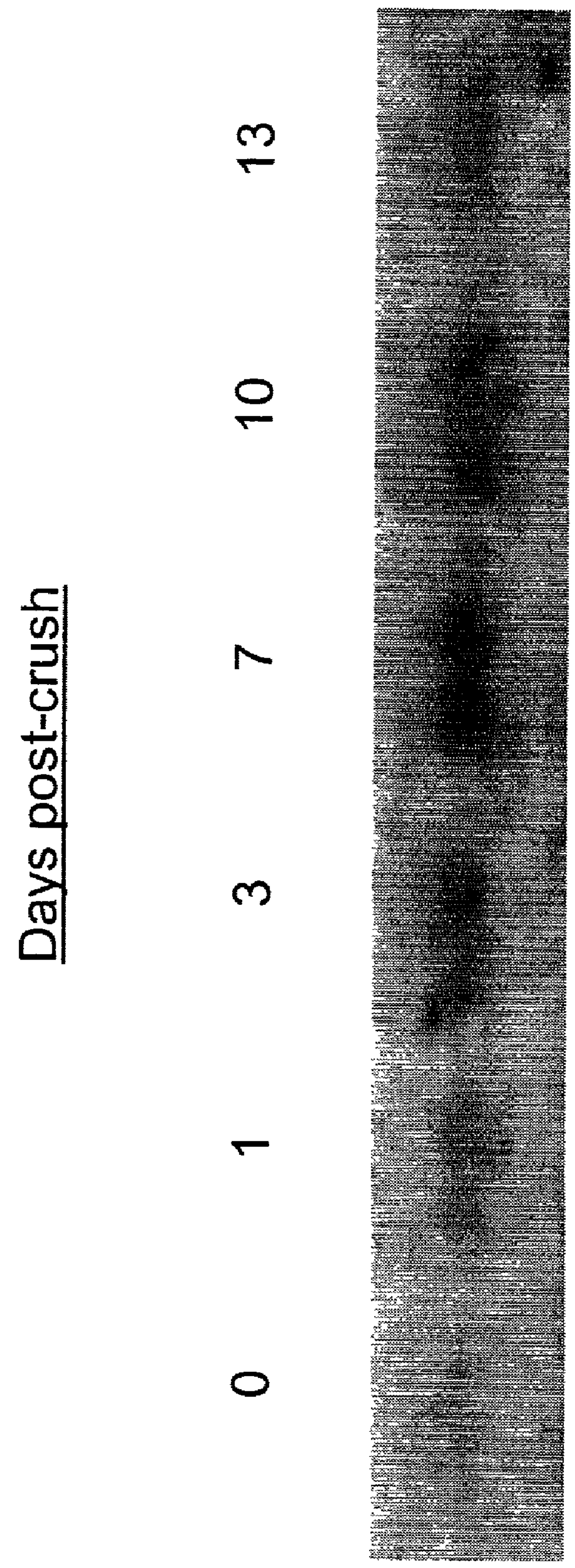
FIG. 10 is a representation of a Northern Analysis of GPR37 expressed in crushed rat sciatic nerve. GPR37 was highly up-regulated seven (7) days post crush.

FIG. 10 evidences that GPR37 is up-regulated in crushed rat sciatic nerves, specifically seven (7) days after crushing the nerves. Such data is consistent with the data presented in FIG. 9, i.e., GPR37 may play a role in the regeneration of nerves by stimulating the process of myelination in Schwann cells.

GPR37 is expressed in the human central nervous system, specifically in the brain tissues. It has been further determined that GPR37 is expressed in Schwann cells. When axons (or nerves) are injured, Schwann cells act to regenerate the nerves by forming myelin sheaths around the axons, which provides "insulation" in the form of myelin sheaths. This process, known as myelination, is important in that action potentials travel at a faster rate, thereby conserving metabolic energy. Schwann cells and their precursors play an important role in influencing the survival and differentiation of other cells that make up a pheripheral nerve. In addition, GPR37 has been determined to be expressed in crushed rat sciatic nerves. Such data supports the evidence that GPR37 may play a role in regenerating nerve cells. Based on the known functions of the specific tissues to which the receptor is localized, the putative functional role of the receptor can be deduced. Thus, in the case of hyper-myelination (e.g., tumorgenesis), an inverse agonist against GPR37 is preferred, while an agonist is preferred where hypo-myelination occurs (e.g., a degenerative disease such as diabetes).

b. GPR66

Total RNA from several pancreatic cell lines (e.g., HIT, ARIP, Tu6, RIN αTC, STC, NIT, and EcR-CHO, all of which are commercially available) were isolated using TRIzol reagent (Gibco/BRL, Cat #15596-018) according to manufacturer's instructions. After electrophoreseis in a 1% agarose/formaldehyde gel, the RNA was transferred to a nylon membrane using standard protocols. A $^{32}$P-labelled GPR66 probe was synthesized using a DNA fragment corresponding precisely to the entire coding sequence and a Prime It II Random Primer Labeling Kit (Stratagene, Cat. #300385) according to manufacturer's instructions. Hybridization was performed using ExpressHyb Solution (Clontech, Cat.#8015-2) supplemented with 10 ug/ml salmon sperm DNA as follows. The membrane containing the separated RNA samples were first incubated with ExpressHyb solution at 65° C. for 1 hour. The $^{32}$P-labeled GPR66 DNA probe was denatured by boiling for 2 min, placed on ice for 5 min and then transferred into the ExpressHyb solution bathing the membrane. After an overnight incubation at 65° C., the membrane was removed from the hybridization and washed four times for 15 min each in 2×SSC/1% SDS at 65° C., followed by two washes for 15 min each in 0.1×SSC/0.5% SDS at 55° C. Excess moisture was removed from the blot by gentle shaking, after which the blot was wrapped in plastic and exposed to film overnight at −80° C.

Figure 13:
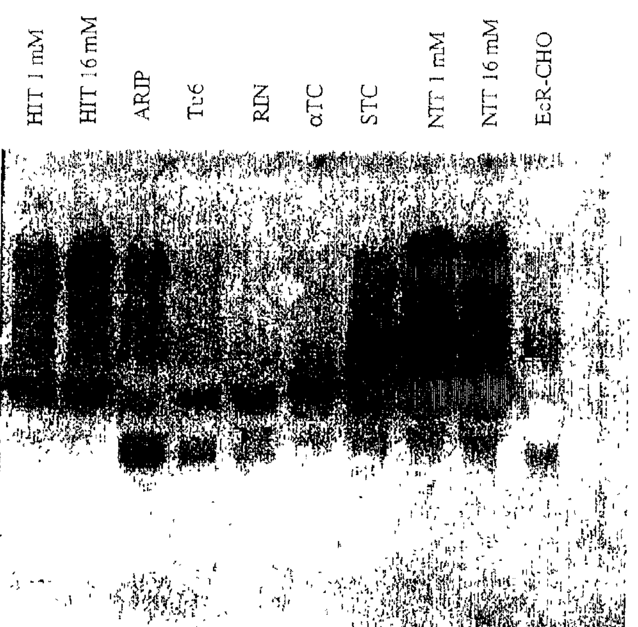
FIG. 13 a reproduction of a photograph of the results for the Northern Blot of GPR66 using multiple pancreatic cell lines.

Reference is made to FIG. 13. Results of RNA blots (see, FIG. 13) together with the dot-blot data, evidencing the expression of GPR66 in the pancreas, suggest that GPR66 is abundantly expressed in all islet cell lines and in ARIP cells, a pancreatic ductal cell lines. While not wishing to be bound by any theory, the expression of GPR66 in the pancreatic cell lines suggest that GPR66 may play a role in islet neogenesis.

c. GPR35

Total RNA from several cancer cell lines (e.g., RIN-5AH, HEP-G2, A549, HELA, MOLT-4, HL-60 and SW480 cells, all of which are commercially available) were isolated using TRIzol reagent (Gibco/BRL, Cat #15596-018) according to manufacturer's instructions. After electrophoreseis in a 1% agarose/formaldehyde gel, the RNA was transferred to a nylon membrane using standard protocols. A $^{32}$P-labelled GPR35 probe was synthesized using a DNA fragment corresponding precisely to the entire coding sequence and a Prime It II Random Primer Labeling Kit (Stratagene, Cat. #300385) according to manufacturer's instructions. Hybridization was performed using ExpressHyb Solution (Clontech, Cat.#8015-2) supplemented with 100 ug/ml salmon sperm DNA as follows. The membrane containing the separated RNA samples were first incubated with ExpressHyb solution at 65° C. for 1 hour. The $^{32}$P-labeled GPR35 DNA probe was denatured by boiling for 2 min, placed on ice for 5 min and then transferred into the ExpressHyb solution bathing the membrane. After an overnight incubation at 65° C., the membrane was removed from the hybridization and washed four times for 15 min each in 2×SSC/1% SDS at 65° C., followed by two washes for 15 min each in 0.1×SSC/0.5% SDS at 55° C. Excess moisture was removed from the blot by gentle shaking, after which the blot was wrapped in plastic and exposed to film overnight at −80° C.

Figure 15:
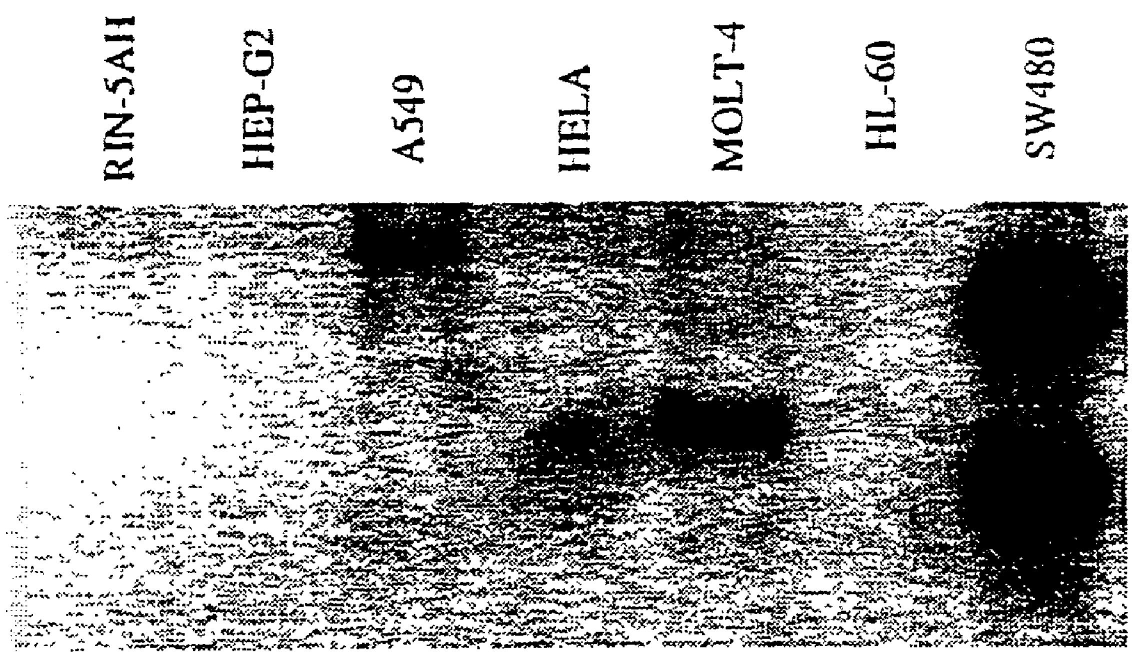
FIG. 15 is a reproduction of a photograph of the results for the Northern Blot of GPR35 using multiple tissue (human) cDNA.

Reference is made to FIG. 15. Results of RNA blots (see, FIG. 15) evidences that GPR35 is abundantly expressed in colorectal cancer cell line SW480. Such data suggests that GPR35 may play a role in colorectal carcinogenesis. Identification of candidate compounds, by the method discussed below, is most preferably an inverse agonist. An inverse agonist for GPR35 is intended to reduce DNA replication in an effort to inhibit cell proliferation of cancerous cells. GPR35 is expressed in large and small intestine. Numerous cancer cell lines were examined where GPR35 was determined to be expressed in the colorectal cancer cell line (e.g., HELA, MOLT-4 and SW480). This data suggests that GPR35 may play a role in colorectal carcinogenesis. Colorectal cancer is a malignancy that arises from either the colon or the rectum. Cancers of the large intestine are the second most common form of cancer found in both males and females.

d. ETBR-LP2

RNA from Example 6 was harvested utilizing RNAzol B reagent (TelTest Inc., Cat. #CS-104), according to manufacturer's instructions. After electrophoresis in an 1% agarose/formaldehyde gel, the RNA was transferred to a nylon membrane (Sachleicher Schull) by capillary action using 10× SSC. A $^{32}$P-labelled ETBR-LP2 DNA probe was synthesized using a DNA fragment corresponding precisely to the 3' end of ETBR-LP2 and a High Prime labeling kit (Roche Molecular Biochemical) according to the manufacturer's instructions. Hybridization was performed using ExpressHyb Solution (Clontech, Cat. #8015-2) supplemented with 100 μg/ml salmon sperm DNA as follows. The membrane containing the separated RNA samples was first incubated with ExpressHyb solution at 65° C. overnight. The $^{32}$P-labelled ETBR-LP2 DNA probe was denatured by boiling for 2 minutes, placed on ice for 5 minutes and then transferred into the ExpressHyb solution bathing the membrane. After an overnight incubation at 65° C., the membrane was removed from the hybridization solution and washed four times for 15 minutes each in 2×SSC/1% SDS at 65° C., followed by two washes for 15 minutes each in 0.2×SSC/0.1% SDS at 55° C. Excess moisture was removed from the blot by gentle shaking, after which the blot was wrapped in plastic wrap and exposed to film overnight at −80° C.

Figure 18:
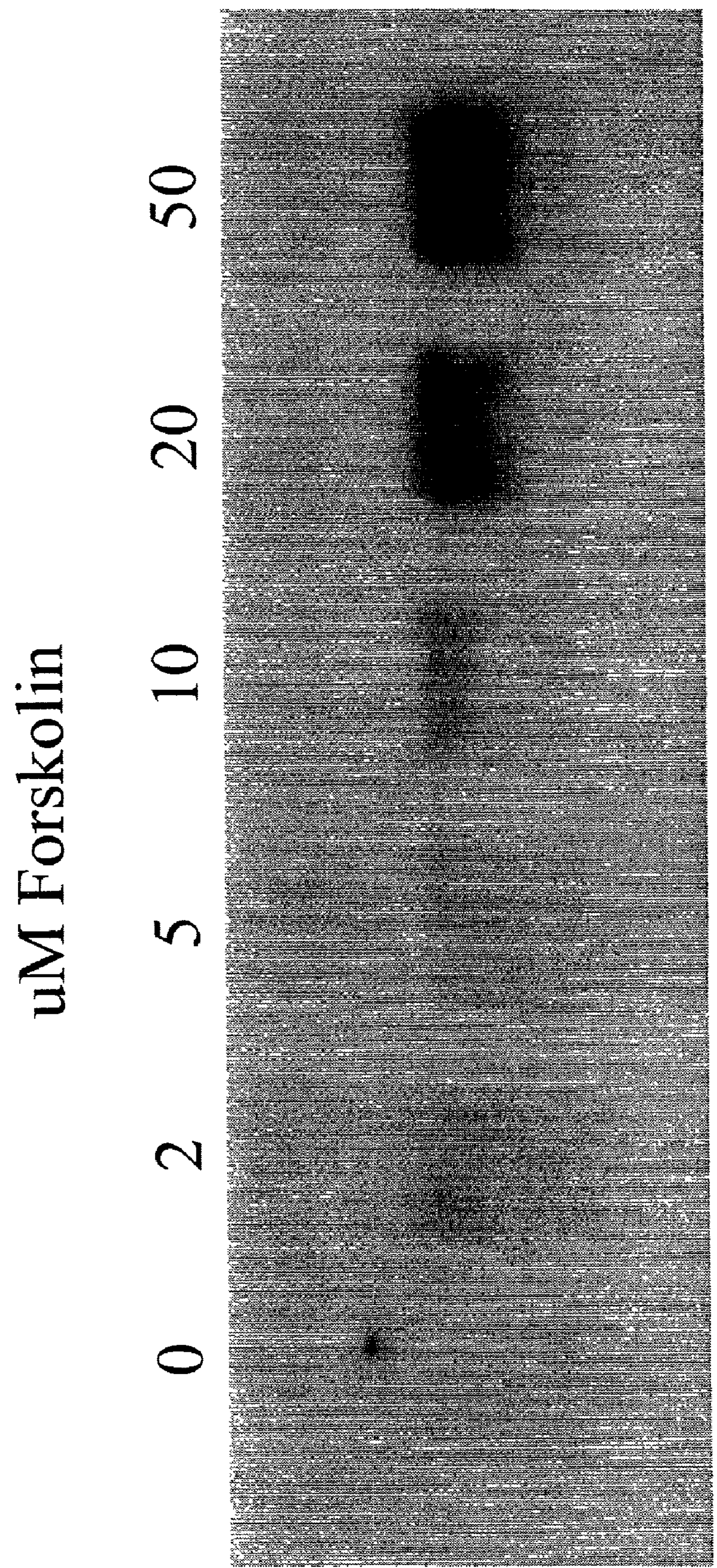
FIG. 18 is a representation of a Northern Analysis of ETBR-LP2 expressed in forskolin treated rat Schwann cells. Cell differentiation was maintained at 20 uM of forskolin.

Reference is made to FIG. 18. FIG. 18 evidences that ETBR-LP2 is expressed in Schwann cells, such that myelination can be maintained at 20 uM Forskolin.

Figure 19:
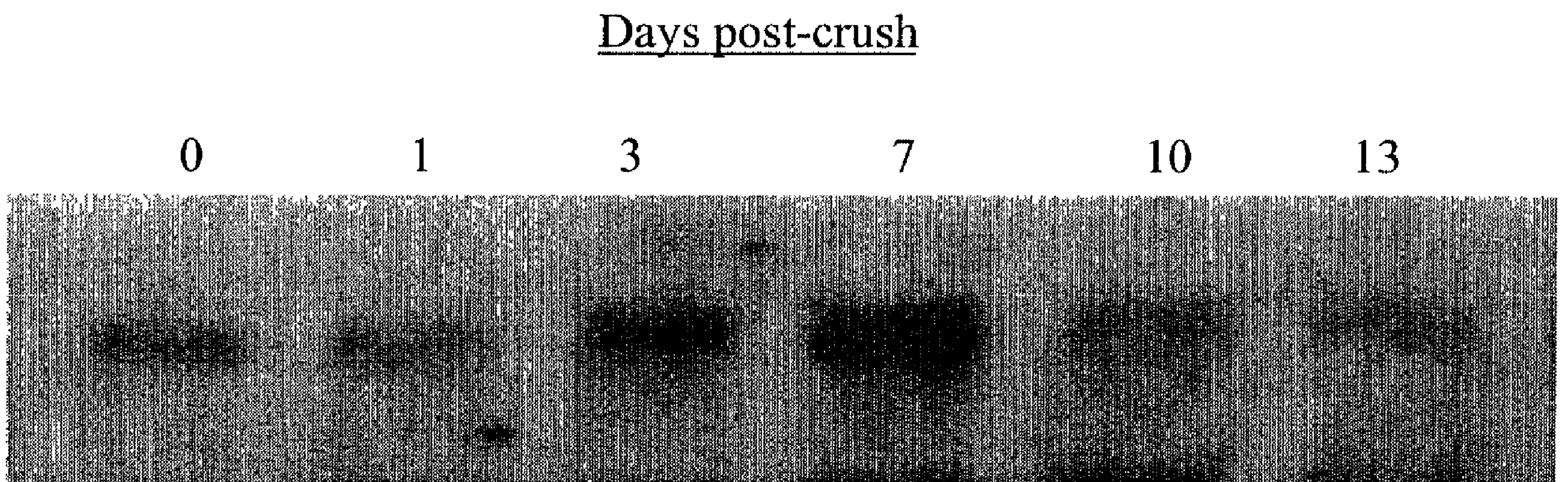
FIG. 19 is a representation of a Northern Analysis of ETBR-LP2 expressed in crushed rat sciatic nerve. ETBR-LP2 was highly up-regulated seven (7) days post crush.

Reference is made to FIG. 19. FIG. 19 evidences that ETBR-LP2 is up-regulated in crushed rat sciatic nerves, specifically seven (7) days after crushing the nerves. Such data is consistent with the data presented in FIG. 18, i.e., ETBR-LP2 may play a role in the regeneration of nerves by stimulating the process of myelination in Schwann cells.

Based upon these data, ETBR-LP2 is expressed in Schwann cells. When axons (or nerves) are injured, Schwann cells act to regenerate the nerves by forming myelin sheaths around the axons, which provides "insulation" in the form of myelin sheaths. This process, known as myelination, is important in that action potentials travel at a faster rate, thereby conserving metabolic energy. Schwann cells and their precursors play an important role in influencing the survival and differentiation of other cells that make up a pheripheral nerve. In addition, ETBR-LP2 has been determined to be expressed in crushed rat sciatic nerves. Such data supports the evidence that ETBR-LP2 may play a role in regenerating nerve cells. Based on the known functions of the specific tissues to which the receptor is localized, the putative functional role of the receptor can be deduced. Thus, in the case of hyper-myelination (e.g., tumorgenesis), an inverse agonist against ETBR-LP2 is preferred, while an agonist is preferred where hypo-myelination occurs (e.g., a degenerative disease such as diabetes).

Diseases and disorders related to receptors located in these tissues or regions include, but are not limited to, cardiac disorders and diseases (e.g. thrombosis, myocardial infarction; atherosclerosis; cardiomyopathies); kidney disease/disorders (e.g., renal failure; renal tubular acidosis; renal glycosuria; nephrogenic diabetes insipidus; cystinuria; polycystic kidney disease); eosinophilia; leukocytosis; leukopenia; ovarian cancer; sexual dysfunction; polycystic ovarian syndrome; pancreatitis and pancreatic cancer; irritable bowel syndrome; colon cancer; Crohn's disease; ulcerative colitis; diverticulitis; Chronic Obstructive Pulmonary Disease (COPD); Cystic Fibrosis; pneumonia; pulmonary hypertension; tuberculosis and lung cancer; Parkinson's disease; movement disorders and ataxias; learning and memory disorders; eating disorders (e.g., anorexia; bulimia, etc.); obesity; cancers; thymoma; myasthenia gravis; circulatory disorders; prostate cancer; prostatitis; kidney disease/disorders(e.g., renal failure; renal tubular acidosis; renal glycosuria; nephrogenic diabetes insipidus; cystinuria; polycystic kidney disease); sensorimotor processing and arousal disorders; obsessive-compulsive disorders; testicular cancer; priapism; prostatitis; hernia; endocrine disorders; sexual dysfunction; allergies; depression; psychotic disorders; migraine; reflux; schizophrenia; ulcers; bronchospasm; epilepsy; prostatic hypertrophy; anxiety; rhinitis; angina; and glaucoma. Accordingly, the methods of the present invention may also be useful in the diagnosis and/or treatment of these and other diseases and disorders.

Example 7

Protocol: Direct Identification of Inverse Agonists and Agonists

A. [$^{35}$S]GTPγS Assay

Although endogenous, constitutively active GPCRs have been used for the direct identification of candidate compounds as, e.g., inverse agonists, for reasons that are not altogether understood, intra-assay variation can become exacerbated. In some embodiments a GPCR Fusion Protein, as disclosed above, is also utilized with a non-endogenous, constitutively activated GPCR. When such a protein is used, intra-assay variation appears to be substantially stabilized, whereby an effective signal-to-noise ratio is obtained. This has the beneficial result of allowing for a more robust identification of candidate compounds. Thus, in some embodiments it is preferred that for direct identification, a GPCR Fusion Protein be used and that when utilized, the following assay protocols be utilized.

1. Membrane Preparation

Membranes comprising the constitutively active orphan GPCR Fusion Protein of interest and for use in the direct identification of candidate compounds as inverse agonists or agonists are preferably prepared as follows:

a. Materials

"Membrane Scrape Buffer" is comprised of 20 mM HEPES and 10 mM EDTA, pH 7.4; "Membrane Wash Buffer" is comprised of 20 mM HEPES and 0.1 mM EDTA, pH 7.4; "Binding Buffer" is comprised of 20 mM HEPES, 100 mM NaCl, and 10 mM $MgCl_2$, pH 7.4 b. Procedure

All materials will be kept on ice throughout the procedure. Firstly, the media will be aspirated from a confluent monolayer of cells, followed by rinse with 10 ml cold PBS, followed by aspiration. Thereafter, 5 ml of Membrane Scrape Buffer will be added to scrape cells; this will be followed by transfer of cellular extract into 50 ml centrifuge tubes (centrifuged at 20,000 rpm for 17 minutes at 4° C.). Thereafter, the supernatant will be aspirated and the pellet will be resuspended in 30 ml Membrane Wash Buffer followed by centrifugation at 20,000 rpm for 17 minutes at 4° C. The supernatant will then be aspirated and the pellet resuspended in Binding Buffer. The resuspended pellet will then be homogenized using a Brinkman Polytron™ homogenizer (15–20 second bursts until the material is in suspension). This is referred to herein as "Membrane Protein".

2. Bradford Protein Assay

Following the homogenization, protein concentration of the membranes will be determined, for example, using the Bradford Protein Assay (protein can be diluted to about 1.5 mg/ml, aliquoted and frozen (−80° C.) for later use; when frozen, protocol for use will be as follows: on the day of the assay, frozen Membrane Protein is thawed at room temperature, followed by vortex and then homogenized with a Polytron at about 12×1,000 rpm for about 5–10 seconds; it was noted that for multiple preparations, the homogenizer is thoroughly cleaned between homogenization of different preparations).

a. Materials

Binding Buffer (as discussed above); Bradford Dye Reagent; Bradford Protein Standard will be utilized, following manufacturer instructions (Biorad, cat. no. 500–0006).

b. Procedure

Duplicate tubes will be prepared, one including the membrane, and one as a control "blank". Each contains 800 μl Binding Buffer. Thereafter, 10 μof Bradford Protein Standard (1 mg/ml) will be added to each tube, and 10 μl of membrane Protein will then be added to just one tube (not the blank). Thereafter, 200 μl of Bradford Dye Reagent will be added to each tube, followed by vortexing. After five minutes, the tubes will be re-vortexed and the material therein will be transferred to cuvettes. The cuvettes will then be read using a CECIL 3041 spectrophotometer, at wavelength 595.

3. Direct Identification Assay a. Materials

GDP Buffer consisted of 37.5 ml Binding Buffer and 2 mg GDP (Sigma, cat. no. G-7127), followed by a series of dilutions in Binding Buffer to obtain 0.2 μM GDP (final concentration of GDP in each well was 0.1 μM GDP); each well comprising a candidate compound, has a final volume of 200 μl consisting of 100 μl GDP Buffer (final concentration, 0.1 μM GDP), 50 μl Membrane Protein in Binding Buffer, and 50 μl [$^{35}$S]GTPγS (0.6 nM) in Binding Buffer (2.5 μl [$^{35}$S]GTPγS per 10 ml Binding Buffer).

b. Procedure

Candidate compounds will be preferably screened using a 96-well plate format (these can be frozen at −80° C.). Membrane Protein (or membranes with expression vector excluding the GPCR Fusion Protein, as control), will be homogenized briefly until in suspension. Protein concentration will then be determined using, for example, the Bradford Protein Assay set forth above. Membrane Protein (and controls) will then be diluted to 0.25 mg/ml in Binding Buffer (final assay concentration, 12.5 μg/well). Thereafter, 100 μl GDP Buffer is added to each well of a Wallac Scintistrip™ (Wallac). A 5 μl pin-tool will then be used to transfer 5 μl of a candidate compound into such well (i.e., 5 μl in total assay volume of 200 μl is a 1:40 ratio such that the final screening concentration of the candidate compound is 10 μM). Again, to avoid contamination, after each transfer step the pin tool is rinsed in three reservoirs comprising water (1×), ethanol (1×) and water (2×)—excess liquid is shaken from the tool after each rinse and the tool is dried with paper and Kim wipes. Thereafter, 50 μl of Membrane Protein will be added to each well (a control well comprising membranes without the GPCR Fusion Protein was also utilized), and pre-incubated for 5–10 minutes at room temperature. Thereafter, 50 μl of [$^{35}$S]GTPγS (0.6 nM) in Binding Buffer will be added to each well, followed by incubation on a shaker for 60 minutes at room temperature (again, in this example, plates were covered with foil). The assay will be stopped by spinning the plates at 4000 RPM for 15 minutes at 22° C. The plates will then be aspirated with an 8 channel manifold and sealed with plate covers. The plates will then be read on a Wallac 1450 using setting "Prot. #37" (as per manufacturer's instructions).

B. Cyclic AMP Assay

Another assay approach to directly identify candidate compound will be accomplished utilizing a cyclase-based assay. In addition to direct identification, this assay approach can be utilized as an independent approach to provide confirmation of the results from the [$^{35}$S]GTPγS approach as set forth above.

A modified Flash Plate™ Adenylyl Cyclase kit (New England Nuclear; Cat. No. SMP004A) will be preferably utilized for direct identification of candidate compounds as inverse agonists and agonists to GPCRs in accordance with the following protocol.

Transfected cells will be harvested approximately three days after transfection. Membranes will be prepared by homogenization of suspended cells in buffer containing 20 mM HEPES, pH 7.4 and 10 mM $MgCl_2$. Homogenization will be performed on ice using a Brinkman Polytron™ for approximately 10 seconds. The resulting homogenate will be centrifuged at 49,000×g for 15 minutes at 4° C. The resulting pellet will then be resuspended in buffer containing 20 mM HEPES, pH 7.4 and 0.1 mM EDTA, homogenized for 10 seconds, followed by centrifugation at 49,000×g for 15 minutes at 4° C. The resulting pellet will then be stored at −80° C. until utilized. On the day of direct identification screening, the membrane pellet will slowly be thawed at room temperature, resuspended in buffer containing 20 mM HEPES, pH 7.4 and 10 mM $MgCl_2$, to yield a final protein concentration of 0.60 mg/ml (the resuspended membranes will be placed on ice until use).

cAMP standards and Detection Buffer (comprising 2 μCi of tracer [$^{125}$I cAMP (100 μl] to 11 ml Detection Buffer) will be prepared and maintained in accordance with the manufacturer's instructions. Assay Buffer will be prepared fresh for screening and contain 20 mM HEPES, pH 7.4, 10 mM $MgCl_2$, 20 mM phosphocreatine (Sigma), 0.1 units/ml creatine phosphokinase (Sigma), 50 μM GTP (Sigma), and 0.2 mM ATP (Sigma); Assay Buffer will be stored on ice until utilized.

Candidate compounds identified as per above (if frozen, thawed at room temperature) will be added, preferably, to 96-well plate wells (3 μl/well; 12 μM final assay concentration), together with 40 μl Membrane Protein (30 μg/well) and 50 μl of Assay Buffer. This admixture will be incubated for 30 minutes at room temperature, with gentle shaking.

Following the incubation, 100 μl of Detection Buffer will be added to each well, followed by incubation for 2–24 hours. Plates will then be counted in a Wallac MicroBeta™ plate reader using "Prot. #31" (as per manufacturer instructions).

C. Melanophore Screening Assay

A method for identifying candidate agonists or inverse agonists for a GPCR can be preformed by introducing tests cells of a pigment cell line capable of dispersing or aggregating their pigment in response to a specific stimulus and expressing an exogenous clone coding for the GCPR. A stimulant, e.g., light, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The tests cells are then contacted with chemical compounds, and it is determined whether the pigment disposition in the cells changed from the initial state of pigment disposition. Dispersion of pigments cells due to the candidate compound coupling to the GPCR will appear dark on a petri dish, while aggregation of pigments cells will appear light.

Materials and methods will be followed according to the disclosure of U.S. Pat. Nos. 5,462,856 and 6,051,386, each of which are incorporated by reference in its entirety.

Although a variety of expression vectors are available to those in the art, for purposes of utilization for both the endogenous and non-endogenous human GPCRs, in some embodiments it is preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

References cited throughout this patent document, including co-pending and related patent applications, unless otherwise indicated, are fully incorporated herein by reference. Modifications and extension of the disclosed inventions that are within the purview of the skilled artisan are encompassed within the above disclosure and the claims that follow.

What is claimed is:

1. An isolated polynucleotide encoding a non-endogenous, constitutively activated version of a wild-type G protein-coupled receptor, wherein the wild-type G protein-coupled receptor comprises SEQ. ID.: 16 and wherein said non-endogenous constitutively activated version contains a mutation of an amino acid residue located 16 amino acid residues from a proline residue in TM6.

2. An isolated polynucleotide encoding a non-endogenous, constitutively activated version of a wild-type G protein-coupled receptor, wherein the wild-type G protein-coupled receptor comprises SEQ. ID. NO.: 16, and wherein said polynucleotide encodes an amino avid sequence that comprises.

3. An isolated polynucleotide according to claim 2, wherein the polynucleotide comprises.

4. A vector comprising a polynucleotide according to any one of claims 1 to 3.

5. A vector according to claim 4, wherein said vector is an expression vector.

6. A host cell comprising an expression vector according to claim 5.

7. A process for making a recombinant host cell comprising the steps of:

(a) transfecting an expression vector according to claim 5 into a suitable host cell; and (b) culturing the host cell under conditions which allow expression of a G protein-coupled receptor from the expression vector.

8. A membrane of a recombinant host cell produced by the process of claim 7 comprising said G protein-coupled receptor.

* * * * *

UNITED STATES PATENT AND TRADEMARK OFFICE

CERTIFICATE OF CORRECTION

PATENT NO. : 7,119,190 B2
APPLICATION NO. : 10/083168
DATED : October 10, 2006
INVENTOR(S) : Chen W. Liaw et al.

It is certified that error appears in the above-identified patent and that said Letters Patent is hereby corrected as shown below:

Claim 1: “SEQ. ID.: 16” should read as --SEQ. ID. NO.: 16--.

Claim 2: please correct to read --An isolated polynucleotide encoding a non-endogenous constitutively activated version of a wild-type G protein-couple receptor, wherein the wild-type G protein-coupled receptor comprises SEQ. ID. NO.:16 and wherein said polynucleotide encodes an amino acid sequence that comprises SEQ. ID. NO. 85.--

Claim 3: please correct to read: --An isolated polynucleotide according to claim 2, wherein the polynucleotide comprises SEQ. ID. No.: 84.--

Signed and Sealed this

Third Day of April, 2007

JON W. DUDAS

*Director of the United States Patent and Trademark Office*

SEQUENCE LISTING

```
<160> NUMBER OF SEQ ID NOS: 102

<210> SEQ ID NO 1
<211> LENGTH: 1062
<212> TYPE: DNA
<213> ORGANISM: Homo sapiens

<400> SEQUENCE: 1

atggaaacca acttctccat tcctctgaat gaaactgagg aggtgctccc tgagcctgct      60

ggccacaccg ttctgtggat cttctcattg ctagtccacg gagtcacctt tgtcttcggg     120

gtcctgggca atgggcttgt gatctgggtg gctggattcc ggatgacacg cacagtcaac     180

accatctgtt acctgaacct ggccctagct gacttctctt tcagtgccat cctaccattc     240

cgaatggtct cagtcgccat gagagaaaaa tggccttttg gctcattcct atgtaagtta     300
```

-continued

```
gttcatgtta tgatagacat caacctgttt gtcagtgtct acctgatcac catcattgct    360

ctggaccgct gtatttgtgt cctgcatcca gcctgggccc agaaccatcg caccatgagt    420

ctggccaaga gggtgatgac gggactctgg attttcacca tagtccttac cttaccaaat    480

ttcatcttct ggactacaat aagtactacg aatggggaca catactgtat tttcaacttt    540

gcattctggg gtgacactgc tgtagagagg ttgaacgtgt tcattaccat ggccaaggtc    600

tttctgatcc tccacttcat tattggcttc agcgtgccta tgtccatcat cacagtctgc    660

tatgggatca tcgctgccaa aattcacaga aaccacatga ttaaatccag ccgtccctta    720

cgtgtcttcg ctgctgtggt ggcttctttc ttcatctgtt ggttccctta tgaactaatt    780

ggcattctaa tggcagtctg gctcaaagag atgttgttaa atggcaaata caaaatcatt    840

cttgtcctga ttaacccaac aagctccttg gccttttta acagctgcct caacccaatt    900

ctctacgtct ttatgggtcg taacttccaa gaaagactga ttcgctcttt gcccactagt    960

ttggagaggg ccctgactga ggtccctgac tcagcccaga ccagcaacac agacaccact   1020

tctgcttcac ctcctgagga gacggagtta caagcaatgt ga                      1062
```

<210> SEQ ID NO 2
<211> LENGTH: 353
<212> TYPE: PRT
<213> ORGANISM: Homo sapiens

<400> SEQUENCE: 2

```
Met Glu Thr Asn Phe Ser Ile Pro Leu Asn Glu Thr Glu Glu Val Leu
1               5                   10                  15

Pro Glu Pro Ala Gly His Thr Val Leu Trp Ile Phe Ser Leu Leu Val
            20                  25                  30

His Gly Val Thr Phe Val Phe Gly Val Leu Gly Asn Gly Leu Val Ile
        35                  40                  45

Trp Val Ala Gly Phe Arg Met Thr Arg Thr Val Asn Thr Ile Cys Tyr
    50                  55                  60

Leu Asn Leu Ala Leu Ala Asp Phe Ser Phe Ser Ala Ile Leu Pro Phe
65                  70                  75                  80

Arg Met Val Ser Val Ala Met Arg Glu Lys Trp Pro Phe Gly Ser Phe
                85                  90                  95

Leu Cys Lys Leu Val His Val Met Ile Asp Ile Asn Leu Phe Val Ser
            100                 105                 110

Val Tyr Leu Ile Thr Ile Ile Ala Leu Asp Arg Cys Ile Cys Val Leu
        115                 120                 125

His Pro Ala Trp Ala Gln Asn His Arg Thr Met Ser Leu Ala Lys Arg
    130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
            180                 185                 190

Val Phe Ile Thr Met Ala Lys Val Phe Leu Ile Leu His Phe Ile Ile
        195                 200                 205

Gly Phe Ser Val Pro Met Ser Ile Ile Thr Val Cys Tyr Gly Ile Ile
    210                 215                 220

Ala Ala Lys Ile His Arg Asn His Met Ile Lys Ser Ser Arg Pro Leu
225                 230                 235                 240
```

-continued

```
Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
            260                 265                 270

Leu Asn Gly Lys Tyr Lys Ile Ile Leu Val Leu Ile Asn Pro Thr Ser
        275                 280                 285

Ser Leu Ala Phe Phe Asn Ser Cys Leu Asn Pro Ile Leu Tyr Val Phe
    290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr Asp Thr Thr Ser Ala Ser Pro Pro Glu Glu Thr Glu Leu Gln Ala
            340                 345                 350

Met


<210> SEQ ID NO 3
<211> LENGTH: 1029
<212> TYPE: DNA
<213> ORGANISM: Homo sapiens

<400> SEQUENCE: 3

atggcagagc atgattacca tgaagactat gggttcagca gtttcaatga cagcagccag      60

gaggagcatc aagccttcct gcagttcagc aaggtctttc tgccctgcat gtacctggtg     120

gtgtttgtct gtggtctggt ggggaactct ctggtgctgg tcatatccat cttctaccat     180

aagttgcaga gcctgacgga tgtgttcctg gtgaacctac ccctggctga cctggtgttt     240

gtctgcactc tgcccttctg ggcctatgca ggcatccatg aatgggtgtt tggccaggtc     300

atgtgcaaaa gcctactggg catctacact attaacttct acacgtccat gctcatcctc     360

acctgcatca ctgtggatcg tttcattgta gtggttaagg ccaccaaggc ctacaaccag     420

caagccaaga ggatgacctg gggcaaggtc accagcttgc tcatctgggt gatatccctg     480

ctggtttcct tgccccaaat tatctatggc aatgtcttta atctcgacaa gctcatatgt     540

ggttaccatg acgaggcaat ttccactgtg gttcttgcca cccagatgac actggggttc     600

ttcttgccac tgctcaccat gattgtctgc tattcagtca taatcaaaac actgcttcat     660

gctggaggct tccagaagca cagatctcta aagatcatct tcctggtgat ggctgtgttc     720

ctgctgaccc agatgccctt caacctcatg aagttcatcc gcagcacaca ctgggaatac     780

tatgccatga ccagctttca ctacaccatc atggtgacag aggccatcgc atacctgagg     840

gcctgcctta accctgtgct ctatgccttt gtcagcctga agtttcgaaa gaacttctgg     900

aaacttgtga aggacattgg ttgcctccct taccttgggg tctcacatca atggaaatct     960

tctgaggaca attccaagac tttttctgcc tcccacaatg tggaggccac cagcatgttc    1020

cagttatag                                                            1029


<210> SEQ ID NO 4
<211> LENGTH: 342
<212> TYPE: PRT
<213> ORGANISM: Homo sapiens

<400> SEQUENCE: 4

Met Ala Glu His Asp Tyr His Glu Asp Tyr Gly Phe Ser Ser Phe Asn
1               5                   10                  15

Asp Ser Ser Gln Glu Glu His Gln Ala Phe Leu Gln Phe Ser Lys Val
```

-continued

```
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340
```

<210> SEQ ID NO 5
<211> LENGTH: 1119
<212> TYPE: DNA
<213> ORGANISM: Homo sapiens

<400> SEQUENCE: 5

```
atggcctgca acagcacgtc ccttgaggct tacacatacc tgctgctgaa caccagcaac     60

gcctcagact cggggtccac ccagttgccc gcacccctca ggatctcctt ggccatagtg    120

atgctgctga tgaccgtggt ggggttcctg ggcaacactg tggtctgcat catcgtgtac    180

cagaggccgg ctatgcgctc ggccatcaac ctgctgctgg ccaccctggc cttctccgac    240

atcatgctgt ccctctgctg catgcccttc accgccgtca ccctcatcac cgtgcgctgg    300
```

-continued

```
cactttgggg accacttctg ccgcctctca gccacgctct actggttttt tgtcctggag     360

ggcgtggcca tcctgctcat catcagcgtg gaccgcttcc tcatcatcgt ccagcgccag     420

gacaagctga acccgcgcag ggccaaggtg atcatcgcgg tctcctgggt gctgtccttc     480

tgcatcgcgg ggccctcgct cacgggctgg acgctggtgg aggtgccggc gcgggcccca     540

cagtgcgtgc tgggctacac ggagctcccc gctgaccgcg catacgtggt caccttggtg     600

gtggccgtgt tcttcgcgcc ctttggcgtc atgctgtgcg cctacatgtg catcctcaac     660

acggtccgca agaacgccgt gcgcgtgcac aaccagtcgg acagcctgga cctgcggcag     720

ctcaccaggg cgggcctgcg gcgcctgcag cggcagcaac aggtcagcgt ggacttgagc     780

ttcaagacca aggccttcac caccatcctg atcctcttcg tgggcttctc cctctgctgg     840

ctgccccact ccgtctacag cctcctgtct gtgtttagcc agcgctttta ctgcggttcc     900

tccttctacg ccaccagcac ctgcgtcctg tggttcagtt acctcaagtc cgtcttcaac     960

cccatcgtct actgctggag aatcaaaaaa ttccgcgagg cctgcataga gttgctgccc    1020

cagaccttcc aaatcctccc caaagtgcct gagcggatcc gaaggagaat ccagccaagc    1080

acagtatacg tgtgcaatga aaaccagtct gcggtttag                           1119


<210> SEQ ID NO 6
<211> LENGTH: 372
<212> TYPE: PRT
<213> ORGANISM: Homo sapiens

<400> SEQUENCE: 6

Met Ala Cys Asn Ser Thr Ser Leu Glu Ala Tyr Thr Tyr Leu Leu Leu
1               5                   10                  15

Asn Thr Ser Asn Ala Ser Asp Ser Gly Ser Thr Gln Leu Pro Ala Pro
            20                  25                  30

Leu Arg Ile Ser Leu Ala Ile Val Met Leu Leu Met Thr Val Val Gly
        35                  40                  45

Phe Leu Gly Asn Thr Val Val Cys Ile Ile Val Tyr Gln Arg Pro Ala
    50                  55                  60

Met Arg Ser Ala Ile Asn Leu Leu Leu Ala Thr Leu Ala Phe Ser Asp
65                  70                  75                  80

Ile Met Leu Ser Leu Cys Cys Met Pro Phe Thr Ala Val Thr Leu Ile
                85                  90                  95

Thr Val Arg Trp His Phe Gly Asp His Phe Cys Arg Leu Ser Ala Thr
            100                 105                 110

Leu Tyr Trp Phe Phe Val Leu Glu Gly Val Ala Ile Leu Leu Ile Ile
        115                 120                 125

Ser Val Asp Arg Phe Leu Ile Ile Val Gln Arg Gln Asp Lys Leu Asn
    130                 135                 140

Pro Arg Arg Ala Lys Val Ile Ile Ala Val Ser Trp Val Leu Ser Phe
145                 150                 155                 160

Cys Ile Ala Gly Pro Ser Leu Thr Gly Trp Thr Leu Val Glu Val Pro
                165                 170                 175

Ala Arg Ala Pro Gln Cys Val Leu Gly Tyr Thr Glu Leu Pro Ala Asp
            180                 185                 190

Arg Ala Tyr Val Val Thr Leu Val Val Ala Val Phe Phe Ala Pro Phe
        195                 200                 205

Gly Val Met Leu Cys Ala Tyr Met Cys Ile Leu Asn Thr Val Arg Lys
    210                 215                 220
```

-continued

```
Asn Ala Val Arg Val His Asn Gln Ser Asp Ser Leu Asp Leu Arg Gln
225                 230                 235                 240

Leu Thr Arg Ala Gly Leu Arg Arg Leu Gln Arg Gln Gln Gln Val Ser
                245                 250                 255

Val Asp Leu Ser Phe Lys Thr Lys Ala Phe Thr Thr Ile Leu Ile Leu
            260                 265                 270

Phe Val Gly Phe Ser Leu Cys Trp Leu Pro His Ser Val Tyr Ser Leu
        275                 280                 285

Leu Ser Val Phe Ser Gln Arg Phe Tyr Cys Gly Ser Ser Phe Tyr Ala
    290                 295                 300

Thr Ser Thr Cys Val Leu Trp Phe Ser Tyr Leu Lys Ser Val Phe Asn
305                 310                 315                 320

Pro Ile Val Tyr Cys Trp Arg Ile Lys Lys Phe Arg Glu Ala Cys Ile
                325                 330                 335

Glu Leu Leu Pro Gln Thr Phe Gln Ile Leu Pro Lys Val Pro Glu Arg
            340                 345                 350

Ile Arg Arg Arg Ile Gln Pro Ser Thr Val Tyr Val Cys Asn Glu Asn
        355                 360                 365

Gln Ser Ala Val
    370


<210> SEQ ID NO 7
<211> LENGTH: 2748
<212> TYPE: DNA
<213> ORGANISM: Homo sapiens

<400> SEQUENCE: 7

atggtccagc tgaggaagct gctccgcgtc ctgactttga tgaagttccc ctgctgcgtg      60

ctggaggtgc tcctgtgcgc gctggcggcg gcggcgcgcg gccaggagat gtacgccccg     120

cactcaatcc ggatcgaggg ggacgtcacc ctcggggggc tgttccccgt gcacgccaag     180

ggtcccagcg gagtgccctg cggcgacatc aagagggaaa acgggatcca caggctggaa     240

gcgatgctct acgccctgga ccagatcaac agtgatccca acctactgcc caacgtgacg     300

ctgggcgcgc ggatcctgga cacttgttcc agggacactt acgcgctcga acagtcgctt     360

actttcgtcc aggcgctcat ccagaaggac acctccgacg tgcgctgcac caacggcgaa     420

ccgccggttt tcgtcaagcc ggagaaagta gttggagtga ttggggcttc ggggagttcg     480

gtctccatca tggtagccaa catcctgagg ctcttccaga tcccccagat tagttatgca     540

tcaacggcac ccgagctaag tgatgaccgg cgctatgact tcttctctcg cgtggtgcca     600

cccgattcct tccaagccca ggccatggta gacattgtaa aggccctagg ctggaattat     660

gtgtctaccc tcgcatcgga aggaagttat ggagagaaag gtgtggagtc cttcacgcag     720

atttccaaag aggcaggtgg actctgcatt gcccagtccg tgagaatccc ccaggaacgc     780

aaagacagga ccattgactt tgatagaatt atcaaacagc tcctggacac ccccaactcc     840

agggccgtcg tgatttttgc caacgatgag gatataaagc agatccttgc agcagccaaa     900

agagctgacc aagttggcca ttttctttgg gtgggatcag acagctgggg atccaaaata     960

aacccactgc accagcatga agatatcgca gaaggggcca tcaccattca gcccaagcga    1020

gccacggtgg aagggtttga tgcctacttt acgtcccgta cacttgaaaa caacagaaga    1080

aatgtatggt ttgccgaata ctgggaggaa aacttcaact gcaagttgac gattagtggg    1140

tcaaaaaaag aagacacaga tcgcaaatgc acaggacagg agagaattgg aaaagattcc    1200

aactatgagc aggagggtaa agtccagttc gtgattgacg cagtctatgc tatggctcac    1260
```

```
gcccttcacc acatgaacaa ggatctctgt gctgactacc ggggtgtctg cccagagatg   1320

gagcaagctg gaggcaagaa gttgctgaag tatatacgca atgttaattt caatggtagt   1380

gctggcactc cagtgatgtt taacaagaac ggggatgcac ctgggcgtta tgacatcttt   1440

cagtaccaga ccacaaacac cagcaacccg ggttaccgtc tgatcgggca gtggacagac   1500

gaacttcagc tcaatataga agacatgcag tggggtaaag gagtccgaga gatacccgcc   1560

tcagtgtgca cactaccatg taagccagga cagagaaaga agacacagaa aggaactcct   1620

tgctgttgga cctgtgagcc ttgcgatggt taccagtacc agtttgatga gatgacatgc   1680

cagcattgcc cctatgacca gaggcccaat gaaaatcgaa ccggatgcca ggatattccc   1740

atcatcaaac tggagtggca ctccccctgg gctgtgattc ctgtcttcct ggcaatgttg   1800

gggatcattg ccaccatctt tgtcatggcc actttcatcc gctacaatga cacgcccatt   1860

gtccgggcat ctgggcggga actcagctat gttcttttga cgggcatctt tctttgctac   1920

atcatcactt tcctgatgat tgccaaacca gatgtggcag tgtgttcttt ccggcgagtt   1980

ttcttgggct tgggtatgtg catcagttat gcagccctct tgacgaaaac aaatcggatt   2040

tatcgcatat ttgagcaggg caagaaatca gtaacagctc ccagactcat aagcccaaca   2100

tcacaactgg caatcacttc cagtttaata tcagttcagc ttctaggggt gttcatttgg   2160

tttggtgttg atccacccaa catcatcata gactacgatg aacacaagac aatgaaccct   2220

gagcaagcca gaggggttct caagtgtgac attacagatc tccaaatcat ttgctccttg   2280

ggatatagca ttcttctcat ggtcacatgt actgtgtatg ccatcaagac tcggggtgta   2340

cccgagaatt ttaacgaagc caagcccatt ggattcacta tgtacacgac atgtatagta   2400

tggcttgcct tcattccaat ttttttggc accgctcaat cagcggaaaa gctctacata   2460

caaactacca cgcttacaat ctccatgaac ctaagtgcat cagtggcgct ggggatgcta   2520

tacatgccga aagtgtacat catcattttc caccctgaac tcaatgtcca gaaacggaag   2580

cgaagcttca aggcggtagt cacagcagcc accatgtcat cgaggctgtc acacaaaccc   2640

agtgacagac ccaacggtga ggcaaagacc gagctctgtg aaaacgtaga cccaaacagc   2700

cctgctgcaa aaaagaagta tgtcagttat aataacctgg ttatctaa                 2748
```

```
<210> SEQ ID NO 8
<211> LENGTH: 915
<212> TYPE: PRT
<213> ORGANISM: Homo sapiens

<400> SEQUENCE: 8

Met Val Gln Leu Arg Lys Leu Leu Arg Val Leu Thr Leu Met Lys Phe
1               5                   10                  15

Pro Cys Cys Val Leu Glu Val Leu Leu Cys Ala Leu Ala Ala Ala Ala
            20                  25                  30

Arg Gly Gln Glu Met Tyr Ala Pro His Ser Ile Arg Ile Glu Gly Asp
        35                  40                  45

Val Thr Leu Gly Gly Leu Phe Pro Val His Ala Lys Gly Pro Ser Gly
    50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
            100                 105                 110
```

-continued

```
Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
    130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350

Arg Thr Leu Glu Asn Asn Arg Arg Asn Val Trp Phe Ala Glu Tyr Trp
        355                 360                 365

Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
            420                 425                 430

Tyr Arg Gly Val Cys Pro Glu Met Glu Gln Ala Gly Gly Lys Lys Leu
        435                 440                 445

Leu Lys Tyr Ile Arg Asn Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                485                 490                 495

Gln Trp Thr Asp Glu Leu Gln Leu Asn Ile Glu Asp Met Gln Trp Gly
            500                 505                 510

Lys Gly Val Arg Glu Ile Pro Ala Ser Val Cys Thr Leu Pro Cys Lys
        515                 520                 525
```

-continued

```
Pro Gly Gln Arg Lys Lys Thr Gln Lys Gly Thr Pro Cys Cys Trp Thr
    530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Trp Ala Val
            580                 585                 590

Ile Pro Val Phe Leu Ala Met Leu Gly Ile Ile Ala Thr Ile Phe Val
        595                 600                 605

Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
        675                 680                 685

Lys Ser Val Thr Ala Pro Arg Leu Ile Ser Pro Thr Ser Gln Leu Ala
    690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
        755                 760                 765

Thr Cys Thr Val Tyr Ala Ile Lys Thr Arg Gly Val Pro Glu Asn Phe
    770                 775                 780

Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
        835                 840                 845

Ile Phe His Pro Glu Leu Asn Val Gln Lys Arg Lys Arg Ser Phe Lys
    850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Ser Pro Ala Ala Lys Lys Lys Tyr Val Ser Tyr Asn Asn
            900                 905                 910

Leu Val Ile
        915
```

<210> SEQ ID NO 9
<211> LENGTH: 1842
<212> TYPE: DNA

<213> ORGANISM: Homo sapiens

<400> SEQUENCE: 9

```
atgcgagccc cgggcgcgct tctcgcccgc atgtcgcggc tactgcttct gctactgctc      60
aaggtgtctg cctcttctgc cctcggggtc gcccctgcgt ccagaaacga aacttgtctg     120
ggggagagct gtgcacctac agtgatccag cgccgcggca gggacgcctg gggaccggga     180
aattctgcaa gagacgttct gcgagcccga gcacccaggg aggagcaggg ggcagcgttt     240
cttgcgggac cctcctggga cctgccggcg gccccgggcc gtgacccggc tgcaggcaga     300
ggggcggagg cgtcggcagc cggacccccg ggacctccaa ccaggccacc tggcccctgg     360
aggtggaaag gtgctcgggg tcaggagcct tctgaaactt tggggagagg gaaccccacg     420
gccctccagc tcttccttca gatctcagag gaggaagaga agggtcccag aggcgctggc     480
atttccgggc gtagccagga gcagagtgtg aagacagtcc ccggagccag cgatcttttt     540
tactggccaa ggagagccgg gaaactccag ggttcccacc acaagcccct gtccaagacg     600
gccaatggac tggcggggca cgaagggtgg acaattgcac tcccgggccg ggcgctggcc     660
cagaatggat ccttgggtga aggaatccat gagcctgggg gtccccgccg gggaaacagc     720
acgaaccggc gtgtgagact gaagaacccc ttctacccgc tgacccagga gtcctatgga     780
gcctacgcgg tcatgtgtct gtccgtggtg atcttcggga ccggcatcat tggcaacctg     840
gcggtgatgt gcatcgtgtg ccacaactac tacatgcgga gcatctccaa ctccctcttg     900
gccaacctgg ccttctggga ctttctcatc atcttcttct gccttccgct ggtcatcttc     960
cacgagctga ccaagaagtg gctgctggag gacttctcct gcaagatcgt gccctatata    1020
gaggtcgctt ctctgggagt caccaccttc accttatgtg ctctgtgcat agaccgcttc    1080
cgtgctgcca ccaacgtaca gatgtactac gaaatgatcg aaaactgttc ctcaacaact    1140
gccaaacttg ctgttatatg ggtgggagct ctattgttag cacttccaga agttgttctc    1200
cgccagctga gcaaggagga tttggggttt agtggccgag ctccggcaga aaggtgcatt    1260
attaagatct ctcctgattt accagacacc atctatgttc tagccctcac ctacgacagt    1320
gcgagactgt ggtggtattt tggctgttac ttttgtttgc ccacgctttt caccatcacc    1380
tgctctctag tgactgcgag gaaaatccgc aaagcagaga aagcctgtac ccgagggaat    1440
aaacggcaga ttcaactaga gagtcagatg aactgtacag tagtggcact gaccatttta    1500
tatggatttt gcattattcc tgaaaatatc tgcaacattg ttactgccta catggctaca    1560
ggggtttcac agcagacaat ggacctcctt aatatcatca gccagttcct tttgttcttt    1620
aagtcctgtg tcaccccagt cctccttttc tgtctctgca aacccttcag tcgggccttc    1680
atggagtgct gctgctgttg ctgtgaggaa tgcattcaga agtcttcaac ggtgaccagt    1740
gatgacaatg acaacgagta caccacggaa ctcgaactct cgcctttcag taccatacgc    1800
cgtgaaatgt ccacttttgc ttctgtcgga actcattgct ga                       1842
```

<210> SEQ ID NO 10
<211> LENGTH: 613
<212> TYPE: PRT
<213> ORGANISM: Homo sapiens

<400> SEQUENCE: 10

```
Met Arg Ala Pro Gly Ala Leu Leu Ala Arg Met Ser Arg Leu Leu Leu
1               5                   10                  15

Leu Leu Leu Leu Lys Val Ser Ala Ser Ser Ala Leu Gly Val Ala Pro
            20                  25                  30
```

-continued

```
Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110

Pro Thr Arg Pro Pro Gly Pro Trp Arg Trp Lys Gly Ala Arg Gly Gln
        115                 120                 125

Glu Pro Ser Glu Thr Leu Gly Arg Gly Asn Pro Thr Ala Leu Gln Leu
    130                 135                 140

Phe Leu Gln Ile Ser Glu Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Cys Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
305                 310                 315                 320

His Glu Leu Thr Lys Lys Trp Leu Leu Glu Asp Phe Ser Cys Lys Ile
                325                 330                 335

Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445
```

-continued

```
Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Asn Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610
```

<210> SEQ ID NO 11
<211> LENGTH: 1086
<212> TYPE: DNA
<213> ORGANISM: Homo sapiens

<400> SEQUENCE: 11

```
atgtcccctg aatgcgcgcg ggcagcgggc gacgcgccct tgcgcagcct ggagcaagcc      60

aaccgcaccc gctttccctt cttctccgac gtcaagggcg accaccggct ggtgctggcc     120

gcggtggaga caaccgtgct ggtgctcatc tttgcagtgt cgctgctggg caacgtgtgc     180

gccctggtgc tggtggcgcg ccgacgacgc cgcggcgcga ctgcctgcct ggtactcaac     240

ctcttctgcg cggacctgct cttcatcagc gctatccctc tggtgctggc cgtgcgctgg     300

actgaggcct ggctgctggg ccccgttgcc tgccacctgc tcttctacgt gatgaccctg     360

agcggcagcg tcaccatcct cacgctggcc gcggtcagcc tggagcgcat ggtgtgcatc     420

gtgcacctgc agcgcggcgt gcggggtcct gggcggcggg cgcgggcagt gctgctggcg     480

ctcatctggg gctattcggc ggtcgccgct ctgcctctct gcgtcttctt tcgagtcgtc     540

ccgcaacggc tccccggcgc cgaccaggaa atttcgattt gcacactgat ttggcccacc     600

attcctggag agatctcgtg ggatgtctct tttgttactt tgaacttctt ggtgccagga     660

ctggtcattg tgatcagtta ctccaaaatt ttacagatca caaaggcatc aaggaagagg     720

ctcacggtaa gcctggccta ctcggagagc caccagatcc gcgtgtccca gcaggacttc     780

cggctcttcc gcaccctctt cctcctcatg gtctccttct tcatcatgtg gagccccatc     840

atcatcacca tcctcctcat cctgatccag aacttcaagc aagacctggt catctggccg     900

tccctcttct tctgggtggt ggccttcaca tttgctaatt cagccctaaa ccccatcctc     960

tacaacatga cactgtgcag gaatgagtgg aagaaaattt tttgctgctt ctggttccca    1020

gaaaagggag ccattttaac agacacatct gtcaaaagaa atgacttgtc gattatttct    1080

ggctaa                                                               1086
```

```
<210> SEQ ID NO 12
<211> LENGTH: 361
<212> TYPE: PRT
<213> ORGANISM: Unknown
<220> FEATURE:
<223> OTHER INFORMATION: Novel Sequence

<400> SEQUENCE: 12

Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
                85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Glu Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
                165                 170                 175

Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
        195                 200                 205

Val Ser Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240

Leu Thr Val Ser Leu Ala Tyr Ser Glu Ser His Gln Ile Arg Val Ser
                245                 250                 255

Gln Gln Asp Phe Arg Leu Phe Arg Thr Leu Phe Leu Leu Met Val Ser
            260                 265                 270

Phe Phe Ile Met Trp Ser Pro Ile Ile Ile Thr Ile Leu Leu Ile Leu
        275                 280                 285

Ile Gln Asn Phe Lys Gln Asp Leu Val Ile Trp Pro Ser Leu Phe Phe
    290                 295                 300

Trp Val Val Ala Phe Thr Phe Ala Asn Ser Ala Leu Asn Pro Ile Leu
305                 310                 315                 320

Tyr Asn Met Thr Leu Cys Arg Asn Glu Trp Lys Lys Ile Phe Cys Cys
                325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
        355                 360
```

-continued

<210> SEQ ID NO 13
<211> LENGTH: 1212
<212> TYPE: DNA
<213> ORGANISM: Homo sapiens

<400> SEQUENCE: 13

```
atggcttgca atggcagtgc ggccaggggg cactttgacc ctgaggactt gaacctgact      60

gacgaggcac tgagactcaa gtacctgggg ccccagcaga cagagctgtt catgcccatc     120

tgtgccacat acctgctgat cttcgtggtg ggcgctgtgg gcaatgggct gacctgtctg     180

gtcatcctgc gccacaaggc catgcgcacg cctaccaact actacctctt cagcctggcc     240

gtgtcggacc tgctggtgct gctggtgggc ctgcccctgg agctctatga gatgtggcac     300

aactacccct tcctgctggg cgttggtggc tgctatttcc gcacgctact gtttgagatg     360

gtctgcctgg cctcagtgct caacgtcact gccctgagcg tggaacgcta tgtggccgtg     420

gtgcacccac tccaggccag gtccatggtg acgcgggccc atgtgcgccg agtgcttggg     480

gccgtctggg gtcttgccat gctctgctcc ctgcccaaca ccagcctgca cggcatccgg     540

cagctgcacg tgccctgccg gggcccagtg ccagactcag ctgtttgcat gctggtccgc     600

ccacgggccc tctacaacat ggtagtgcag accaccgcgc tgctcttctt ctgcctgccc     660

atggccatca tgagcgtgct ctacctgctc attgggctgc gactgcggcg ggagaggctg     720

ctgctcatgc aggaggccaa gggcaggggc tctgcagcag ccaggtccag atacacctgc     780

aggctccagc agcacgatcg ggccggagaa caagtgacca agatgctgtt tgtcctggtc     840

gtggtgtttg gcatctgctg ggccccgttc cacgccgacc gcgtcatgtg gagcgtcgtg     900

tcacagtgga cagatggcct gcacctggcc ttccagcacg tgcacgtcat ctccggcatc     960

ttcttctacc tgggctcggc ggccaacccc gtgctctata gcctcatgtc cagccgcttc    1020

cgagagacct tccaggaggc cctgtgcctc ggggcctgct gccatcgcct cagaccccgc    1080

cacagctccc acagcctcag caggatgacc acaggcagca ccctgtgtga tgtgggctcc    1140

ctgggcagct gggtccaccc cctggctggg aacgatggcc cagaggcgca gcaagagacc    1200

gatccatcct ga                                                        1212
```

<210> SEQ ID NO 14
<211> LENGTH: 403
<212> TYPE: PRT
<213> ORGANISM: Homo sapiens

<400> SEQUENCE: 14

```
Met Ala Cys Asn Gly Ser Ala Ala Arg Gly His Phe Asp Pro Glu Asp
1               5                   10                  15

Leu Asn Leu Thr Asp Glu Ala Leu Arg Leu Lys Tyr Leu Gly Pro Gln
            20                  25                  30

Gln Thr Glu Leu Phe Met Pro Ile Cys Ala Thr Tyr Leu Leu Ile Phe
        35                  40                  45

Val Val Gly Ala Val Gly Asn Gly Leu Thr Cys Leu Val Ile Leu Arg
    50                  55                  60

His Lys Ala Met Arg Thr Pro Thr Asn Tyr Tyr Leu Phe Ser Leu Ala
65                  70                  75                  80

Val Ser Asp Leu Leu Val Leu Leu Val Gly Leu Pro Leu Glu Leu Tyr
                85                  90                  95

Glu Met Trp His Asn Tyr Pro Phe Leu Leu Gly Val Gly Gly Cys Tyr
            100                 105                 110
```

-continued

```
Phe Arg Thr Leu Leu Phe Glu Met Val Cys Leu Ala Ser Val Leu Asn
        115                 120                 125

Val Thr Ala Leu Ser Val Glu Arg Tyr Val Ala Val Val His Pro Leu
    130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Ala Arg Ser
                245                 250                 255

Arg Tyr Thr Cys Arg Leu Gln Gln His Asp Arg Gly Arg Arg Gln Val
            260                 265                 270

Thr Lys Met Leu Phe Val Leu Val Val Val Phe Gly Ile Cys Trp Ala
        275                 280                 285

Pro Phe His Ala Asp Arg Val Met Trp Ser Val Val Ser Gln Trp Thr
    290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335

Ser Ser Arg Phe Arg Glu Thr Phe Gln Glu Ala Leu Cys Leu Gly Ala
            340                 345                 350

Cys Cys His Arg Leu Arg Pro Arg His Ser Ser His Ser Leu Ser Arg
        355                 360                 365

Met Thr Thr Gly Ser Thr Leu Cys Asp Val Gly Ser Leu Gly Ser Trp
    370                 375                 380

Val His Pro Leu Ala Gly Asn Asp Gly Pro Glu Ala Gln Gln Glu Thr
385                 390                 395                 400

Asp Pro Ser


<210> SEQ ID NO 15
<211> LENGTH: 930
<212> TYPE: DNA
<213> ORGANISM: Homo sapiens

<400> SEQUENCE: 15

atgaatggca cctacaacac ctgtggctcc agcgacctca cctggccccc agcgatcaag      60

ctgggcttct acgcctactt gggcgtcctg ctggtgctag gcctgctgct caacagcctg     120

gcgctctggg tgttctgctg ccgcatgcag cagtggacgg agacccgcat ctacatgacc     180

aacctggcgg tggccgacct ctgcctgctg tgcaccttgc ccttcgtgct gcactccctg     240

cgagacacct cagacacgcc gctgtgccag ctctcccagg gcatctacct gaccaacagg     300

tacatgagca tcagcctggt cacggccatc gccgtggacc gctatgtggc cgtgcggcac     360

ccgctgcgtg cccgcgggct gcggtccccc aggcaggctg cggccgtgtg cgcggtcctc     420

tgggtgctgg tcatcggctc cctggtggct cgctggctcc tggggattca ggagggcggc     480
```

```
ttctgcttca ggagcacccg gcacaatttc aactccatgc ggttcccgct gctgggattc    540

tacctgcccc tggccgtggt ggtcttctgc tccctgaagg tggtgactgc cctggcccag    600

aggccaccca ccgacgtggg gcaggcagag gccacccgca aggctgcccg catggtctgg    660

gccaacctcc tggtgttcgt ggtctgcttc ctgcccctgc acgtggggct gacagtgcgc    720

ctcgcagtgg gctggaacgc ctgtgccctc ctggagacga tccgtcgcgc cctgtacata    780

accagcaagc tctcagatgc caactgctgc ctggacgcca tctgctacta ctacatggcc    840

aaggagttcc aggaggcgtc tgcactggcc gtggctcccc gtgctaaggc ccacaaaagc    900

caggactctc tgtgcgtgac cctcgcctaa                                     930
```

```
<210> SEQ ID NO 16
<211> LENGTH: 309
<212> TYPE: PRT
<213> ORGANISM: Homo sapiens

<400> SEQUENCE: 16

Met Asn Gly Thr Tyr Asn Thr Cys Gly Ser Ser Asp Leu Thr Trp Pro
1               5                   10                  15

Pro Ala Ile Lys Leu Gly Phe Tyr Ala Tyr Leu Gly Val Leu Leu Val
            20                  25                  30

Leu Gly Leu Leu Leu Asn Ser Leu Ala Leu Trp Val Phe Cys Cys Arg
        35                  40                  45

Met Gln Gln Trp Thr Glu Thr Arg Ile Tyr Met Thr Asn Leu Ala Val
    50                  55                  60

Ala Asp Leu Cys Leu Leu Cys Thr Leu Pro Phe Val Leu His Ser Leu
65                  70                  75                  80

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Arg Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
        275                 280                 285
```

-continued

```
Leu Ala Val Ala Pro Arg Ala Lys Ala His Lys Ser Gln Asp Ser Leu
    290                 295                 300

Cys Val Thr Leu Ala
305
```

<210> SEQ ID NO 17
<211> LENGTH: 1446
<212> TYPE: DNA
<213> ORGANISM: Homo sapiens

<400> SEQUENCE: 17

```
atgcggtggc tgtggcccct ggctgtctct cttgctgtga ttttggctgt ggggctaagc     60

agggtctctg gggtgcccc cctgcacctg ggcaggcaca gagccgagac ccaggagcag    120

cagagccgat ccaagagggg caccgaggat gaggaggcca agggcgtgca gcagtatgtg    180

cctgaggagt gggcggagta cccccggccc attcaccctg ctggcctgca gccaaccaag    240

cccttggtgg ccaccagccc taaccccgac aaggatgggg gcaccccaga cagtgggcag    300

gaactgaggg gcaatctgac aggggcacca gggcagaggc tacagatcca gaaccccctg    360

tatccggtga ccgagagctc ctacagtgcc tatgccatca tgcttctggc gctggtggtg    420

tttgcggtgg gcattgtggg caacctgtcg gtcatgtgca tcgtgtggca cagctactac    480

ctgaagagcg cctggaactc catccttgcc agcctggccc tctgggattt tctggtcctc    540

tttttctgcc tccctattgt catcttcaac gagatcacca agcagaggct actgggtgac    600

gtttcttgtc gtgccgtgcc cttcatggag gtctcctctc tgggagtcac gactttcagc    660

ctctgtgccc tgggcattga ccgcttccac gtggccacca gcaccctgcc caaggtgagg    720

cccatcgagc ggtgccaatc catcctggcc aagttggctg tcatctgggt gggctccatg    780

acgctggctg tgcctgagct cctgctgtgg cagctggcac aggagcctgc ccccaccatg    840

ggcaccctgg actcatgcat catgaaaccc tcagccagcc tgcccgagtc cctgtattca    900

ctggtgatga cctaccagaa cgcccgcatg tggtggtact ttggctgcta cttctgcctg    960

cccatcctct tcacagtcac ctgccagctg gtgacatggc gggtgcgagg ccctccaggg   1020

aggaagtcag agtgcagggc cagcaagcac gagcagtgtg agagccagct caacagcacc   1080

gtggtgggcc tgaccgtggt ctacgccttc tgcaccctcc cagagaacgt ctgcaacatc   1140

gtggtggcct acctctccac cgagctgacc cgccagaccc tggacctcct gggcctcatc   1200

aaccagttct ccaccttctt caagggcgcc atcaccccag tgctgctcct ttgcatctgc   1260

aggccgctgg gccaggcctt cctggactgc tgctgctgct gctgctgtga ggagtgcggc   1320

ggggcttcgg aggcctctgc tgccaatggg tcggacaaca agctcaagac cgaggtgtcc   1380

tcttccatct acttccacaa gcccagggag tcacccccac tcctgcccct gggcacacct   1440

tgctga                                                              1446
```

<210> SEQ ID NO 18
<211> LENGTH: 481
<212> TYPE: PRT
<213> ORGANISM: Homo sapiens

<400> SEQUENCE: 18

```
Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
```

-continued

```
        35                  40                  45

Glu Asp Glu Glu Ala Lys Gly Val Gln Gln Tyr Val Pro Glu Glu Trp
    50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Asp Lys Asp Gly Gly Thr Pro
                85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
        115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
                165                 170                 175

Phe Leu Val Leu Phe Phe Cys Leu Pro Ile Val Ile Phe Asn Glu Ile
            180                 185                 190

Thr Lys Gln Arg Leu Leu Gly Asp Val Ser Cys Arg Ala Val Pro Phe
        195                 200                 205

Met Glu Val Ser Ser Leu Gly Val Thr Thr Phe Ser Leu Cys Ala Leu
    210                 215                 220

Gly Ile Asp Arg Phe His Val Ala Thr Ser Thr Leu Pro Lys Val Arg
225                 230                 235                 240

Pro Ile Glu Arg Cys Gln Ser Ile Leu Ala Lys Leu Ala Val Ile Trp
                245                 250                 255

Val Gly Ser Met Thr Leu Ala Val Pro Glu Leu Leu Leu Trp Gln Leu
            260                 265                 270

Ala Gln Glu Pro Ala Pro Thr Met Gly Thr Leu Asp Ser Cys Ile Met
        275                 280                 285

Lys Pro Ser Ala Ser Leu Pro Glu Ser Leu Tyr Ser Leu Val Met Thr
    290                 295                 300

Tyr Gln Asn Ala Arg Met Trp Trp Tyr Phe Gly Cys Tyr Phe Cys Leu
305                 310                 315                 320

Pro Ile Leu Phe Thr Val Thr Cys Gln Leu Val Thr Trp Arg Val Arg
                325                 330                 335

Gly Pro Pro Gly Arg Lys Ser Glu Cys Arg Ala Ser Lys His Glu Gln
            340                 345                 350

Cys Glu Ser Gln Leu Asn Ser Thr Val Val Gly Leu Thr Val Val Tyr
        355                 360                 365

Ala Phe Cys Thr Leu Pro Glu Asn Val Cys Asn Ile Val Val Ala Tyr
    370                 375                 380

Leu Ser Thr Glu Leu Thr Arg Gln Thr Leu Asp Leu Leu Gly Leu Ile
385                 390                 395                 400

Asn Gln Phe Ser Thr Phe Phe Lys Gly Ala Ile Thr Pro Val Leu Leu
                405                 410                 415

Leu Cys Ile Cys Arg Pro Leu Gly Gln Ala Phe Leu Asp Cys Cys Cys
            420                 425                 430

Cys Cys Cys Cys Glu Glu Cys Gly Gly Ala Ser Glu Ala Ser Ala Ala
        435                 440                 445

Asn Gly Ser Asp Asn Lys Leu Lys Thr Glu Val Ser Ser Ser Ile Tyr
    450                 455                 460
```

-continued

```
Phe His Lys Pro Arg Glu Ser Pro Pro Leu Leu Pro Leu Gly Thr Pro
465                 470                 475                 480

Cys


<210> SEQ ID NO 19
<211> LENGTH: 29
<212> TYPE: DNA
<213> ORGANISM: Unknown
<220> FEATURE:
<223> OTHER INFORMATION: Novel Sequence

<400> SEQUENCE: 19

aaagattcag gtgtgggaag atggaaacc                                     29


<210> SEQ ID NO 20
<211> LENGTH: 29
<212> TYPE: DNA
<213> ORGANISM: Unknown
<220> FEATURE:
<223> OTHER INFORMATION: Novel Sequence

<400> SEQUENCE: 20

aaaggatccc cgacctcaca ttgcttgta                                     29


<210> SEQ ID NO 21
<211> LENGTH: 30
<212> TYPE: DNA
<213> ORGANISM: Unknown
<220> FEATURE:
<223> OTHER INFORMATION: Novel Sequence

<400> SEQUENCE: 21

caggaattca tcagaacaga caccatggca                                    30


<210> SEQ ID NO 22
<211> LENGTH: 31
<212> TYPE: DNA
<213> ORGANISM: Unknown
<220> FEATURE:
<223> OTHER INFORMATION: Novel Sequence

<400> SEQUENCE: 22

gcaggatcca gagcagtttt ttcgaaaccc t                                  31


<210> SEQ ID NO 23
<211> LENGTH: 33
<212> TYPE: DNA
<213> ORGANISM: Unknown
<220> FEATURE:
<223> OTHER INFORMATION: Novel Sequence

<400> SEQUENCE: 23

tccaagcttc aagggtctct ccacgatggc ctg                                33


<210> SEQ ID NO 24
<211> LENGTH: 33
<212> TYPE: DNA
<213> ORGANISM: Unknown
<220> FEATURE:
<223> OTHER INFORMATION: Novel Sequence

<400> SEQUENCE: 24

tgcgaattct ctgtggcccc ctgacccct aaa                                 33
```

-continued

<210> SEQ ID NO 25
<211> LENGTH: 36
<212> TYPE: DNA
<213> ORGANISM: Unknown
<220> FEATURE:
<223> OTHER INFORMATION: Novel Sequence

<400> SEQUENCE: 25
ggtaagctta ccatggcctg caacagcacg tccctt 36

<210> SEQ ID NO 26
<211> LENGTH: 33
<212> TYPE: DNA
<213> ORGANISM: Unknown
<220> FEATURE:
<223> OTHER INFORMATION: Novel Sequence

<400> SEQUENCE: 26
gacgaattca accgcagact ggttttcatt gca 33

<210> SEQ ID NO 27
<211> LENGTH: 33
<212> TYPE: DNA
<213> ORGANISM: Unknown
<220> FEATURE:
<223> OTHER INFORMATION: Novel Sequence

<400> SEQUENCE: 27
gcaagcttgt gccctcacca agccatgcga gcc 33

<210> SEQ ID NO 28
<211> LENGTH: 30
<212> TYPE: DNA
<213> ORGANISM: Unknown
<220> FEATURE:
<223> OTHER INFORMATION: Novel Sequence

<400> SEQUENCE: 28
cggaattcag caatgagttc cgacagaagc 30

<210> SEQ ID NO 29
<211> LENGTH: 37
<212> TYPE: DNA
<213> ORGANISM: Unknown
<220> FEATURE:
<223> OTHER INFORMATION: Novel Sequence

<400> SEQUENCE: 29
accatggctt gcaatggcag tgcggccagg gggcact 37

<210> SEQ ID NO 30
<211> LENGTH: 39
<212> TYPE: DNA
<213> ORGANISM: Unknown
<220> FEATURE:
<223> OTHER INFORMATION: Novel Sequence

<400> SEQUENCE: 30
cgaccaggac aaacagcatc ttggtcactt gtctccggc 39

<210> SEQ ID NO 31
<211> LENGTH: 39
<212> TYPE: DNA
<213> ORGANISM: Unknown
<220> FEATURE:
<223> OTHER INFORMATION: Novel Sequence

<400> SEQUENCE: 31
gaccaagatg ctgtttgtcc tggtcgtggt gtttggcat 39

<210> SEQ ID NO 32
<211> LENGTH: 35
<212> TYPE: DNA
<213> ORGANISM: Unknown
<220> FEATURE:
<223> OTHER INFORMATION: Novel Sequence

<400> SEQUENCE: 32
cggaattcag gatggatcgg tctcttgctg cgcct 35

<210> SEQ ID NO 33
<211> LENGTH: 30
<212> TYPE: DNA
<213> ORGANISM: Unknown
<220> FEATURE:
<223> OTHER INFORMATION: Novel Sequence

<400> SEQUENCE: 33
gcgaattccg gctccctgtg ctgccccagg 30

<210> SEQ ID NO 34
<211> LENGTH: 30
<212> TYPE: DNA
<213> ORGANISM: Unknown
<220> FEATURE:
<223> OTHER INFORMATION: Novel Sequence

<400> SEQUENCE: 34
gcggatcccg gagcccccga gacctggccc 30

<210> SEQ ID NO 35
<211> LENGTH: 31
<212> TYPE: DNA
<213> ORGANISM: Unknown
<220> FEATURE:
<223> OTHER INFORMATION: Novel Sequence

<400> SEQUENCE: 35
ctggaattct cctgctcatc cagccatgcg g 31

<210> SEQ ID NO 36
<211> LENGTH: 30
<212> TYPE: DNA
<213> ORGANISM: Unknown
<220> FEATURE:
<223> OTHER INFORMATION: Novel Sequence

<400> SEQUENCE: 36
cctggatccc cacccctact ggggcctcag 30

<210> SEQ ID NO 37
<211> LENGTH: 29
<212> TYPE: DNA
<213> ORGANISM: Unknown
<220> FEATURE:
<223> OTHER INFORMATION: Novel Sequence

<400> SEQUENCE: 37
tccagccgtc ccaaacgtgt cttcgctgc 29

<210> SEQ ID NO 38
<211> LENGTH: 31

-continued

<212> TYPE: DNA
<213> ORGANISM: Unknown
<220> FEATURE:
<223> OTHER INFORMATION: Novel Sequence

<400> SEQUENCE: 38
ctccttcggt cctcctatcg ttgtcagaag t 31

<210> SEQ ID NO 39
<211> LENGTH: 33
<212> TYPE: DNA
<213> ORGANISM: Unknown
<220> FEATURE:
<223> OTHER INFORMATION: Novel Sequence

<400> SEQUENCE: 39
cagaagcaca gatcaaaaaa gatcatcttc ctg 33

<210> SEQ ID NO 40
<211> LENGTH: 31
<212> TYPE: DNA
<213> ORGANISM: Unknown
<220> FEATURE:
<223> OTHER INFORMATION: Novel Sequence

<400> SEQUENCE: 40
acaggaatca cagccgaggg ggagtgccac t 31

<210> SEQ ID NO 41
<211> LENGTH: 32
<212> TYPE: DNA
<213> ORGANISM: Unknown
<220> FEATURE:
<223> OTHER INFORMATION: Novel Sequence

<400> SEQUENCE: 41
tgtgttcttt ccggcatgtt ttcttgggct tg 32

<210> SEQ ID NO 42
<211> LENGTH: 32
<212> TYPE: DNA
<213> ORGANISM: Unknown
<220> FEATURE:
<223> OTHER INFORMATION: Novel Sequence

<400> SEQUENCE: 42
caagcccaag aaaacatgcc ggaaagaaca ca 32

<210> SEQ ID NO 43
<211> LENGTH: 33
<212> TYPE: DNA
<213> ORGANISM: Unknown
<220> FEATURE:
<223> OTHER INFORMATION: Novel Sequence

<400> SEQUENCE: 43
ctcatggtca catgttgtgt gtatgccatc aag 33

<210> SEQ ID NO 44
<211> LENGTH: 33
<212> TYPE: DNA
<213> ORGANISM: Unknown
<220> FEATURE:
<223> OTHER INFORMATION: Novel Sequence

<400> SEQUENCE: 44

-continued cttgatggca tacacacaac atgtgaccat gag 33

<210> SEQ ID NO 45
<211> LENGTH: 34
<212> TYPE: DNA
<213> ORGANISM: Unknown
<220> FEATURE:
<223> OTHER INFORMATION: Novel Sequence

<400> SEQUENCE: 45
acgaagccaa gcccaaggga ttcactatgt acac 34

<210> SEQ ID NO 46
<211> LENGTH: 34
<212> TYPE: DNA
<213> ORGANISM: Unknown
<220> FEATURE:
<223> OTHER INFORMATION: Novel Sequence

<400> SEQUENCE: 46
gtgtacatag tgaatccctt gggcttggct ccgt 34

<210> SEQ ID NO 47
<211> LENGTH: 35
<212> TYPE: DNA
<213> ORGANISM: Unknown
<220> FEATURE:
<223> OTHER INFORMATION: Novel Sequence

<400> SEQUENCE: 47
gtcaccacct ttcacccgat gtgctctgtg catag 35

<210> SEQ ID NO 48
<211> LENGTH: 35
<212> TYPE: DNA
<213> ORGANISM: Unknown
<220> FEATURE:
<223> OTHER INFORMATION: Novel Sequence

<400> SEQUENCE: 48
ctatgcacag agcacatcgg gtgaaaggtg gtgac 35

<210> SEQ ID NO 49
<211> LENGTH: 36
<212> TYPE: DNA
<213> ORGANISM: Unknown
<220> FEATURE:
<223> OTHER INFORMATION: Novel Sequence

<400> SEQUENCE: 49
ccttttgttc tttaagtcct atgtcacccc agtcct 36

<210> SEQ ID NO 50
<211> LENGTH: 36
<212> TYPE: DNA
<213> ORGANISM: Unknown
<220> FEATURE:
<223> OTHER INFORMATION: Novel Sequence

<400> SEQUENCE: 50
aggactgggg tgacatagga cttaaagaac aaaagg 36

<210> SEQ ID NO 51
<211> LENGTH: 31
<212> TYPE: DNA
<213> ORGANISM: Unknown

<220> FEATURE:
<223> OTHER INFORMATION: Novel Sequence

<400> SEQUENCE: 51
atgtggagcc ccatcttcat caccatcctc c 31

<210> SEQ ID NO 52
<211> LENGTH: 31
<212> TYPE: DNA
<213> ORGANISM: Unknown
<220> FEATURE:
<223> OTHER INFORMATION: Novel Sequence

<400> SEQUENCE: 52
ggaggatggt gatgaagatg gggctccaca t 31

<210> SEQ ID NO 53
<211> LENGTH: 33
<212> TYPE: DNA
<213> ORGANISM: Unknown
<220> FEATURE:
<223> OTHER INFORMATION: Novel Sequence

<400> SEQUENCE: 53
gccgcggtca gcctgaatcg catggtgtgc atc 33

<210> SEQ ID NO 54
<211> LENGTH: 33
<212> TYPE: DNA
<213> ORGANISM: Unknown
<220> FEATURE:
<223> OTHER INFORMATION: Novel Sequence

<400> SEQUENCE: 54
gatgcacacc atgcgattca ggctgaccgc ggc 33

<210> SEQ ID NO 55
<211> LENGTH: 29
<212> TYPE: DNA
<213> ORGANISM: Unknown
<220> FEATURE:
<223> OTHER INFORMATION: Novel Sequence

<400> SEQUENCE: 55
ggccggagac aagtgaaaag atgctgttt 29

<210> SEQ ID NO 56
<211> LENGTH: 30
<212> TYPE: DNA
<213> ORGANISM: Unknown
<220> FEATURE:
<223> OTHER INFORMATION: Novel Sequence

<400> SEQUENCE: 56
aaacagcatc ttttcactt gtctccggcc 30

<210> SEQ ID NO 57
<211> LENGTH: 27
<212> TYPE: DNA
<213> ORGANISM: Unknown
<220> FEATURE:
<223> OTHER INFORMATION: Novel Sequence

<400> SEQUENCE: 57
gagagccagc tcaagagcac cgtggtg 27

<210> SEQ ID NO 58
<211> LENGTH: 31
<212> TYPE: DNA
<213> ORGANISM: Unknown
<220> FEATURE:
<223> OTHER INFORMATION: Novel Sequence

<400> SEQUENCE: 58
ctccttcggt cctcctatcg ttgtcagaag t 31

<210> SEQ ID NO 59
<211> LENGTH: 31
<212> TYPE: DNA
<213> ORGANISM: Unknown
<220> FEATURE:
<223> OTHER INFORMATION: Novel Sequence

<400> SEQUENCE: 59
agtggcactc cccctcggct gtgattcctg t 31

<210> SEQ ID NO 60
<211> LENGTH: 30
<212> TYPE: DNA
<213> ORGANISM: Unknown
<220> FEATURE:
<223> OTHER INFORMATION: Novel Sequence

<400> SEQUENCE: 60
gccacccgca aggctaaacg catggtctgg 30

<210> SEQ ID NO 61
<211> LENGTH: 31
<212> TYPE: DNA
<213> ORGANISM: Unknown
<220> FEATURE:
<223> OTHER INFORMATION: Novel Sequence

<400> SEQUENCE: 61
ctccttcggt cctcctatcg ttgtcagaag t 31

<210> SEQ ID NO 62
<211> LENGTH: 1062
<212> TYPE: DNA
<213> ORGANISM: Unknown
<220> FEATURE:
<223> OTHER INFORMATION: Novel Sequence

<400> SEQUENCE: 62
atggaaacca acttctccat tcctctgaat gaaactgagg aggtgctccc tgagcctgct 60
ggccacaccg ttctgtggat cttctcattg ctagtccacg gagtcacctt tgtcttcggg 120
gtcctgggca atgggcttgt gatctgggtg gctggattcc ggatgacacg cacagtcaac 180
accatctgtt acctgaacct ggccctagct gacttctctt tcagtgccat cctaccattc 240
cgaatggtct cagtcgccat gagagaaaaa tggccttttg gctcattcct atgtaagtta 300
gttcatgtta tgatagacat caacctgttt gtcagtgtct acctgatcac catcattgct 360
ctggaccgct gtatttgtgt cctgcatcca gcctgggccc agaaccatcg caccatgagt 420
ctggccaaga gggtgatgac gggactctgg attttcacca tagtccttac cttaccaaat 480
ttcatcttct ggactacaat aagtactacg aatggggaca catactgtat tttcaacttt 540
gcattctggg gtgacactgc tgtagagagg ttgaacgtgt tcattaccat ggccaaggtc 600
tttctgatcc tccacttcat tattggcttc agcgtgccta tgtccatcat cacagtctgc 660

-continued

```
tatgggatca tcgctgccaa aattcacaga aaccacatga ttaaatccag ccgtcccaaa    720

cgtgtcttcg ctgctgtggt ggcttctttc ttcatctgtt ggttccctta tgaactaatt    780

ggcattctaa tggcagtctg gctcaaagag atgttgttaa atggcaaata caaaatcatt    840

cttgtcctga ttaacccaac aagctccttg gccttttttta acagctgcct caacccaatt    900

ctctacgtct ttatgggtcg taacttccaa gaaagactga ttcgctcttt gcccactagt    960

ttggagaggg ccctgactga ggtccctgac tcagcccaga ccagcaacac agacaccact   1020

tctgcttcac ctcctgagga gacggagtta caagcaatgt ga                      1062
```

<210> SEQ ID NO 63
<211> LENGTH: 353
<212> TYPE: PRT
<213> ORGANISM: Unknown
<220> FEATURE:
<223> OTHER INFORMATION: Novel Sequence

<400> SEQUENCE: 63

```
Met Glu Thr Asn Phe Ser Ile Pro Leu Asn Glu Thr Glu Glu Val Leu
1               5                   10                  15

Pro Glu Pro Ala Gly His Thr Val Leu Trp Ile Phe Ser Leu Leu Val
            20                  25                  30

His Gly Val Thr Phe Val Phe Gly Val Leu Gly Asn Gly Leu Val Ile
        35                  40                  45

Trp Val Ala Gly Phe Arg Met Thr Arg Thr Val Asn Thr Ile Cys Tyr
    50                  55                  60

Leu Asn Leu Ala Leu Ala Asp Phe Ser Phe Ser Ala Ile Leu Pro Phe
65                  70                  75                  80

Arg Met Val Ser Val Ala Met Arg Glu Lys Trp Pro Phe Gly Ser Phe
                85                  90                  95

Leu Cys Lys Leu Val His Val Met Ile Asp Ile Asn Leu Phe Val Ser
            100                 105                 110

Val Tyr Leu Ile Thr Ile Ile Ala Leu Asp Arg Cys Ile Cys Val Leu
        115                 120                 125

His Pro Ala Trp Ala Gln Asn His Arg Thr Met Ser Leu Ala Lys Arg
    130                 135                 140

Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
            180                 185                 190

Val Phe Ile Thr Met Ala Lys Val Phe Leu Ile Leu His Phe Ile Ile
        195                 200                 205

Gly Phe Ser Val Pro Met Ser Ile Ile Thr Val Cys Tyr Gly Ile Ile
    210                 215                 220

Ala Ala Lys Ile His Arg Asn His Met Ile Lys Ser Ser Arg Pro Lys
225                 230                 235                 240

Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
            260                 265                 270

Leu Asn Gly Lys Tyr Lys Ile Ile Leu Val Leu Ile Asn Pro Thr Ser
        275                 280                 285
```

-continued

```
Ser Leu Ala Phe Phe Asn Ser Cys Leu Asn Pro Ile Leu Tyr Val Phe
    290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr Asp Thr Thr Ser Ala Ser Pro Pro Glu Glu Thr Glu Leu Gln Ala
            340                 345                 350

Met
```

<210> SEQ ID NO 64
<211> LENGTH: 1029
<212> TYPE: DNA
<213> ORGANISM: Unknown
<220> FEATURE:
<223> OTHER INFORMATION: Novel Sequence

<400> SEQUENCE: 64

```
atggcagagc atgattacca tgaagactat gggttcagca gtttcaatga cagcagccag     60

gaggagcatc aagccttcct gcagttcagc aaggtctttc tgccctgcat gtacctggtg    120

gtgtttgtct gtggtctggt ggggaactct ctggtgctgg tcatatccat cttctaccat    180

aagttgcaga gcctgacgga tgtgttcctg gtgaacctac ccctggctga cctggtgttt    240

gtctgcactc tgcccttctg ggcctatgca ggcatccatg aatgggtgtt tggccaggtc    300

atgtgcaaaa gcctactggg catctacact attaacttct acacgtccat gctcatcctc    360

acctgcatca ctgtggatcg tttcattgta gtggttaagg ccaccaaggc ctacaaccag    420

caagccaaga ggatgacctg gggcaaggtc accagcttgc tcatctgggt gatatccctg    480

ctggtttcct tgccccaaat tatctatggc aatgtcttta atctcgacaa gctcatatgt    540

ggttaccatg acgaggcaat ttccactgtg gttcttgcca cccagatgac actggggttc    600

ttcttgccac tgctcaccat gattgtctgc tattcagtca taatcaaaac actgcttcat    660

gctggaggct tccagaagca cagatcaaaa aagatcatct tcctggtgat ggctgtgttc    720

ctgctgaccc agatgccctt caacctcatg aagttcatcc gcagcacaca ctgggaatac    780

tatgccatga ccagctttca ctacaccatc atggtgacag aggccatcgc atacctgagg    840

gcctgcctta accctgtgct ctatgccttt gtcagcctga agtttcgaaa gaacttctgg    900

aaacttgtga aggacattgg ttgcctccct taccttgggg tctcacatca atggaaatct    960

tctgaggaca attccaagac tttttctgcc tcccacaatg tggaggccac cagcatgttc   1020

cagttatag                                                            1029
```

<210> SEQ ID NO 65
<211> LENGTH: 342
<212> TYPE: PRT
<213> ORGANISM: Unknown
<220> FEATURE:
<223> OTHER INFORMATION: Novel Sequence

<400> SEQUENCE: 65

```
Met Ala Glu His Asp Tyr His Glu Asp Tyr Gly Phe Ser Ser Phe Asn
1               5                   10                  15

Asp Ser Ser Gln Glu Glu His Gln Ala Phe Leu Gln Phe Ser Lys Val
            20                  25                  30

Phe Leu Pro Cys Met Tyr Leu Val Val Phe Val Cys Gly Leu Val Gly
        35                  40                  45
```

-continued

```
Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125

Ile Val Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Lys Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340
```

<210> SEQ ID NO 66
<211> LENGTH: 2748
<212> TYPE: DNA
<213> ORGANISM: Unknown
<220> FEATURE:
<223> OTHER INFORMATION: Novel Sequence

<400> SEQUENCE: 66

```
atggtccagc tgaggaagct gctccgcgtc ctgactttga tgaagttccc ctgctgcgtg      60

ctggaggtgc tcctgtgcgc gctggcggcg gcggcgcgcg gccaggagat gtacgccccg     120

cactcaatcc ggatcgaggg ggacgtcacc ctcgggggc tgttccccgt gcacgccaag     180

ggtcccagcg gagtgccctg cggcgacatc aagagggaaa acgggatcca caggctggaa     240

gcgatgctct acgccctgga ccagatcaac agtgatccca acctactgcc caacgtgacg     300

ctgggcgcgc ggatcctgga cacttgttcc agggacactt acgcgctcga acagtcgctt     360
```

-continued

```
actttcgtcc aggcgctcat ccagaaggac acctccgacg tgcgctgcac caacggcgaa    420
ccgccggttt tcgtcaagcc ggagaaagta gttggagtga ttggggcttc ggggagttcg    480
gtctccatca tggtagccaa catcctgagg ctcttccaga tcccccagat tagttatgca    540
tcaacggcac ccgagctaag tgatgaccgg cgctatgact tcttctctcg cgtggtgcca    600
cccgattcct tccaagccca ggccatggta gacattgtaa aggccctagg ctggaattat    660
gtgtctaccc tcgcatcgga aggaagttat ggagagaaag gtgtggagtc cttcacgcag    720
atttccaaag aggcaggtgg actctgcatt gcccagtccg tgagaatccc ccaggaacgc    780
aaagacagga ccattgactt tgatagaatt atcaaacagc tcctggacac ccccaactcc    840
agggccgtcg tgatttttgc caacgatgag gatataaagc agatccttgc agcagccaaa    900
agagctgacc aagttggcca ttttctttgg gtgggatcag acagctgggg atccaaaata    960
aacccactgc accagcatga agatatcgca gaaggggcca tcaccattca gcccaagcga   1020
gccacggtgg aagggtttga tgcctacttt acgtcccgta cacttgaaaa caacagaaga   1080
aatgtatggt ttgccgaata ctgggaggaa aacttcaact gcaagttgac gattagtggg   1140
tcaaaaaaag aagacacaga tcgcaaatgc acaggacagg agagaattgg aaaagattcc   1200
aactatgagc aggagggtaa agtccagttc gtgattgacg cagtctatgc tatggctcac   1260
gcccttcacc acatgaacaa ggatctctgt gctgactacc ggggtgtctg cccagagatg   1320
gagcaagctg gaggcaagaa gttgctgaag tatatacgca atgttaattt caatggtagt   1380
gctggcactc cagtgatgtt taacaagaac ggggatgcac ctgggcgtta tgacatcttt   1440
cagtaccaga ccacaaacac cagcaacccg ggttaccgtc tgatcgggca gtggacagac   1500
gaacttcagc tcaatataga agacatgcag tggggtaaag gagtccgaga gatacccgcc   1560
tcagtgtgca cactaccatg taagccagga cagagaaaga agacacagaa aggaactcct   1620
tgctgttgga cctgtgagcc ttgcgatggt taccagtacc agtttgatga gatgacatgc   1680
cagcattgcc cctatgacca gaggcccaat gaaaatcgaa ccggatgcca ggatattccc   1740
atcatcaaac tggagtggca ctcccccctcg gctgtgattc ctgtcttcct ggcaatgttg   1800
gggatcattg ccaccatctt tgtcatggcc actttcatcc gctacaatga cacgcccatt   1860
gtccgggcat ctgggcggga actcagctat gttcttttga cggcatctt tctttgctac   1920
atcatcactt tcctgatgat tgccaaacca gatgtggcag tgtgttcttt ccggcgagtt   1980
ttcttgggct tgggtatgtg catcagttat gcagccctct tgacgaaaac aaatcggatt   2040
tatcgcatat ttgagcaggg caagaaatca gtaacagctc ccagactcat aagcccaaca   2100
tcacaactgg caatcacttc cagtttaata tcagttcagc ttctaggggt gttcatttgg   2160
tttggtgttg atccacccaa catcatcata gactacgatg aacacaagac aatgaaccct   2220
gagcaagcca gaggggttct caagtgtgac attacagatc tccaaatcat ttgctccttg   2280
ggatatagca ttcttctcat ggtcacatgt actgtgtatg ccatcaagac tcggggtgta   2340
cccgagaatt ttaacgaagc caagcccatt ggattcacta tgtacacgac atgtatagta   2400
tggcttgcct tcattccaat ttttttggc accgctcaat cagcggaaaa gctctacata   2460
caaactacca cgcttacaat ctccatgaac ctaagtgcat cagtggcgct ggggatgcta   2520
tacatgccga aagtgtacat catcattttc caccctgaac tcaatgtcca gaaacggaag   2580
cgaagcttca aggcggtagt cacagcagcc accatgtcat cgaggctgtc acacaaaccc   2640
agtgacagac ccaacggtga ggcaaagacc gagctctgtg aaaacgtaga cccaaacagc   2700
cctgctgcaa aaaagaagta tgtcagttat aataacctgg ttatctaa                 2748
```

<210> SEQ ID NO 67
<211> LENGTH: 915
<212> TYPE: PRT
<213> ORGANISM: Unknown
<220> FEATURE:
<223> OTHER INFORMATION: Novel Sequence

<400> SEQUENCE: 67

```
Met Val Gln Leu Arg Lys Leu Leu Arg Val Leu Thr Leu Met Lys Phe
1               5                   10                  15

Pro Cys Cys Val Leu Glu Val Leu Leu Cys Ala Leu Ala Ala Ala Ala
            20                  25                  30

Arg Gly Gln Glu Met Tyr Ala Pro His Ser Ile Arg Ile Glu Gly Asp
        35                  40                  45

Val Thr Leu Gly Gly Leu Phe Pro Val His Ala Lys Gly Pro Ser Gly
    50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
            100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
    130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350

Arg Thr Leu Glu Asn Asn Arg Arg Asn Val Trp Phe Ala Glu Tyr Trp
        355                 360                 365
```

-continued

```
Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
            420                 425                 430

Tyr Arg Gly Val Cys Pro Glu Met Glu Gln Ala Gly Gly Lys Lys Leu
        435                 440                 445

Leu Lys Tyr Ile Arg Asn Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                485                 490                 495

Gln Trp Thr Asp Glu Leu Gln Leu Asn Ile Glu Asp Met Gln Trp Gly
            500                 505                 510

Lys Gly Val Arg Glu Ile Pro Ala Ser Val Cys Thr Leu Pro Cys Lys
        515                 520                 525

Pro Gly Gln Arg Lys Lys Thr Gln Lys Gly Thr Pro Cys Cys Trp Thr
    530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Ser Ala Val
            580                 585                 590

Ile Pro Val Phe Leu Ala Met Leu Gly Ile Ile Ala Thr Ile Phe Val
        595                 600                 605

Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
        675                 680                 685

Lys Ser Val Thr Ala Pro Arg Leu Ile Ser Pro Thr Ser Gln Leu Ala
    690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
        755                 760                 765

Thr Cys Thr Val Tyr Ala Ile Lys Thr Arg Gly Val Pro Glu Asn Phe
    770                 775                 780
```

-continued

```
Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
        835                 840                 845

Ile Phe His Pro Glu Leu Asn Val Gln Lys Arg Lys Arg Ser Phe Lys
    850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Ser Pro Ala Ala Lys Lys Lys Tyr Val Ser Tyr Asn Asn
            900                 905                 910

Leu Val Ile
        915
```

<210> SEQ ID NO 68
<211> LENGTH: 2748
<212> TYPE: DNA
<213> ORGANISM: Unknown
<220> FEATURE:
<223> OTHER INFORMATION: Novel Sequence

<400> SEQUENCE: 68

```
atggtccagc tgaggaagct gctccgcgtc ctgactttga tgaagttccc ctgctgcgtg     60

ctggaggtgc tcctgtgcgc gctggcggcg gcggcgcgcg gccaggagat gtacgccccg    120

cactcaatcc ggatcgaggg ggacgtcacc ctcggggggc tgttccccgt gcacgccaag    180

ggtcccagcg gagtgccctg cggcgacatc aagagggaaa acgggatcca caggctggaa    240

gcgatgctct acgccctgga ccagatcaac agtgatccca acctactgcc caacgtgacg    300

ctgggcgcgc ggatcctgga cacttgttcc agggacactt acgcgctcga acagtcgctt    360

actttcgtcc aggcgctcat ccagaaggac acctccgacg tgcgctgcac caacggcgaa    420

ccgccggttt tcgtcaagcc ggagaaagta gttggagtga ttggggcttc ggggagttcg    480

gtctccatca tggtagccaa catcctgagg ctcttccaga tcccccagat tagttatgca    540

tcaacggcac ccgagctaag tgatgaccgg cgctatgact tcttctctcg cgtggtgcca    600

cccgattcct tccaagccca ggccatggta gacattgtaa aggccctagg ctggaattat    660

gtgtctaccc tcgcatcgga aggaagttat ggagagaaag gtgtggagtc cttcacgcag    720

atttccaaag aggcaggtgg actctgcatt gcccagtccg tgagaatccc ccaggaacgc    780

aaagacagga ccattgactt tgatagaatt atcaaacagc tcctggacac ccccaactcc    840

agggccgtcg tgatttttgc caacgatgag gatataaagc agatccttgc agcagccaaa    900

agagctgacc aagttggcca ttttctttgg gtgggatcag acagctgggg atccaaaata    960

aacccactgc accagcatga agatatcgca gaaggggcca tcaccattca gcccaagcga   1020

gccacggtgg aagggtttga tgcctacttt acgtcccgta cacttgaaaa caacagaaga   1080

aatgtatggt ttgccgaata ctgggaggaa aacttcaact gcaagttgac gattagtggg   1140

tcaaaaaaag aagacacaga tcgcaaatgc acaggacagg agagaattgg aaaagattcc   1200

aactatgagc aggagggtaa agtccagttc gtgattgacg cagtctatgc tatggctcac   1260
```

-continued

```
gcccttcacc acatgaacaa ggatctctgt gctgactacc ggggtgtctg cccagagatg   1320

gagcaagctg gaggcaagaa gttgctgaag tatatacgca atgttaattt caatggtagt   1380

gctggcactc cagtgatgtt taacaagaac ggggatgcac ctgggcgtta tgacatcttt   1440

cagtaccaga ccacaaacac cagcaacccg ggttaccgtc tgatcgggca gtggacagac   1500

gaacttcagc tcaatataga agacatgcag tggggtaaag gagtccgaga gatacccgcc   1560

tcagtgtgca cactaccatg taagccagga cagagaaaga agacacagaa aggaactcct   1620

tgctgttgga cctgtgagcc ttgcgatggt taccagtacc agtttgatga gatgacatgc   1680

cagcattgcc cctatgacca gaggcccaat gaaaatcgaa ccggatgcca ggatattccc   1740

atcatcaaac tggagtggca ctcccccctgg gctgtgattc ctgtcttcct ggcaatgttg   1800

gggatcattg ccaccatctt tgtcatggcc actttcatcc gctacaatga cacgcccatt   1860

gtccgggcat ctgggcggga actcagctat gttcttttga cgggcatctt tctttgctac   1920

atcatcactt tcctgatgat tgccaaacca gatgtggcag tgtgttcttt ccggcatgtt   1980

ttcttgggct tgggtatgtg catcagttat gcagccctct tgacgaaaac aaatcggatt   2040

tatcgcatat ttgagcaggg caagaaatca gtaacagctc ccagactcat aagcccaaca   2100

tcacaactgg caatcacttc cagtttaata tcagttcagc ttctaggggt gttcatttgg   2160

tttggtgttg atccacccaa catcatcata gactacgatg aacacaagac aatgaaccct   2220

gagcaagcca gagggggttct caagtgtgac attacagatc tccaaatcat ttgctccttg   2280

ggatatagca ttcttctcat ggtcacatgt actgtgtatg ccatcaagac tcggggtgta   2340

cccgagaatt ttaacgaagc caagcccatt ggattcacta tgtacacgac atgtatagta   2400

tggcttgcct tcattccaat tttttttggc accgctcaat cagcggaaaa gctctacata   2460

caaactacca cgcttacaat ctccatgaac ctaagtgcat cagtggcgct ggggatgcta   2520

tacatgccga aagtgtacat catcattttc caccctgaac tcaatgtcca gaaacggaag   2580

cgaagcttca aggcggtagt cacagcagcc accatgtcat cgaggctgtc acacaaaccc   2640

agtgacagac ccaacggtga ggcaaagacc gagctctgtg aaaacgtaga cccaaacagc   2700

cctgctgcaa aaaagaagta tgtcagttat aataacctgg ttatctaa                2748
```

<210> SEQ ID NO 69
<211> LENGTH: 915
<212> TYPE: PRT
<213> ORGANISM: Unknown
<220> FEATURE:
<223> OTHER INFORMATION: Novel Sequence

<400> SEQUENCE: 69

```
Met Val Gln Leu Arg Lys Leu Leu Arg Val Leu Thr Leu Met Lys Phe
1               5                   10                  15

Pro Cys Cys Val Leu Glu Val Leu Leu Cys Ala Leu Ala Ala Ala Ala
            20                  25                  30

Arg Gly Gln Glu Met Tyr Ala Pro His Ser Ile Arg Ile Glu Gly Asp
        35                  40                  45

Val Thr Leu Gly Gly Leu Phe Pro Val His Ala Lys Gly Pro Ser Gly
    50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
```

-continued

```
            100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
    130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350

Arg Thr Leu Glu Asn Asn Arg Arg Asn Val Trp Phe Ala Glu Tyr Trp
        355                 360                 365

Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
            420                 425                 430

Tyr Arg Gly Val Cys Pro Glu Met Glu Gln Ala Gly Gly Lys Lys Leu
        435                 440                 445

Leu Lys Tyr Ile Arg Asn Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                485                 490                 495

Gln Trp Thr Asp Glu Leu Gln Leu Asn Ile Glu Asp Met Gln Trp Gly
            500                 505                 510

Lys Gly Val Arg Glu Ile Pro Ala Ser Val Cys Thr Leu Pro Cys Lys
        515                 520                 525
```

-continued

```
Pro Gly Gln Arg Lys Lys Thr Gln Lys Gly Thr Pro Cys Cys Trp Thr
    530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Trp Ala Val
            580                 585                 590

Ile Pro Val Phe Leu Ala Met Leu Gly Ile Ile Ala Thr Ile Phe Val
        595                 600                 605

Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg His Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
        675                 680                 685

Lys Ser Val Thr Ala Pro Arg Leu Ile Ser Pro Thr Ser Gln Leu Ala
    690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
        755                 760                 765

Thr Cys Thr Val Tyr Ala Ile Lys Thr Arg Gly Val Pro Glu Asn Phe
    770                 775                 780

Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
        835                 840                 845

Ile Phe His Pro Glu Leu Asn Val Gln Lys Arg Lys Arg Ser Phe Lys
    850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Ser Pro Ala Ala Lys Lys Lys Tyr Val Ser Tyr Asn Asn
            900                 905                 910

Leu Val Ile
        915
```

<210> SEQ ID NO 70
<211> LENGTH: 2748

<212> TYPE: DNA
<213> ORGANISM: Unknown
<220> FEATURE:
<223> OTHER INFORMATION: Novel Sequence

<400> SEQUENCE: 70

```
atggtccagc tgaggaagct gctccgcgtc ctgactttga tgaagttccc ctgctgcgtg     60
ctggaggtgc tcctgtgcgc gctggcggcg gcggcgcgcg gccaggagat gtacgccccg    120
cactcaatcc ggatcgaggg ggacgtcacc ctcggggggc tgttccccgt gcacgccaag    180
ggtcccagcg gagtgccctg cggcgacatc aagagggaaa acgggatcca caggctggaa    240
gcgatgctct acgccctgga ccagatcaac agtgatccca acctactgcc caacgtgacg    300
ctgggcgcgc ggatcctgga cacttgttcc agggacactt acgcgctcga acagtcgctt    360
actttcgtcc aggcgctcat ccagaaggac acctccgacg tgcgctgcac caacggcgaa    420
ccgccggttt tcgtcaagcc ggagaaagta gttggagtga ttggggcttc ggggagttcg    480
gtctccatca tggtagccaa catcctgagg ctcttccaga tcccccagat tagttatgca    540
tcaacggcac ccgagctaag tgatgaccgg cgctatgact tcttctctcg cgtggtgcca    600
cccgattcct tccaagccca ggccatggta gacattgtaa aggccctagg ctggaattat    660
gtgtctaccc tcgcatcgga aggaagttat ggagagaaag gtgtggagtc cttcacgcag    720
atttccaaag aggcaggtgg actctgcatt gcccagtccg tgagaatccc ccaggaacgc    780
aaagacagga ccattgactt tgatagaatt atcaaacagc tcctggacac ccccaactcc    840
agggccgtcg tgatttttgc caacgatgag gatataaagc agatccttgc agcagccaaa    900
agagctgacc aagttggcca ttttctttgg gtgggatcag acagctgggg atccaaaata    960
aacccactgc accagcatga agatatcgca gaaggggcca tcaccattca gcccaagcga   1020
gccacggtgg aagggtttga tgcctacttt acgtcccgta cacttgaaaa caacagaaga   1080
aatgtatggt ttgccgaata ctgggaggaa aacttcaact gcaagttgac gattagtggg   1140
tcaaaaaaag aagacacaga tcgcaaatgc acaggacagg agagaattgg aaaagattcc   1200
aactatgagc aggagggtaa agtccagttc gtgattgacg cagtctatgc tatggctcac   1260
gcccttcacc acatgaacaa ggatctctgt gctgactacc ggggtgtctg cccagagatg   1320
gagcaagctg gaggcaagaa gttgctgaag tatatacgca atgttaattt caatggtagt   1380
gctggcactc cagtgatgtt taacaagaac ggggatgcac ctgggcgtta tgacatcttt   1440
cagtaccaga ccacaaacac cagcaacccg ggttaccgtc tgatcgggca gtggacagac   1500
gaacttcagc tcaatataga agacatgcag tggggtaaag gagtccgaga gatacccgcc   1560
tcagtgtgca cactaccatg taagccagga cagagaaaga agacacagaa aggaactcct   1620
tgctgttgga cctgtgagcc ttgcgatggt taccagtacc agtttgatga gatgacatgc   1680
cagcattgcc cctatgacca gaggcccaat gaaaatcgaa ccggatgcca ggatattccc   1740
atcatcaaac tggagtggca ctccccctgg gctgtgattc ctgtcttcct ggcaatgttg   1800
gggatcattg ccaccatctt tgtcatggcc actttcatcc gctacaatga cacgcccatt   1860
gtccgggcat ctgggcggga actcagctat gttcttttga cgggcatctt tctttgctac   1920
atcatcactt tcctgatgat tgccaaacca gatgtggcag tgtgttcttt ccggcgagtt   1980
ttcttgggct tgggtatgtg catcagttat gcagccctct tgacgaaaac aaatcggatt   2040
tatcgcatat ttgagcaggg caagaaatca gtaacagctc ccagactcat aagcccaaca   2100
tcacaactgg caatcacttc cagtttaata tcagttcagc ttctaggggt gttcatttgg   2160
```

-continued

```
tttggtgttg atccacccaa catcatcata gactacgatg aacacaagac aatgaaccct   2220

gagcaagcca gaggggttct caagtgtgac attacagatc tccaaatcat ttgctccttg   2280

ggatatagca ttcttctcat ggtcacatgt tgtgtgtatg ccatcaagac tcggggtgta   2340

cccgagaatt ttaacgaagc caagcccatt ggattcacta tgtacacgac atgtatagta   2400

tggcttgcct tcattccaat ttttttggc accgctcaat cagcggaaaa gctctacata    2460

caaactacca cgcttacaat ctccatgaac ctaagtgcat cagtggcgct ggggatgcta   2520

tacatgccga aagtgtacat catcattttc caccctgaac tcaatgtcca gaaacggaag   2580

cgaagcttca aggcggtagt cacagcagcc accatgtcat cgaggctgtc acacaaaccc   2640

agtgacagac ccaacggtga ggcaaagacc gagctctgtg aaaacgtaga cccaaacagc   2700

cctgctgcaa aaaagaagta tgtcagttat aataacctgg ttatctaa                2748


<210> SEQ ID NO 71
<211> LENGTH: 915
<212> TYPE: PRT
<213> ORGANISM: Unknown
<220> FEATURE:
<223> OTHER INFORMATION: Novel Sequence

<400> SEQUENCE: 71

Met Val Gln Leu Arg Lys Leu Leu Arg Val Leu Thr Leu Met Lys Phe
1               5                   10                  15

Pro Cys Cys Val Leu Glu Val Leu Leu Cys Ala Leu Ala Ala Ala Ala
            20                  25                  30

Arg Gly Gln Glu Met Tyr Ala Pro His Ser Ile Arg Ile Glu Gly Asp
        35                  40                  45

Val Thr Leu Gly Gly Leu Phe Pro Val His Ala Lys Gly Pro Ser Gly
    50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
            100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
    130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
```

-continued

```
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350

Arg Thr Leu Glu Asn Asn Arg Arg Asn Val Trp Phe Ala Glu Tyr Trp
        355                 360                 365

Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
            420                 425                 430

Tyr Arg Gly Val Cys Pro Glu Met Glu Gln Ala Gly Gly Lys Lys Leu
        435                 440                 445

Leu Lys Tyr Ile Arg Asn Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                485                 490                 495

Gln Trp Thr Asp Glu Leu Gln Leu Asn Ile Glu Asp Met Gln Trp Gly
            500                 505                 510

Lys Gly Val Arg Glu Ile Pro Ala Ser Val Cys Thr Leu Pro Cys Lys
        515                 520                 525

Pro Gly Gln Arg Lys Lys Thr Gln Lys Gly Thr Pro Cys Cys Trp Thr
    530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Trp Ala Val
            580                 585                 590

Ile Pro Val Phe Leu Ala Met Leu Gly Ile Ile Ala Thr Ile Phe Val
        595                 600                 605

Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
        675                 680                 685
```

```
Lys Ser Val Thr Ala Pro Arg Leu Ile Ser Pro Thr Ser Gln Leu Ala
    690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
        755                 760                 765

Thr Cys Cys Val Tyr Ala Ile Lys Thr Arg Gly Val Pro Glu Asn Phe
    770                 775                 780

Asn Glu Ala Lys Pro Ile Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
        835                 840                 845

Ile Phe His Pro Glu Leu Asn Val Gln Lys Arg Lys Arg Ser Phe Lys
    850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Ser Pro Ala Ala Lys Lys Lys Tyr Val Ser Tyr Asn Asn
            900                 905                 910

Leu Val Ile
        915
```

<210> SEQ ID NO 72
<211> LENGTH: 2748
<212> TYPE: DNA
<213> ORGANISM: Unknown
<220> FEATURE:
<223> OTHER INFORMATION: Novel Sequence

<400> SEQUENCE: 72

```
atggtccagc tgaggaagct gctccgcgtc ctgactttga tgaagttccc ctgctgcgtg     60

ctggaggtgc tcctgtgcgc gctggcggcg gcggcgcgcg gccaggagat gtacgccccg    120

cactcaatcc ggatcgaggg ggacgtcacc ctcgggggc tgttccccgt gcacgccaag    180

ggtcccagcg gagtgccctg cggcgacatc aagagggaaa acgggatcca caggctggaa    240

gcgatgctct acgccctgga ccagatcaac agtgatccca acctactgcc caacgtgacg    300

ctgggcgcgc ggatcctgga cacttgttcc agggacactt acgcgctcga acagtcgctt    360

actttcgtcc aggcgctcat ccagaaggac acctccgacg tgcgctgcac caacggcgaa    420

ccgccggttt tcgtcaagcc ggagaaagta gttggagtga ttggggcttc ggggagttcg    480

gtctccatca tggtagccaa catcctgagg ctcttccaga tcccccagat tagttatgca    540

tcaacggcac ccgagctaag tgatgaccgg cgctatgact tcttctctcg cgtggtgcca    600

cccgattcct tccaagccca ggccatggta gacattgtaa aggccctagg ctggaattat    660

gtgtctaccc tcgcatcgga aggaagttat ggagagaaag gtgtggagtc cttcacgcag    720
```

-continued

```
atttccaaag aggcaggtgg actctgcatt gcccagtccg tgagaatccc ccaggaacgc    780
aaagacagga ccattgactt tgatagaatt atcaaacagc tcctggacac ccccaactcc    840
agggccgtcg tgatttttgc caacgatgag gatataaagc agatccttgc agcagccaaa    900
agagctgacc aagttggcca ttttctttgg gtgggatcag acagctgggg atccaaaata    960
aacccactgc accagcatga agatatcgca gaaggggcca tcaccattca gcccaagcga   1020
gccacggtgg aagggtttga tgcctacttt acgtcccgta cacttgaaaa caacagaaga   1080
aatgtatggt ttgccgaata ctgggaggaa aacttcaact gcaagttgac gattagtggg   1140
tcaaaaaaag aagacacaga tcgcaaatgc acaggacagg agagaattgg aaaagattcc   1200
aactatgagc aggagggtaa agtccagttc gtgattgacg cagtctatgc tatggctcac   1260
gcccttcacc acatgaacaa ggatctctgt gctgactacc ggggtgtctg cccagagatg   1320
gagcaagctg gaggcaagaa gttgctgaag tatatacgca atgttaattt caatggtagt   1380
gctggcactc cagtgatgtt taacaagaac ggggatgcac ctgggcgtta tgacatcttt   1440
cagtaccaga ccacaaacac cagcaacccg ggttaccgtc tgatcgggca gtggacagac   1500
gaacttcagc tcaatataga agacatgcag tggggtaaag gagtccgaga gatacccgcc   1560
tcagtgtgca cactaccatg taagccagga cagagaaaga agacacagaa aggaactcct   1620
tgctgttgga cctgtgagcc ttgcgatggt taccagtacc agtttgatga gatgacatgc   1680
cagcattgcc cctatgacca gaggcccaat gaaaatcgaa ccggatgcca ggatattccc   1740
atcatcaaac tggagtggca ctccccctgg gctgtgattc ctgtcttcct ggcaatgttg   1800
gggatcattg ccaccatctt tgtcatggcc actttcatcc gctacaatga cacgcccatt   1860
gtccgggcat ctgggcggga actcagctat gttcttttga cgggcatctt tctttgctac   1920
atcatcactt tcctgatgat tgccaaacca gatgtggcag tgtgttcttt ccggcgagtt   1980
ttcttgggct tgggtatgtg catcagttat gcagccctct tgacgaaaac aaatcggatt   2040
tatcgcatat ttgagcaggg caagaaatca gtaacagctc ccagactcat aagcccaaca   2100
tcacaactgg caatcacttc cagtttaata tcagttcagc ttctaggggt gttcatttgg   2160
tttggtgttg atccacccaa catcatcata gactacgatg aacacaagac aatgaaccct   2220
gagcaagcca gaggggttct caagtgtgac attacagatc tccaaatcat ttgctccttg   2280
ggatatagca ttcttctcat ggtcacatgt actgtgtatg ccatcaagac tcggggtgta   2340
cccgagaatt ttaacgaagc caagcccaag ggattcacta tgtacacgac atgtatagta   2400
tggcttgcct tcattccaat tttttttggc accgctcaat cagcggaaaa gctctacata   2460
caaactacca cgcttacaat ctccatgaac ctaagtgcat cagtggcgct ggggatgcta   2520
tacatgccga aagtgtacat catcattttc caccctgaac tcaatgtcca gaaacggaag   2580
cgaagcttca aggcggtagt cacagcagcc accatgtcat cgaggctgtc acacaaaccc   2640
agtgacagac ccaacggtga ggcaaagacc gagctctgtg aaaacgtaga cccaaacagc   2700
cctgctgcaa aaaagaagta tgtcagttat aataacctgg ttatctaa                2748
```

<210> SEQ ID NO 73
<211> LENGTH: 915
<212> TYPE: PRT
<213> ORGANISM: Unknown
<220> FEATURE:
<223> OTHER INFORMATION: Novel Sequence

<400> SEQUENCE: 73

-continued

```
Met Val Gln Leu Arg Lys Leu Leu Arg Val Leu Thr Leu Met Lys Phe
1               5                   10                  15

Pro Cys Cys Val Leu Glu Val Leu Leu Cys Ala Leu Ala Ala Ala Ala
            20                  25                  30

Arg Gly Gln Glu Met Tyr Ala Pro His Ser Ile Arg Ile Glu Gly Asp
        35                  40                  45

Val Thr Leu Gly Gly Leu Phe Pro Val His Ala Lys Gly Pro Ser Gly
    50                  55                  60

Val Pro Cys Gly Asp Ile Lys Arg Glu Asn Gly Ile His Arg Leu Glu
65                  70                  75                  80

Ala Met Leu Tyr Ala Leu Asp Gln Ile Asn Ser Asp Pro Asn Leu Leu
                85                  90                  95

Pro Asn Val Thr Leu Gly Ala Arg Ile Leu Asp Thr Cys Ser Arg Asp
            100                 105                 110

Thr Tyr Ala Leu Glu Gln Ser Leu Thr Phe Val Gln Ala Leu Ile Gln
        115                 120                 125

Lys Asp Thr Ser Asp Val Arg Cys Thr Asn Gly Glu Pro Pro Val Phe
    130                 135                 140

Val Lys Pro Glu Lys Val Val Gly Val Ile Gly Ala Ser Gly Ser Ser
145                 150                 155                 160

Val Ser Ile Met Val Ala Asn Ile Leu Arg Leu Phe Gln Ile Pro Gln
                165                 170                 175

Ile Ser Tyr Ala Ser Thr Ala Pro Glu Leu Ser Asp Asp Arg Arg Tyr
            180                 185                 190

Asp Phe Phe Ser Arg Val Val Pro Pro Asp Ser Phe Gln Ala Gln Ala
        195                 200                 205

Met Val Asp Ile Val Lys Ala Leu Gly Trp Asn Tyr Val Ser Thr Leu
    210                 215                 220

Ala Ser Glu Gly Ser Tyr Gly Glu Lys Gly Val Glu Ser Phe Thr Gln
225                 230                 235                 240

Ile Ser Lys Glu Ala Gly Gly Leu Cys Ile Ala Gln Ser Val Arg Ile
                245                 250                 255

Pro Gln Glu Arg Lys Asp Arg Thr Ile Asp Phe Asp Arg Ile Ile Lys
            260                 265                 270

Gln Leu Leu Asp Thr Pro Asn Ser Arg Ala Val Val Ile Phe Ala Asn
        275                 280                 285

Asp Glu Asp Ile Lys Gln Ile Leu Ala Ala Ala Lys Arg Ala Asp Gln
    290                 295                 300

Val Gly His Phe Leu Trp Val Gly Ser Asp Ser Trp Gly Ser Lys Ile
305                 310                 315                 320

Asn Pro Leu His Gln His Glu Asp Ile Ala Glu Gly Ala Ile Thr Ile
                325                 330                 335

Gln Pro Lys Arg Ala Thr Val Glu Gly Phe Asp Ala Tyr Phe Thr Ser
            340                 345                 350

Arg Thr Leu Glu Asn Asn Arg Arg Asn Val Trp Phe Ala Glu Tyr Trp
        355                 360                 365

Glu Glu Asn Phe Asn Cys Lys Leu Thr Ile Ser Gly Ser Lys Lys Glu
    370                 375                 380

Asp Thr Asp Arg Lys Cys Thr Gly Gln Glu Arg Ile Gly Lys Asp Ser
385                 390                 395                 400

Asn Tyr Glu Gln Glu Gly Lys Val Gln Phe Val Ile Asp Ala Val Tyr
                405                 410                 415

Ala Met Ala His Ala Leu His His Met Asn Lys Asp Leu Cys Ala Asp
```

```
            420                 425                 430

Tyr Arg Gly Val Cys Pro Glu Met Glu Gln Ala Gly Gly Lys Lys Leu
        435                 440                 445

Leu Lys Tyr Ile Arg Asn Val Asn Phe Asn Gly Ser Ala Gly Thr Pro
    450                 455                 460

Val Met Phe Asn Lys Asn Gly Asp Ala Pro Gly Arg Tyr Asp Ile Phe
465                 470                 475                 480

Gln Tyr Gln Thr Thr Asn Thr Ser Asn Pro Gly Tyr Arg Leu Ile Gly
                485                 490                 495

Gln Trp Thr Asp Glu Leu Gln Leu Asn Ile Glu Asp Met Gln Trp Gly
            500                 505                 510

Lys Gly Val Arg Glu Ile Pro Ala Ser Val Cys Thr Leu Pro Cys Lys
        515                 520                 525

Pro Gly Gln Arg Lys Lys Thr Gln Lys Gly Thr Pro Cys Cys Trp Thr
    530                 535                 540

Cys Glu Pro Cys Asp Gly Tyr Gln Tyr Gln Phe Asp Glu Met Thr Cys
545                 550                 555                 560

Gln His Cys Pro Tyr Asp Gln Arg Pro Asn Glu Asn Arg Thr Gly Cys
                565                 570                 575

Gln Asp Ile Pro Ile Ile Lys Leu Glu Trp His Ser Pro Trp Ala Val
            580                 585                 590

Ile Pro Val Phe Leu Ala Met Leu Gly Ile Ile Ala Thr Ile Phe Val
        595                 600                 605

Met Ala Thr Phe Ile Arg Tyr Asn Asp Thr Pro Ile Val Arg Ala Ser
    610                 615                 620

Gly Arg Glu Leu Ser Tyr Val Leu Leu Thr Gly Ile Phe Leu Cys Tyr
625                 630                 635                 640

Ile Ile Thr Phe Leu Met Ile Ala Lys Pro Asp Val Ala Val Cys Ser
                645                 650                 655

Phe Arg Arg Val Phe Leu Gly Leu Gly Met Cys Ile Ser Tyr Ala Ala
            660                 665                 670

Leu Leu Thr Lys Thr Asn Arg Ile Tyr Arg Ile Phe Glu Gln Gly Lys
        675                 680                 685

Lys Ser Val Thr Ala Pro Arg Leu Ile Ser Pro Thr Ser Gln Leu Ala
    690                 695                 700

Ile Thr Ser Ser Leu Ile Ser Val Gln Leu Leu Gly Val Phe Ile Trp
705                 710                 715                 720

Phe Gly Val Asp Pro Pro Asn Ile Ile Ile Asp Tyr Asp Glu His Lys
                725                 730                 735

Thr Met Asn Pro Glu Gln Ala Arg Gly Val Leu Lys Cys Asp Ile Thr
            740                 745                 750

Asp Leu Gln Ile Ile Cys Ser Leu Gly Tyr Ser Ile Leu Leu Met Val
        755                 760                 765

Thr Cys Thr Val Tyr Ala Ile Lys Thr Arg Gly Val Pro Glu Asn Phe
    770                 775                 780

Asn Glu Ala Lys Pro Lys Gly Phe Thr Met Tyr Thr Thr Cys Ile Val
785                 790                 795                 800

Trp Leu Ala Phe Ile Pro Ile Phe Phe Gly Thr Ala Gln Ser Ala Glu
                805                 810                 815

Lys Leu Tyr Ile Gln Thr Thr Thr Leu Thr Ile Ser Met Asn Leu Ser
            820                 825                 830

Ala Ser Val Ala Leu Gly Met Leu Tyr Met Pro Lys Val Tyr Ile Ile
        835                 840                 845
```

-continued

```
Ile Phe His Pro Glu Leu Asn Val Gln Lys Arg Lys Arg Ser Phe Lys
    850                 855                 860

Ala Val Val Thr Ala Ala Thr Met Ser Ser Arg Leu Ser His Lys Pro
865                 870                 875                 880

Ser Asp Arg Pro Asn Gly Glu Ala Lys Thr Glu Leu Cys Glu Asn Val
                885                 890                 895

Asp Pro Asn Ser Pro Ala Ala Lys Lys Lys Tyr Val Ser Tyr Asn Asn
            900                 905                 910

Leu Val Ile
        915
```

<210> SEQ ID NO 74
<211> LENGTH: 1842
<212> TYPE: DNA
<213> ORGANISM: Unknown
<220> FEATURE:
<223> OTHER INFORMATION: Novel Sequence

<400> SEQUENCE: 74

```
atgcgagccc cgggcgcgct tctcgcccgc atgtcgcggc tactgcttct gctactgctc     60

aaggtgtctg cctcttctgc cctcggggtc gcccctgcgt ccagaaacga aacttgtctg    120

ggggagagct gtgcacctac agtgatccag cgccgcggca gggacgcctg gggaccggga    180

aattctgcaa gagacgttct gcgagcccga gcacccaggg aggagcaggg ggcagcgttt    240

cttgcgggac cctcctggga cctgccggcg gccccgggcc gtgacccggc tgcaggcaga    300

ggggcggagg cgtcggcagc cggacccccg ggacctccaa ccaggccacc tggcccctgg    360

aggtggaaag gtgctcgggg tcaggagcct tctgaaactt tggggagagg gaaccccacg    420

gccctccagc tcttccttca gatctcagag gaggaagaga agggtcccag aggcgctggc    480

atttccgggc gtagccagga gcagagtgtg aagacagtcc ccggagccag cgatcttttt    540

tactggccaa ggagagccgg gaaactccag ggttcccacc acaagcccct gtccaagacg    600

gccaatggac tggcggggca cgaagggtgg acaattgcac tcccgggccg ggcgctggcc    660

cagaatggat ccttgggtga aggaatccat gagcctgggg gtccccgccg gggaaacagc    720

acgaaccggc gtgtgagact gaagaacccc ttctacccgc tgacccagga gtcctatgga    780

gcctacgcgg tcatgtgtct gtccgtggtg atcttcggga ccggcatcat tggcaacctg    840

gcggtgatgt gcatcgtgtg ccacaactac tacatgcgga gcatctccaa ctccctcttg    900

gccaacctgg ccttctggga ctttctcatc atcttcttct gccttccgct ggtcatcttc    960

cacgagctga ccaagaagtg gctgctggag gacttctcct gcaagatcgt gccctatata   1020

gaggtcgctt ctctgggagt caccaccttc acccgatgtg ctctgtgcat agaccgcttc   1080

cgtgctgcca ccaacgtaca gatgtactac gaaatgatcg aaaactgttc ctcaacaact   1140

gccaaacttg ctgttatatg ggtgggagct ctattgttag cacttccaga agttgttctc   1200

cgccagctga gcaaggagga tttggggttt agtggccgag ctccggcaga aaggtgcatt   1260

attaagatct ctcctgattt accagacacc atctatgttc tagccctcac ctacgacagt   1320

gcgagactgt ggtggtattt tggctgttac ttttgtttgc ccacgctttt caccatcacc   1380

tgctctctag tgactgcgag gaaaatccgc aaagcagaga aagcctgtac ccgagggaat   1440

aaacggcaga ttcaactaga gagtcagatg aactgtacag tagtggcact gaccatttta   1500

tatggatttt gcattattcc tgaaaatatc tgcaacattg ttactgccta catggctaca   1560

ggggtttcac agcagacaat ggacctcctt aatatcatca gccagttcct tttgttcttt   1620
```

```
aagtcctgtg tcaccccagt cctccttttc tgtctctgca aacccttcag tcgggccttc   1680

atggagtgct gctgctgttg ctgtgaggaa tgcattcaga agtcttcaac ggtgaccagt   1740

gatgacaatg acaacgagta caccacggaa ctcgaactct cgcctttcag taccatacgc   1800

cgtgaaatgt ccacttttgc ttctgtcgga actcattgct ga                      1842


<210> SEQ ID NO 75
<211> LENGTH: 613
<212> TYPE: PRT
<213> ORGANISM: Unknown
<220> FEATURE:
<223> OTHER INFORMATION: Novel Sequence

<400> SEQUENCE: 75

Met Arg Ala Pro Gly Ala Leu Leu Ala Arg Met Ser Arg Leu Leu Leu
1               5                   10                  15

Leu Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110

Pro Thr Arg Pro Pro Gly Pro Trp Arg Trp Lys Gly Ala Arg Gly Gln
        115                 120                 125

Glu Pro Ser Glu Thr Leu Gly Arg Gly Asn Pro Thr Ala Leu Gln Leu
    130                 135                 140

Phe Leu Gln Ile Ser Glu Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Cys Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
305                 310                 315                 320
```

-continued

```
His Glu Leu Thr Lys Lys Trp Leu Leu Glu Asp Phe Ser Cys Lys Ile
                325                 330                 335

Val Pro Tyr Ile Glu Val Ala Ser Leu Gly Val Thr Thr Phe Thr Arg
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Asn Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Cys Val
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610
```

<210> SEQ ID NO 76
<211> LENGTH: 1842
<212> TYPE: DNA
<213> ORGANISM: Homo sapiens

<400> SEQUENCE: 76

```
atgcgagccc cgggcgcgct tctcgcccgc atgtcgcggc tactgcttct gctactgctc      60

aaggtgtctg cctcttctgc cctcggggtc gcccctgcgt ccagaaacga aacttgtctg     120

ggggagagct gtgcacctac agtgatccag cgccgcggca gggacgcctg ggaccggga     180

aattctgcaa gagacgttct gcgagcccga gcacccaggg aggagcaggg ggcagcgttt     240

cttgcgggac cctcctggga cctgccggcg gccccgggcc gtgacccggc tgcaggcaga     300

ggggcggagg cgtcggcagc cggacccccg ggacctccaa ccaggccacc tggcccctgg     360

aggtggaaag gtgctcgggg tcaggagcct tctgaaactt tggggagagg gaaccccacg     420
```

-continued

```
gccctccagc tcttccttca gatctcagag gaggaagaga agggtcccag aggcgctggc    480
atttccgggc gtagccagga gcagagtgtg aagacagtcc ccggagccag cgatcttttt    540
tactggccaa ggagagccgg gaaactccag ggttcccacc acaagcccct gtccaagacg    600
gccaatggac tggcggggca cgaagggtgg acaattgcac tcccgggccg ggcgctggcc    660
cagaatggat ccttgggtga aggaatccat gagcctgggg gtccccgccg gggaaacagc    720
acgaaccggc gtgtgagact gaagaacccc ttctacccgc tgacccagga gtcctatgga    780
gcctacgcgg tcatgtgtct gtccgtggtg atcttcggga ccggcatcat tggcaacctg    840
gcggtgatgt gcatcgtgtg ccacaactac tacatgcgga gcatctccaa ctccctcttg    900
gccaacctgg ccttctggga ctttctcatc atcttcttct gccttccgct ggtcatcttc    960
cacgagctga ccaagaagtg gctgctggag gacttctcct gcaagatcgt gccctatata   1020
gaggtcgctt ctctgggagt caccaccttc accttatgtg ctctgtgcat agaccgcttc   1080
cgtgctgcca ccaacgtaca gatgtactac gaaatgatcg aaaactgttc ctcaacaact   1140
gccaaacttg ctgttatatg ggtgggagct ctattgttag cacttccaga agttgttctc   1200
cgccagctga gcaaggagga tttggggttt agtggccgag ctccggcaga aaggtgcatt   1260
attaagatct ctcctgattt accagacacc atctatgttc tagccctcac ctacgacagt   1320
gcgagactgt ggtggtattt tggctgttac ttttgtttgc ccacgctttt caccatcacc   1380
tgctctctag tgactgcgag gaaaatccgc aaagcagaga aagcctgtac ccgagggaat   1440
aaacggcaga ttcaactaga gagtcagatg aactgtacag tagtggcact gaccatttta   1500
tatggatttt gcattattcc tgaaaatatc tgcaacattg ttactgccta catggctaca   1560
ggggtttcac agcagacaat ggacctcctt aatatcatca gccagttcct tttgttcttt   1620
aagtcctatg tcaccccagt cctccttttc tgtctctgca aacccttcag tcgggccttc   1680
atggagtgct gctgctgttg ctgtgaggaa tgcattcaga agtcttcaac ggtgaccagt   1740
gatgacaatg acaacgagta caccacggaa ctcgaactct cgcctttcag taccatacgc   1800
cgtgaaatgt ccacttttgc ttctgtcgga actcattgct ga                      1842
```

<210> SEQ ID NO 77
<211> LENGTH: 613
<212> TYPE: PRT
<213> ORGANISM: Unknown
<220> FEATURE:
<223> OTHER INFORMATION: Novel Sequence

<400> SEQUENCE: 77

```
Met Arg Ala Pro Gly Ala Leu Leu Ala Arg Met Ser Arg Leu Leu Leu
1               5                   10                  15

Leu Leu Leu Leu Lys Val Ser Ala Ser Ser Ala Leu Gly Val Ala Pro
            20                  25                  30

Ala Ser Arg Asn Glu Thr Cys Leu Gly Glu Ser Cys Ala Pro Thr Val
        35                  40                  45

Ile Gln Arg Arg Gly Arg Asp Ala Trp Gly Pro Gly Asn Ser Ala Arg
    50                  55                  60

Asp Val Leu Arg Ala Arg Ala Pro Arg Glu Glu Gln Gly Ala Ala Phe
65                  70                  75                  80

Leu Ala Gly Pro Ser Trp Asp Leu Pro Ala Ala Pro Gly Arg Asp Pro
                85                  90                  95

Ala Ala Gly Arg Gly Ala Glu Ala Ser Ala Ala Gly Pro Pro Gly Pro
            100                 105                 110
```

-continued

```
Pro Thr Arg Pro Pro Gly Pro Trp Arg Trp Lys Gly Ala Arg Gly Gln
        115                 120                 125

Glu Pro Ser Glu Thr Leu Gly Arg Gly Asn Pro Thr Ala Leu Gln Leu
    130                 135                 140

Phe Leu Gln Ile Ser Glu Glu Glu Lys Gly Pro Arg Gly Ala Gly
145                 150                 155                 160

Ile Ser Gly Arg Ser Gln Glu Gln Ser Val Lys Thr Val Pro Gly Ala
                165                 170                 175

Ser Asp Leu Phe Tyr Trp Pro Arg Arg Ala Gly Lys Leu Gln Gly Ser
            180                 185                 190

His His Lys Pro Leu Ser Lys Thr Ala Asn Gly Leu Ala Gly His Glu
        195                 200                 205

Gly Trp Thr Ile Ala Leu Pro Gly Arg Ala Leu Ala Gln Asn Gly Ser
    210                 215                 220

Leu Gly Glu Gly Ile His Glu Pro Gly Gly Pro Arg Arg Gly Asn Ser
225                 230                 235                 240

Thr Asn Arg Arg Val Arg Leu Lys Asn Pro Phe Tyr Pro Leu Thr Gln
                245                 250                 255

Glu Ser Tyr Gly Ala Tyr Ala Val Met Cys Leu Ser Val Val Ile Phe
            260                 265                 270

Gly Thr Gly Ile Ile Gly Asn Leu Ala Val Met Cys Ile Val Cys His
        275                 280                 285

Asn Tyr Tyr Met Arg Ser Ile Ser Asn Ser Leu Leu Ala Asn Leu Ala
    290                 295                 300

Phe Trp Asp Phe Leu Ile Ile Phe Phe Cys Leu Pro Leu Val Ile Phe
305                 310                 315                 320

His Glu Leu Thr Lys Lys Trp Leu Leu Glu Asp Phe Ser Cys Lys Ile
                325                 330                 335

Val Pro Tyr Ile Glu Val Ala Ser Leu Gly Val Thr Thr Phe Thr Leu
            340                 345                 350

Cys Ala Leu Cys Ile Asp Arg Phe Arg Ala Ala Thr Asn Val Gln Met
        355                 360                 365

Tyr Tyr Glu Met Ile Glu Asn Cys Ser Ser Thr Thr Ala Lys Leu Ala
    370                 375                 380

Val Ile Trp Val Gly Ala Leu Leu Leu Ala Leu Pro Glu Val Val Leu
385                 390                 395                 400

Arg Gln Leu Ser Lys Glu Asp Leu Gly Phe Ser Gly Arg Ala Pro Ala
                405                 410                 415

Glu Arg Cys Ile Ile Lys Ile Ser Pro Asp Leu Pro Asp Thr Ile Tyr
            420                 425                 430

Val Leu Ala Leu Thr Tyr Asp Ser Ala Arg Leu Trp Trp Tyr Phe Gly
        435                 440                 445

Cys Tyr Phe Cys Leu Pro Thr Leu Phe Thr Ile Thr Cys Ser Leu Val
    450                 455                 460

Thr Ala Arg Lys Ile Arg Lys Ala Glu Lys Ala Cys Thr Arg Gly Asn
465                 470                 475                 480

Lys Arg Gln Ile Gln Leu Glu Ser Gln Met Asn Cys Thr Val Val Ala
                485                 490                 495

Leu Thr Ile Leu Tyr Gly Phe Cys Ile Ile Pro Glu Asn Ile Cys Asn
            500                 505                 510

Ile Val Thr Ala Tyr Met Ala Thr Gly Val Ser Gln Gln Thr Met Asp
        515                 520                 525

Leu Leu Asn Ile Ile Ser Gln Phe Leu Leu Phe Phe Lys Ser Tyr Val
```

-continued

```
    530                 535                 540

Thr Pro Val Leu Leu Phe Cys Leu Cys Lys Pro Phe Ser Arg Ala Phe
545                 550                 555                 560

Met Glu Cys Cys Cys Cys Cys Cys Glu Glu Cys Ile Gln Lys Ser Ser
                565                 570                 575

Thr Val Thr Ser Asp Asp Asn Asp Asn Glu Tyr Thr Thr Glu Leu Glu
            580                 585                 590

Leu Ser Pro Phe Ser Thr Ile Arg Arg Glu Met Ser Thr Phe Ala Ser
        595                 600                 605

Val Gly Thr His Cys
    610


<210> SEQ ID NO 78
<211> LENGTH: 1086
<212> TYPE: DNA
<213> ORGANISM: Unknown
<220> FEATURE:
<223> OTHER INFORMATION: Novel Sequence

<400> SEQUENCE: 78

atgtcccctg aatgcgcgcg ggcagcgggc gacgcgccct tgcgcagcct ggagcaagcc     60

aaccgcaccc gctttccctt cttctccgac gtcaagggcg accaccggct ggtgctggcc    120

gcggtggaga caaccgtgct ggtgctcatc tttgcagtgt cgctgctggg caacgtgtgc    180

gccctggtgc tggtggcgcg ccgacgacgc cgcggcgcga ctgcctgcct ggtactcaac    240

ctcttctgcg cggacctgct cttcatcagc gctatccctc tggtgctggc cgtgcgctgg    300

actgaggcct ggctgctggg ccccgttgcc tgccacctgc tcttctacgt gatgaccctg    360

agcggcagcg tcaccatcct cacgctggcc gcggtcagcc tggagcgcat ggtgtgcatc    420

gtgcacctgc agcgcggcgt gcggggtcct gggcggcggg cgcgggcagt gctgctggcg    480

ctcatctggg gctattcggc ggtcgccgct ctgcctctct gcgtcttctt tcgagtcgtc    540

ccgcaacggc tccccggcgc cgaccaggaa atttcgattt gcacactgat ttggcccacc    600

attcctggag agatctcgtg ggatgtctct tttgttactt tgaacttctt ggtgccagga    660

ctggtcattg tgatcagtta ctccaaaatt ttacagatca caaaggcatc aaggaagagg    720

ctcacggtaa gcctggccta ctcggagagc caccagatcc gcgtgtccca gcaggacttc    780

cggctcttcc gcaccctctt cctcctcatg gtctccttct tcatcatgtg gagccccatc    840

ttcatcacca tcctcctcat cctgatccag aacttcaagc aagacctggt catctggccg    900

tccctcttct tctgggtggt ggccttcaca tttgctaatt cagccctaaa ccccatcctc    960

tacaacatga cactgtgcag gaatgagtgg aagaaaattt tttgctgctt ctggttccca   1020

gaaaagggag ccattttaac agacacatct gtcaaaagaa atgacttgtc gattatttct   1080

ggctaa                                                               1086


<210> SEQ ID NO 79
<211> LENGTH: 361
<212> TYPE: PRT
<213> ORGANISM: Unknown
<220> FEATURE:
<223> OTHER INFORMATION: Novel Sequence

<400> SEQUENCE: 79

Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
```

-continued

```
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
                85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Glu Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
                165                 170                 175

Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
        195                 200                 205

Val Ser Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240

Leu Thr Val Ser Leu Ala Tyr Ser Glu Ser His Gln Ile Arg Val Ser
                245                 250                 255

Gln Gln Asp Phe Arg Leu Phe Arg Thr Leu Phe Leu Leu Met Val Ser
            260                 265                 270

Phe Phe Ile Met Trp Ser Pro Ile Phe Ile Thr Ile Leu Leu Ile Leu
        275                 280                 285

Ile Gln Asn Phe Lys Gln Asp Leu Val Ile Trp Pro Ser Leu Phe Phe
    290                 295                 300

Trp Val Val Ala Phe Thr Phe Ala Asn Ser Ala Leu Asn Pro Ile Leu
305                 310                 315                 320

Tyr Asn Met Thr Leu Cys Arg Asn Glu Trp Lys Lys Ile Phe Cys Cys
                325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
        355                 360
```

<210> SEQ ID NO 80
<211> LENGTH: 1086
<212> TYPE: DNA
<213> ORGANISM: Unknown
<220> FEATURE:
<223> OTHER INFORMATION: Novel Sequence

<400> SEQUENCE: 80

```
atgtcccctg aatgcgcgcg ggcagcgggc gacgcgccct tgcgcagcct ggagcaagcc      60

aaccgcaccc gctttccctt cttctccgac gtcaagggcg accaccggct ggtgctggcc     120
```

-continued

```
gcggtggaga caaccgtgct ggtgctcatc tttgcagtgt cgctgctggg caacgtgtgc    180

gccctggtgc tggtggcgcg ccgacgacgc cgcggcgcga ctgcctgcct ggtactcaac    240

ctcttctgcg cggacctgct cttcatcagc gctatccctc tggtgctggc cgtgcgctgg    300

actgaggcct ggctgctggg ccccgttgcc tgccacctgc tcttctacgt gatgaccctg    360

agcggcagcg tcaccatcct cacgctggcc gcggtcagcc tgaatcgcat ggtgtgcatc    420

gtgcacctgc agcgcggcgt gcggggtcct gggcggcggg cgcgggcagt gctgctggcg    480

ctcatctggg gctattcggc ggtcgccgct ctgcctctct gcgtcttctt tcgagtcgtc    540

ccgcaacggc tccccggcgc cgaccaggaa atttcgattt gcacactgat ttggcccacc    600

attcctggag agatctcgtg ggatgtctct tttgttactt tgaacttctt ggtgccagga    660

ctggtcattg tgatcagtta ctccaaaatt ttacagatca caaaggcatc aaggaagagg    720

ctcacggtaa gcctggccta ctcggagagc caccagatcc gcgtgtccca gcaggacttc    780

cggctcttcc gcaccctctt cctcctcatg gtctccttct tcatcatgtg gagccccatc    840

atcatcacca tcctcctcat cctgatccag aacttcaagc aagacctggt catctggccg    900

tccctcttct tctgggtggt ggccttcaca tttgctaatt cagccctaaa ccccatcctc    960

tacaacatga cactgtgcag gaatgagtgg aagaaaattt tttgctgctt ctggttccca   1020

gaaaagggag ccattttaac agacacatct gtcaaaagaa atgacttgtc gattatttct   1080

ggctaa                                                               1086
```

<210> SEQ ID NO 81
<211> LENGTH: 361
<212> TYPE: PRT
<213> ORGANISM: Unknown
<220> FEATURE:
<223> OTHER INFORMATION: Novel Sequence

<400> SEQUENCE: 81

```
Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
                85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Asn Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
                165                 170                 175

Phe Arg Val Val Pro Gln Arg Leu Pro Gly Ala Asp Gln Glu Ile Ser
            180                 185                 190
```

-continued

```
Ile Cys Thr Leu Ile Trp Pro Thr Ile Pro Gly Glu Ile Ser Trp Asp
        195                 200                 205

Val Ser Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240

Leu Thr Val Ser Leu Ala Tyr Ser Glu Ser His Gln Ile Arg Val Ser
                245                 250                 255

Gln Gln Asp Phe Arg Leu Phe Arg Thr Leu Phe Leu Leu Met Val Ser
            260                 265                 270

Phe Phe Ile Met Trp Ser Pro Ile Ile Ile Thr Ile Leu Leu Ile Leu
        275                 280                 285

Ile Gln Asn Phe Lys Gln Asp Leu Val Ile Trp Pro Ser Leu Phe Phe
    290                 295                 300

Trp Val Val Ala Phe Thr Phe Ala Asn Ser Ala Leu Asn Pro Ile Leu
305                 310                 315                 320

Tyr Asn Met Thr Leu Cys Arg Asn Glu Trp Lys Lys Ile Phe Cys Cys
                325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
        355                 360
```

<210> SEQ ID NO 82
<211> LENGTH: 1212
<212> TYPE: DNA
<213> ORGANISM: Unknown
<220> FEATURE:
<223> OTHER INFORMATION: Novel Sequence

<400> SEQUENCE: 82

```
atggcttgca atggcagtgc ggccaggggg cactttgacc ctgaggactt gaacctgact     60

gacgaggcac tgagactcaa gtacctgggg ccccagcaga cagagctgtt catgcccatc    120

tgtgccacat acctgctgat cttcgtggtg ggcgctgtgg gcaatgggct gacctgtctg    180

gtcatcctgc gccacaaggc catgcgcacg cctaccaact actacctctt cagcctggcc    240

gtgtcggacc tgctggtgct gctggtgggc ctgcccctgg agctctatga gatgtggcac    300

aactacccct tcctgctggg cgttggtggc tgctatttcc gcacgctact gtttgagatg    360

gtctgcctgg cctcagtgct caacgtcact gccctgagcg tggaacgcta tgtggccgtg    420

gtgcacccac tccaggccag gtccatggtg acgcgggccc atgtgcgccg agtgcttggg    480

gccgtctggg gtcttgccat gctctgctcc ctgcccaaca ccagcctgca cggcatccgg    540

cagctgcacg tgccctgccg ggcccagtg ccagactcag ctgtttgcat gctggtccgc    600

ccacgggccc tctacaacat ggtagtgcag accaccgcgc tgctcttctt ctgcctgccc    660

atggccatca tgagcgtgct ctacctgctc attgggctgc gactgcggcg ggagaggctg    720

ctgctcatgc aggaggccaa gggcaggggc tctgcagcag ccaggtccag atacacctgc    780

aggctccagc agcacgatcg gggccggaga caagtgaaaa agatgctgtt tgtcctggtc    840

gtggtgtttg gcatctgctg ggccccgttc cacgccgacc gcgtcatgtg gagcgtcgtg    900

tcacagtgga cagatggcct gcacctggcc ttccagcacg tgcacgtcat ctccggcatc    960

ttcttctacc tgggctcggc ggccaacccc gtgctctata gcctcatgtc cagccgcttc   1020

cgagagacct tccaggaggc cctgtgcctc ggggcctgct gccatcgcct cagaccccgc   1080
```

```
cacagctccc acagcctcag caggatgacc acaggcagca ccctgtgtga tgtgggctcc   1140

ctgggcagct gggtccaccc cctggctggg aacgatggcc cagaggcgca gcaagagacc   1200

gatccatcct ga                                                       1212


<210> SEQ ID NO 83
<211> LENGTH: 403
<212> TYPE: PRT
<213> ORGANISM: Unknown
<220> FEATURE:
<223> OTHER INFORMATION: Novel Sequence

<400> SEQUENCE: 83

Met Ala Cys Asn Gly Ser Ala Ala Arg Gly His Phe Asp Pro Glu Asp
1               5                   10                  15

Leu Asn Leu Thr Asp Glu Ala Leu Arg Leu Lys Tyr Leu Gly Pro Gln
            20                  25                  30

Gln Thr Glu Leu Phe Met Pro Ile Cys Ala Thr Tyr Leu Leu Ile Phe
        35                  40                  45

Val Val Gly Ala Val Gly Asn Gly Leu Thr Cys Leu Val Ile Leu Arg
    50                  55                  60

His Lys Ala Met Arg Thr Pro Thr Asn Tyr Tyr Leu Phe Ser Leu Ala
65                  70                  75                  80

Val Ser Asp Leu Leu Val Leu Leu Val Gly Leu Pro Leu Glu Leu Tyr
                85                  90                  95

Glu Met Trp His Asn Tyr Pro Phe Leu Leu Gly Val Gly Gly Cys Tyr
            100                 105                 110

Phe Arg Thr Leu Leu Phe Glu Met Val Cys Leu Ala Ser Val Leu Asn
        115                 120                 125

Val Thr Ala Leu Ser Val Glu Arg Tyr Val Ala Val Val His Pro Leu
    130                 135                 140

Gln Ala Arg Ser Met Val Thr Arg Ala His Val Arg Arg Val Leu Gly
145                 150                 155                 160

Ala Val Trp Gly Leu Ala Met Leu Cys Ser Leu Pro Asn Thr Ser Leu
                165                 170                 175

His Gly Ile Arg Gln Leu His Val Pro Cys Arg Gly Pro Val Pro Asp
            180                 185                 190

Ser Ala Val Cys Met Leu Val Arg Pro Arg Ala Leu Tyr Asn Met Val
        195                 200                 205

Val Gln Thr Thr Ala Leu Leu Phe Phe Cys Leu Pro Met Ala Ile Met
    210                 215                 220

Ser Val Leu Tyr Leu Leu Ile Gly Leu Arg Leu Arg Arg Glu Arg Leu
225                 230                 235                 240

Leu Leu Met Gln Glu Ala Lys Gly Arg Gly Ser Ala Ala Ala Arg Ser
                245                 250                 255

Arg Tyr Thr Cys Arg Leu Gln Gln His Asp Arg Gly Arg Arg Gln Val
            260                 265                 270

Lys Lys Met Leu Phe Val Leu Val Val Val Phe Gly Ile Cys Trp Ala
        275                 280                 285

Pro Phe His Ala Asp Arg Val Met Trp Ser Val Val Ser Gln Trp Thr
    290                 295                 300

Asp Gly Leu His Leu Ala Phe Gln His Val His Val Ile Ser Gly Ile
305                 310                 315                 320

Phe Phe Tyr Leu Gly Ser Ala Ala Asn Pro Val Leu Tyr Ser Leu Met
                325                 330                 335
```

-continued

```
Ser Ser Arg Phe Arg Glu Thr Phe Gln Glu Ala Leu Cys Leu Gly Ala
            340                 345                 350

Cys Cys His Arg Leu Arg Pro Arg His Ser Ser His Ser Leu Ser Arg
        355                 360                 365

Met Thr Thr Gly Ser Thr Leu Cys Asp Val Gly Ser Leu Gly Ser Trp
    370                 375                 380

Val His Pro Leu Ala Gly Asn Asp Gly Pro Glu Ala Gln Gln Glu Thr
385                 390                 395                 400

Asp Pro Ser


<210> SEQ ID NO 84
<211> LENGTH: 930
<212> TYPE: DNA
<213> ORGANISM: Unknown
<220> FEATURE:
<223> OTHER INFORMATION: Novel Sequence

<400> SEQUENCE: 84

atgaatggca cctacaacac ctgtggctcc agcgacctca cctggccccc agcgatcaag      60

ctgggcttct acgcctactt gggcgtcctg ctggtgctag gcctgctgct caacagcctg     120

gcgctctggg tgttctgctg ccgcatgcag cagtggacgg agacccgcat ctacatgacc     180

aacctggcgg tggccgacct ctgcctgctg tgcaccttgc ccttcgtgct gcactccctg     240

cgagacacct cagacacgcc gctgtgccag ctctcccagg gcatctacct gaccaacagg     300

tacatgagca tcagcctggt cacggccatc gccgtggacc gctatgtggc cgtgcggcac     360

ccgctgcgtg cccgcgggct gcggtccccc aggcaggctg cggccgtgtg cgcggtcctc     420

tgggtgctgg tcatcggctc cctggtggct cgctggctcc tggggattca ggagggcggc     480

ttctgcttca ggagcacccg gcacaatttc aactccatgc ggttcccgct gctgggattc     540

tacctgcccc tggccgtggt ggtcttctgc tccctgaagg tggtgactgc cctggcccag     600

aggccaccca ccgacgtggg gcaggcagag gccacccgca aggctaaacg catggtctgg     660

gccaacctcc tggtgttcgt ggtctgcttc ctgcccctgc acgtggggct gacagtgcgc     720

ctcgcagtgg gctggaacgc ctgtgccctc ctggagacga tccgtcgcgc cctgtacata     780

accagcaagc tctcagatgc caactgctgc ctggacgcca tctgctacta ctacatggcc     840

aaggagttcc aggaggcgtc tgcactggcc gtggctcccc gtgctaaggc ccacaaaagc     900

caggactctc tgtgcgtgac cctcgcctaa                                      930


<210> SEQ ID NO 85
<211> LENGTH: 309
<212> TYPE: PRT
<213> ORGANISM: Unknown
<220> FEATURE:
<223> OTHER INFORMATION: Novel Sequence

<400> SEQUENCE: 85

Met Asn Gly Thr Tyr Asn Thr Cys Gly Ser Ser Asp Leu Thr Trp Pro
1               5                   10                  15

Pro Ala Ile Lys Leu Gly Phe Tyr Ala Tyr Leu Gly Val Leu Leu Val
            20                  25                  30

Leu Gly Leu Leu Leu Asn Ser Leu Ala Leu Trp Val Phe Cys Cys Arg
        35                  40                  45

Met Gln Gln Trp Thr Glu Thr Arg Ile Tyr Met Thr Asn Leu Ala Val
    50                  55                  60
```

-continued

```
Ala Asp Leu Cys Leu Leu Cys Thr Leu Pro Phe Val Leu His Ser Leu
65                  70                  75                  80

Arg Asp Thr Ser Asp Thr Pro Leu Cys Gln Leu Ser Gln Gly Ile Tyr
                85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Arg Phe Pro
                165                 170                 175

Leu Leu Gly Phe Tyr Leu Pro Leu Ala Val Val Val Phe Cys Ser Leu
            180                 185                 190

Lys Val Val Thr Ala Leu Ala Gln Arg Pro Pro Thr Asp Val Gly Gln
        195                 200                 205

Ala Glu Ala Thr Arg Lys Ala Lys Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Tyr Met Ala Lys Glu Phe Gln Glu Ala Ser Ala
        275                 280                 285

Leu Ala Val Ala Pro Arg Ala Lys Ala His Lys Ser Gln Asp Ser Leu
    290                 295                 300

Cys Val Thr Leu Ala
305
```

```
<210> SEQ ID NO 86
<211> LENGTH: 1446
<212> TYPE: DNA
<213> ORGANISM: Unknown
<220> FEATURE:
<223> OTHER INFORMATION: Novel Sequence

<400> SEQUENCE: 86

atgcggtggc tgtggcccct ggctgtctct cttgctgtga ttttggctgt ggggctaagc     60

agggtctctg ggggtgcccc cctgcacctg ggcaggcaca gagccgagac ccaggagcag    120

cagagccgat ccaagagggg caccgaggat gaggaggcca agggcgtgca gcagtatgtg    180

cctgaggagt gggcggagta cccccggccc attcaccctg ctggcctgca gccaaccaag    240

cccttggtgg ccaccagccc taacccccgac aaggatgggg gcaccccaga cagtgggcag    300

gaactgaggg gcaatctgac aggggcacca gggcagaggc tacagatcca gaaccccctg    360

tatccggtga ccgagagctc ctacagtgcc tatgccatca tgcttctggc gctggtggtg    420

tttgcggtgg gcattgtggg caacctgtcg gtcatgtgca tcgtgtggca cagctactac    480

ctgaagagcg cctggaactc catccttgcc agcctggccc tctgggattt tctggtcctc    540

tttttctgcc tccctattgt catcttcaac gagatcacca agcagaggct actgggtgac    600

gtttcttgtc gtgccgtgcc cttcatggag gtctcctctc tgggagtcac gactttcagc    660
```

```
ctctgtgccc tgggcattga ccgcttccac gtggccacca gcaccctgcc caaggtgagg    720

cccatcgagc ggtgccaatc catcctggcc aagttggctg tcatctgggt gggctccatg    780

acgctggctg tgcctgagct cctgctgtgg cagctggcac aggagcctgc ccccaccatg    840

ggcaccctgg actcatgcat catgaaaccc tcagccagcc tgcccgagtc cctgtattca    900

ctggtgatga cctaccagaa cgcccgcatg tggtggtact ttggctgcta cttctgcctg    960

cccatcctct tcacagtcac ctgccagctg gtgacatggc gggtgcgagg ccctccaggg   1020

aggaagtcag agtgcagggc cagcaagcac gagcagtgtg agagccagct caagagcacc   1080

gtggtgggcc tgaccgtggt ctacgccttc tgcaccctcc cagagaacgt ctgcaacatc   1140

gtggtggcct acctctccac cgagctgacc cgccagaccc tggacctcct gggcctcatc   1200

aaccagttct ccaccttctt caagggcgcc atcaccccag tgctgctcct ttgcatctgc   1260

aggccgctgg gccaggcctt cctggactgc tgctgctgct gctgctgtga ggagtgcggc   1320

ggggcttcgg aggcctctgc tgccaatggg tcggacaaca agctcaagac cgaggtgtcc   1380

tcttccatct acttccacaa gcccagggag tcacccccac tcctgcccct gggcacacct   1440

tgctga                                                              1446
```

<210> SEQ ID NO 87
<211> LENGTH: 481
<212> TYPE: PRT
<213> ORGANISM: Unknown
<220> FEATURE:
<223> OTHER INFORMATION: Novel Sequence

<400> SEQUENCE: 87

```
Met Arg Trp Leu Trp Pro Leu Ala Val Ser Leu Ala Val Ile Leu Ala
1               5                   10                  15

Val Gly Leu Ser Arg Val Ser Gly Gly Ala Pro Leu His Leu Gly Arg
            20                  25                  30

His Arg Ala Glu Thr Gln Glu Gln Gln Ser Arg Ser Lys Arg Gly Thr
        35                  40                  45

Glu Asp Glu Glu Ala Lys Gly Val Gln Gln Tyr Val Pro Glu Glu Trp
    50                  55                  60

Ala Glu Tyr Pro Arg Pro Ile His Pro Ala Gly Leu Gln Pro Thr Lys
65                  70                  75                  80

Pro Leu Val Ala Thr Ser Pro Asn Pro Asp Lys Asp Gly Gly Thr Pro
                85                  90                  95

Asp Ser Gly Gln Glu Leu Arg Gly Asn Leu Thr Gly Ala Pro Gly Gln
            100                 105                 110

Arg Leu Gln Ile Gln Asn Pro Leu Tyr Pro Val Thr Glu Ser Ser Tyr
        115                 120                 125

Ser Ala Tyr Ala Ile Met Leu Leu Ala Leu Val Val Phe Ala Val Gly
    130                 135                 140

Ile Val Gly Asn Leu Ser Val Met Cys Ile Val Trp His Ser Tyr Tyr
145                 150                 155                 160

Leu Lys Ser Ala Trp Asn Ser Ile Leu Ala Ser Leu Ala Leu Trp Asp
                165                 170                 175

Phe Leu Val Leu Phe Phe Cys Leu Pro Ile Val Ile Phe Asn Glu Ile
            180                 185                 190

Thr Lys Gln Arg Leu Leu Gly Asp Val Ser Cys Arg Ala Val Pro Phe
        195                 200                 205

Met Glu Val Ser Ser Leu Gly Val Thr Thr Phe Ser Leu Cys Ala Leu
```

-continued

```
    210                 215                 220

Gly Ile Asp Arg Phe His Val Ala Thr Ser Thr Leu Pro Lys Val Arg
225                 230                 235                 240

Pro Ile Glu Arg Cys Gln Ser Ile Leu Ala Lys Leu Ala Val Ile Trp
                245                 250                 255

Val Gly Ser Met Thr Leu Ala Val Pro Glu Leu Leu Leu Trp Gln Leu
            260                 265                 270

Ala Gln Glu Pro Ala Pro Thr Met Gly Thr Leu Asp Ser Cys Ile Met
        275                 280                 285

Lys Pro Ser Ala Ser Leu Pro Glu Ser Leu Tyr Ser Leu Val Met Thr
    290                 295                 300

Tyr Gln Asn Ala Arg Met Trp Trp Tyr Phe Gly Cys Tyr Phe Cys Leu
305                 310                 315                 320

Pro Ile Leu Phe Thr Val Thr Cys Gln Leu Val Thr Trp Arg Val Arg
                325                 330                 335

Gly Pro Pro Gly Arg Lys Ser Glu Cys Arg Ala Ser Lys His Glu Gln
            340                 345                 350

Cys Glu Ser Gln Leu Lys Ser Thr Val Val Gly Leu Thr Val Val Tyr
        355                 360                 365

Ala Phe Cys Thr Leu Pro Glu Asn Val Cys Asn Ile Val Val Ala Tyr
    370                 375                 380

Leu Ser Thr Glu Leu Thr Arg Gln Thr Leu Asp Leu Leu Gly Leu Ile
385                 390                 395                 400

Asn Gln Phe Ser Thr Phe Phe Lys Gly Ala Ile Thr Pro Val Leu Leu
                405                 410                 415

Leu Cys Ile Cys Arg Pro Leu Gly Gln Ala Phe Leu Asp Cys Cys Cys
            420                 425                 430

Cys Cys Cys Cys Glu Glu Cys Gly Gly Ala Ser Glu Ala Ser Ala Ala
        435                 440                 445

Asn Gly Ser Asp Asn Lys Leu Lys Thr Glu Val Ser Ser Ser Ile Tyr
    450                 455                 460

Phe His Lys Pro Arg Glu Ser Pro Pro Leu Leu Pro Leu Gly Thr Pro
465                 470                 475                 480

Cys


<210> SEQ ID NO 88
<211> LENGTH: 6
<212> TYPE: PRT
<213> ORGANISM: Unknown
<220> FEATURE:
<223> OTHER INFORMATION: Novel Sequence

<400> SEQUENCE: 88

Thr Leu Glu Ser Ile Met
1               5


<210> SEQ ID NO 89
<211> LENGTH: 5
<212> TYPE: PRT
<213> ORGANISM: Unknown
<220> FEATURE:
<223> OTHER INFORMATION: Novel Sequence

<400> SEQUENCE: 89

Glu Tyr Asn Leu Val
1               5
```

<210> SEQ ID NO 90
<211> LENGTH: 5
<212> TYPE: PRT
<213> ORGANISM: Unknown
<220> FEATURE:
<223> OTHER INFORMATION: Novel Sequence

<400> SEQUENCE: 90

Asp Cys Gly Leu Phe
1 5

<210> SEQ ID NO 91
<211> LENGTH: 34
<212> TYPE: DNA
<213> ORGANISM: Unknown
<220> FEATURE:
<223> OTHER INFORMATION: Novel Sequence

<400> SEQUENCE: 91
gatcaagctt ccatggcgtg ctgcctgagc gagg 34

<210> SEQ ID NO 92
<211> LENGTH: 53
<212> TYPE: DNA
<213> ORGANISM: Unknown
<220> FEATURE:
<223> OTHER INFORMATION: Novel Sequence

<400> SEQUENCE: 92
gatcggatcc ttagaacagg ccgcagtcct tcaggttcag ctgcaggatg gtg 53

<210> SEQ ID NO 93
<211> LENGTH: 5
<212> TYPE: PRT
<213> ORGANISM: Unknown
<220> FEATURE:
<223> OTHER INFORMATION: Novel Sequence

<400> SEQUENCE: 93

Gln Tyr Glu Leu Leu
1 5

<210> SEQ ID NO 94
<211> LENGTH: 5
<212> TYPE: PRT
<213> ORGANISM: Unknown
<220> FEATURE:
<223> OTHER INFORMATION: Novel Sequence

<400> SEQUENCE: 94

Asp Cys Gly Leu Phe
1 5

<210> SEQ ID NO 95
<211> LENGTH: 1185
<212> TYPE: DNA
<213> ORGANISM: Unknown
<220> FEATURE:
<223> OTHER INFORMATION: Novel Sequence

<400> SEQUENCE: 95
atgggctgcc tcggcaacag taagaccgag gaccagcgca acgaggagaa ggcgcagcgc 60
gaggccaaca aaaagatcga gaagcagctg cagaaggaca agcaggtcta ccgggccacg 120
caccgcctgc tgctgctggg tgctggagag tctggcaaaa gcaccattgt gaagcagatg 180
aggatcctac atgttaatgg gtttaacgga gagggcggcg aagaggaccc gcaggctgca 240

-continued

```
aggagcaaca gcgatggtga gaaggccacc aaagtgcagg acatcaaaaa caacctgaag    300

gaggccattg aaaccattgt ggccgccatg agcaacctgg tgccccccgt ggagctggcc    360

aaccctgaga accagttcag agtggactac attctgagcg tgatgaacgt gccaaacttt    420

gacttcccac ctgaattcta tgagcatgcc aaggctctgt gggaggatga gggagttcgt    480

gcctgctacg agcgctccaa cgagtaccag ctgatcgact gtgcccagta cttcctggac    540

aagattgatg tgatcaagca ggccgactac gtgccaagtg accaggacct gcttcgctgc    600

cgcgtcctga cctctggaat ctttgagacc aagttccagg tggacaaagt caacttccac    660

atgttcgatg tgggcggcca gcgcgatgaa cgccgcaagt ggatccagtg cttcaatgat    720

gtgactgcca tcatcttcgt ggtggccagc agcagctaca acatggtcat ccgggaggac    780

aaccagacca accgtctgca ggaggctctg aacctcttca agagcatctg gaacaacaga    840

tggctgcgta ccatctctgt gatcctcttc ctcaacaagc aagatctgct tgctgagaag    900

gtcctcgctg ggaaatcgaa gattgaggac tactttccag agttcgctcg ctacaccact    960

cctgaggatg cgactcccga gcccggagag gacccacgcg tgacccgggc caagtacttc   1020

atccgggatg agtttctgag aatcagcact gctagtggag atggacgtca ctactgctac   1080

cctcacttta cctgcgccgt ggacactgag aacatccgcc gtgtcttcaa cgactgccgt   1140

gacatcatcc agcgcatgca tcttcgcgac tgcgggctgt tttaa                    1185
```

<210> SEQ ID NO 96
<211> LENGTH: 393
<212> TYPE: PRT
<213> ORGANISM: Unknown
<220> FEATURE:
<223> OTHER INFORMATION: Novel Sequence

<400> SEQUENCE: 96

```
Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
        35                  40                  45

Gly Glu Ser Gly Lys Ser Thr Ile Val Lys Gln Met Arg Ile Leu His
    50                  55                  60

Val Asn Gly Phe Asn Gly Glu Gly Gly Glu Glu Asp Pro Gln Ala Ala
65                  70                  75                  80

Arg Ser Asn Ser Asp Gly Glu Lys Ala Thr Lys Val Gln Asp Ile Lys
                85                  90                  95

Asn Asn Leu Lys Glu Ala Ile Glu Thr Ile Val Ala Ala Ser Asn Leu
            100                 105                 110

Val Pro Pro Val Glu Leu Ala Asn Pro Glu Asn Gln Phe Arg Val Asp
        115                 120                 125

Tyr Ile Leu Ser Val Met Asn Val Pro Asn Phe Asp Phe Pro Pro Glu
    130                 135                 140

Phe Tyr Glu His Ala Lys Ala Leu Trp Glu Asp Glu Gly Val Arg Ala
145                 150                 155                 160

Cys Tyr Glu Arg Ser Asn Glu Tyr Gln Leu Ile Asp Cys Ala Gln Tyr
                165                 170                 175

Phe Leu Asp Lys Ile Asp Val Ile Lys Gln Ala Asp Tyr Val Pro Ser
            180                 185                 190
```

-continued

```
Asp Gln Asp Leu Leu Arg Cys Arg Val Leu Thr Ser Gly Ile Phe Glu
        195                 200                 205

Thr Lys Phe Gln Val Asp Lys Val Asn Phe His Met Phe Asp Val Gly
    210                 215                 220

Gly Gln Arg Asp Glu Arg Arg Lys Trp Ile Gln Cys Phe Asn Asp Val
225                 230                 235                 240

Thr Ala Ile Ile Phe Val Val Ala Ser Ser Ser Tyr Asn Met Val Ile
                245                 250                 255

Arg Glu Asp Asn Gln Thr Asn Arg Leu Gln Glu Ala Leu Asn Leu Phe
            260                 265                 270

Lys Ser Ile Trp Asn Asn Arg Trp Leu Arg Thr Ile Ser Val Ile Leu
        275                 280                 285

Phe Leu Asn Lys Gln Asp Leu Leu Ala Glu Lys Val Leu Ala Gly Lys
    290                 295                 300

Ser Lys Ile Glu Asp Tyr Phe Pro Glu Phe Ala Arg Tyr Thr Thr Pro
305                 310                 315                 320

Glu Asp Ala Thr Pro Glu Pro Gly Glu Asp Pro Arg Val Thr Arg Ala
                325                 330                 335

Lys Tyr Phe Ile Arg Asp Glu Phe Leu Arg Ile Ser Thr Ala Ser Gly
            340                 345                 350

Asp Gly Arg His Tyr Cys Tyr Pro His Phe Thr Cys Ala Val Asp Thr
        355                 360                 365

Glu Asn Ile Arg Arg Val Phe Asn Asp Cys Arg Asp Ile Ile Gln Arg
    370                 375                 380

Met His Leu Arg Asp Cys Gly Leu Phe
385                 390
```

<210> SEQ ID NO 97
<211> LENGTH: 1014
<212> TYPE: DNA
<213> ORGANISM: Homo sapiens

<400> SEQUENCE: 97

```
atgaactcgt gggacgcggg cctggcgggg ctactggtgg gcacgatggg cgtctcgctg      60

ctgtccaacg cgctggtgct gctctgcctg ctgcacagcg cggacatccg ccgccaggcg     120

ccggcgctct tcaccctgaa cctcacgtgc gggaacctgc tgtgcaccgt ggtcaacatg     180

ccgctcacgc tggccggcgt cgtggcgcag cggcagccgg cgggcgaccg cctgtgccgc     240

ctggctgcct tcctcgacac cttcctggct gccaactcca tgctcagcat ggccgcgctc     300

agcatcgacc gctgggtggc cgtggtcttc ccgctgagct accgggccaa gatgccgcct     360

ccgagatgcg cgctcatcct ggcctacacg tggctgcacg cgctcacctt cccagccgcc     420

gcgctcgccc tgtcctggct cggcttccac cagctgtacg cctcgtgcac gctgtgcagc     480

cggcggccgg acgagcgcct gcgcttcgcc gtattcactg gcgccttcca cgctctcagc     540

ttcctgctct ccttcgtcgt gctctgctgc acgtacctca aggtgctcaa ggtggcccgc     600

ttccattgca agcgcatcga cgtgatcacc atgcagacgc tcgtgctgct ggtggacctg     660

caccccagtg tgcgggaacg ctgtctggag gagcagaagc ggaggcgaca gcgagccacc     720

aagaagatca gcaccttcat agggaccttc cttgtgtgct tcgcgcccta tgtgatcacc     780

aggctagtgg agctcttctc cacggtgccc atcggctccc actgggggt gctgtccaag      840

tgcttggcgt acagcaaggc cgcatccgac ccctttgtgt actccttact gcgacaccag     900

taccgcaaaa gctgcaagga gattctgaac aggctcctgc acagacgctc catccactcc     960
```

-continued

```
tctggcctca caggcgactc tcacagccag aacattctgc cggtgtctga gtga        1014


<210> SEQ ID NO 98
<211> LENGTH: 337
<212> TYPE: PRT
<213> ORGANISM: Homo sapiens

<400> SEQUENCE: 98

Met Asn Ser Trp Asp Ala Gly Leu Ala Gly Leu Leu Val Gly Thr Met
1               5                   10                  15

Gly Val Ser Leu Leu Ser Asn Ala Leu Val Leu Leu Cys Leu Leu His
            20                  25                  30

Ser Ala Asp Ile Arg Arg Gln Ala Pro Ala Leu Phe Thr Leu Asn Leu
        35                  40                  45

Thr Cys Gly Asn Leu Leu Cys Thr Val Val Asn Met Pro Leu Thr Leu
    50                  55                  60

Ala Gly Val Val Ala Gln Arg Gln Pro Ala Gly Asp Arg Leu Cys Arg
65                  70                  75                  80

Leu Ala Ala Phe Leu Asp Thr Phe Leu Ala Ala Asn Ser Met Leu Ser
                85                  90                  95

Met Ala Ala Leu Ser Ile Asp Arg Trp Val Ala Val Val Phe Pro Leu
            100                 105                 110

Ser Tyr Arg Ala Lys Met Pro Pro Pro Arg Cys Ala Leu Ile Leu Ala
        115                 120                 125

Tyr Thr Trp Leu His Ala Leu Thr Phe Pro Ala Ala Ala Leu Ala Leu
    130                 135                 140

Ser Trp Leu Gly Phe His Gln Leu Tyr Ala Ser Cys Thr Leu Cys Ser
145                 150                 155                 160

Arg Arg Pro Asp Glu Arg Leu Arg Phe Ala Val Phe Thr Gly Ala Phe
                165                 170                 175

His Ala Leu Ser Phe Leu Leu Ser Phe Val Val Leu Cys Cys Thr Tyr
            180                 185                 190

Leu Lys Val Leu Lys Val Ala Arg Phe His Cys Lys Arg Ile Asp Val
        195                 200                 205

Ile Thr Met Gln Thr Leu Val Leu Leu Val Asp Leu His Pro Ser Val
    210                 215                 220

Arg Glu Arg Cys Leu Glu Glu Gln Lys Arg Arg Arg Gln Arg Ala Thr
225                 230                 235                 240

Lys Lys Ile Ser Thr Phe Ile Gly Thr Phe Leu Val Cys Phe Ala Pro
                245                 250                 255

Tyr Val Ile Thr Arg Leu Val Glu Leu Phe Ser Thr Val Pro Ile Gly
            260                 265                 270

Ser His Trp Gly Val Leu Ser Lys Cys Leu Ala Tyr Ser Lys Ala Ala
        275                 280                 285

Ser Asp Pro Phe Val Tyr Ser Leu Leu Arg His Gln Tyr Arg Lys Ser
    290                 295                 300

Cys Lys Glu Ile Leu Asn Arg Leu Leu His Arg Arg Ser Ile His Ser
305                 310                 315                 320

Ser Gly Leu Thr Gly Asp Ser His Ser Gln Asn Ile Leu Pro Val Ser
                325                 330                 335

Glu


<210> SEQ ID NO 99
<211> LENGTH: 21
<212> TYPE: DNA
```

-continued

```
<213> ORGANISM: Unknown
<220> FEATURE:
<223> OTHER INFORMATION: Novel Sequence

<400> SEQUENCE: 99

cgagaaggtg ctcaaggtgg c                                               21


<210> SEQ ID NO 100
<211> LENGTH: 30
<212> TYPE: DNA
<213> ORGANISM: Unknown
<220> FEATURE:
<223> OTHER INFORMATION: Novel Sequence

<400> SEQUENCE: 100

gagaagagct ccactagcct ggtgatcaca                                      30


<210> SEQ ID NO 101
<211> LENGTH: 36
<212> TYPE: DNA
<213> ORGANISM: Unknown
<220> FEATURE:
<223> OTHER INFORMATION: Novel Sequence

<400> SEQUENCE: 101

gaattcatga actcgtggga cgcgggcctg gcgggc                               36


<210> SEQ ID NO 102
<211> LENGTH: 32
<212> TYPE: DNA
<213> ORGANISM: Unknown
<220> FEATURE:
<223> OTHER INFORMATION: Novel Sequence

<400> SEQUENCE: 102

ctcgagtcac tcagacaccg gcagaatgtt ct                                   32
```